(12) United States Patent
Gordin et al.

(10) Patent No.: US 11,071,177 B2
(45) Date of Patent: Jul. 20, 2021

(54) LIGHTING OPTIMIZED FOR MELANOPIC VISION

(71) Applicant: Musco Corporation, Oskaloosa, IA (US)

(72) Inventors: Myron Gordin, Oskaloosa, IA (US); Bradley D. Schlesselman, Oskaloosa, IA (US)

(73) Assignee: Musco Corporation, Oskaloosa, IA (US)

( * ) Notice: Subject to any disclaimer, the term of this patent is extended or adjusted under 35 U.S.C. 154(b) by 152 days.

(21) Appl. No.: 16/234,063

(22) Filed: Dec. 27, 2018

(65) Prior Publication Data

US 2019/0223264 A1 Jul. 18, 2019

Related U.S. Application Data

(62) Division of application No. 15/382,232, filed on Dec. 16, 2016, now Pat. No. 10,212,766.

(Continued)

(51) Int. Cl.
*H05B 33/08* (2020.01)
*A61N 5/06* (2006.01)
(Continued)

(52) U.S. Cl.
CPC ........... *H05B 33/08* (2013.01); *A61N 5/0618* (2013.01); *H05B 45/20* (2020.01); *H05B 47/10* (2020.01)

(58) Field of Classification Search
None
See application file for complete search history.

(56) References Cited

U.S. PATENT DOCUMENTS

| 6,631,987 B2 | 10/2003 | Reichow et al. |
| 7,520,607 B2 * | 4/2009 | Casper ................... G02C 7/10 351/159.65 |

(Continued)

FOREIGN PATENT DOCUMENTS

| KR | 1020150026968 | 3/2015 |
| WO | 2013151661 A1 | 10/2013 |

(Continued)

OTHER PUBLICATIONS

Musco Corporation, PCT/US2016/067340 filed Dec. 16, 2016, "Notification of Transmittal of the International Search Report and the Written Opinion of the International Searching Authority, or the Declaration" dated May 30, 2017.

(Continued)

*Primary Examiner* — Ashok Patel
(74) *Attorney, Agent, or Firm* — McKee, Voorhees & Sease, PLC

(57) ABSTRACT

Methods, apparatus, and systems for illumination, including wide area lighting applications. In one embodiment, a method of illumination comprises: comparing metamers at a known and similar CCT with at least one metamer having a higher M/P or S/P ratio; selecting at least one of said metamers for improved perceived brightness; evaluating the selected metamer(s) for desired CCT and acceptable CRI; manufacturing a lighting apparatus which emits light of a given CCT having increased melanopic content compared to one or more extant metameric variations of the same or similar CCT; wherein said light has an acceptable CRI. The method can be applied in various apparatus and systems. In one example, the methods, apparatus, and systems can be used to illuminate a wide area target area with increased perceived brightness compared to typical similar lighting. In (Continued)

some cases, this allows energy savings and/or fewer lighting sources or fixtures than typical lighting.

9 Claims, 80 Drawing Sheets

Related U.S. Application Data

(60) Provisional application No. 62/345,559, filed on Jun. 3, 2016, provisional application No. 62/269,642, filed on Dec. 18, 2015.

(51) Int. Cl.
*H05B 45/20* (2020.01)
*H05B 47/10* (2020.01)

(56) References Cited

U.S. PATENT DOCUMENTS

| | | | |
|---|---|---|---|
| 9,681,510 | B2 | 6/2017 | van De Ven |
| 10,201,056 | B1 * | 2/2019 | Gordin .................. H05B 45/22 |
| 2012/0068608 | A1 | 3/2012 | Covaro et al. |
| 2012/0206050 | A1 | 8/2012 | Spero |
| 2013/0238060 | A1 | 9/2013 | Nevins |
| 2013/0293150 | A1 | 11/2013 | Maxik et al. |
| 2017/0348506 | A1 | 12/2017 | Berman et al. |
| 2018/0056027 | A1 | 3/2018 | Peeters et al. |
| 2018/0073712 | A1 | 3/2018 | Baaijens et al. |

FOREIGN PATENT DOCUMENTS

| | | |
|---|---|---|
| WO | 2014189945 A1 | 11/2014 |
| WO | 2015014936 A1 | 2/2015 |

OTHER PUBLICATIONS

Berman, "New Discoveries in Vision Affect Lighting Practice", Lawrence Berkeley National Laboratory, 8 pages, 2012.
CREE Technical Article, "LED Color Mixing: Basics and Background", www.cree.com/xlamp, copyright 2010-2015.
Horiguchi, et al., "Human Trichromacy Revisited", PNAS Plus, 10 pages, approved Nov. 15, 2012.
Lewin, Ian, "Lamp Color and Visibility in Outdoor Lighting Design", Lighting Sciences Inc., 14 pages, 1999.
George Kelly, "Understand Color Science to Maximize Success with LEDs", LEDs Magazine, 7 pgs,, http://www.ledsmagazine.com/articles/2012/05/understand-color-science-to-maximize-success-with-leds-magazine.html, accessed by applicant on Dec. 17, 2015.
Schlesselman, et al., "Brightness judgments in a simulated sports field correlate with the S/P value of light sources", Musco Sports Lighting, LLC, 18 pages, 2015.
Schlesselman, et al., "Brightness matching determines the trade-off between S/P values and illuminance level", Musco Sports Lighting, LLC, 16 pages, 2015.
Spitschan et al., "Opponent Melanopsin and S-cone Signals in the Human Pupillary Light Response", pp. 15568-15572, vol. 111, No. 43, PNAS article, published Oct. 28, 2014.
Vienot F, "Domain of Metamers Exciting Intrinsically Photosensitive Retinal Ganglion Cells (ipRGCs) and Rods", http://www.ncbi.nim.nih.gov/pubmed22330402, 2 pages, accessed online Nov. 20, 2014.

* cited by examiner

Introduction to Colorimetry

Method of measuring and evaluating color
CIE is driving force behind development of colorimetry
CIE is responsible for defining and specifying colorimetry via their publications

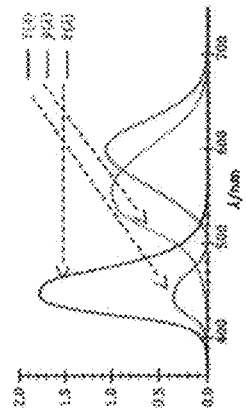

Foundations of colorimetry
Human visual color responses
Spectral measurements of illuminants and objects
Defined in the context of a color space

Backbone of colorimetry
Tristimulus Specification — based on rules of color matching by additive color mixture

$$X = K_m \int S(\lambda) \bar{x}(\lambda) d\lambda$$

$$Y = K_m \int S(\lambda) \bar{y}(\lambda) d\lambda$$

$$Z = K_m \int S(\lambda) \bar{z}(\lambda) d\lambda$$

Fig 2B

Additive Color Mixture Laws

1. Trichromacy
   All colors can be matched by a mixture of three different stimuli as long as none of the stimuli can be matched in color by a mixture of the others.

2. Metamers
   Stimuli with different spectral power distributions may provide the same color match 3. Proportionality and additivity
   If one component of the mixture changes, the color of the mixture changes in a corresponding manner

Fig 2C

Color Matching Functions
Results of matching experiment tabulated as a function of each primary contribution for each wavelength
Color matching function is derived by converting r,g,b primary to x,y,z and scaling for photopic luminous efficiency function.
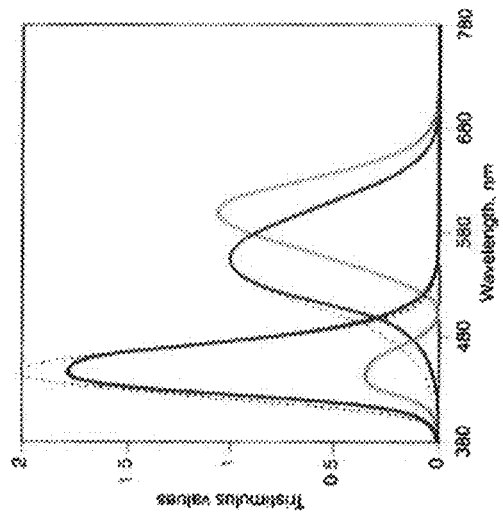
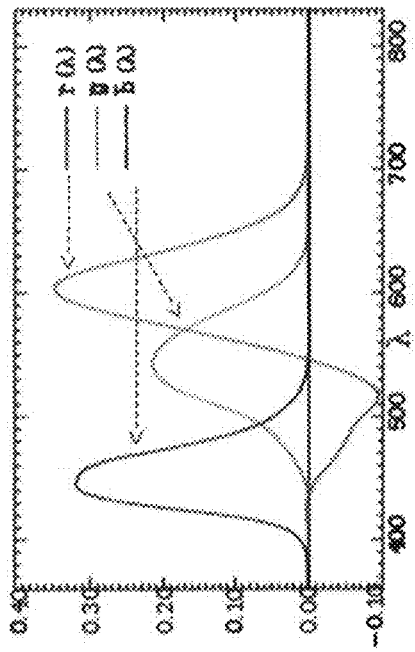
Fig 2E

Mathematical Formulation via Linear Algebra $$X = RX_{r,max} + GX_{g,max} + BX_{b,max}$$
$$Y = RY_{r,max} + GY_{g,max} + BY_{b,max}$$
$$Z = RZ_{r,max} + GZ_{g,max} + BZ_{b,max}$$

$$\begin{bmatrix} X \\ Y \\ Z \end{bmatrix} = \begin{bmatrix} X_{r,max} & X_{g,max} & X_{b,max} \\ Y_{r,max} & Y_{g,max} & Y_{b,max} \\ Z_{r,max} & Z_{g,max} & Z_{b,max} \end{bmatrix} \begin{bmatrix} R \\ G \\ B \end{bmatrix}$$

$$\begin{bmatrix} R \\ G \\ B \end{bmatrix} = \begin{bmatrix} X_{r,max} & X_{g,max} & X_{b,max} \\ Y_{r,max} & Y_{g,max} & Y_{b,max} \\ Z_{r,max} & Z_{g,max} & Z_{b,max} \end{bmatrix}^{-1} \begin{bmatrix} X \\ Y \\ Z \end{bmatrix}$$

Allows solution of primary mixture to achieve specific Tristimulus value

Fig 21

Metamer Creation

Wysecki hypothesized that any spectrum N could be broken down into a fundamental metamer N* and a black metamer B $$N = N^* + B$$

N and N* both have the same Tristimulus values and thus the same color appearance B is a black metamer and has Tristimulus values of 0 0 0 and therefore does not contribute to color perception.

Black metamers are not physically realizable, but are mathematically useful in calculating new metamers

Fig 2K

Matrix R Theory

Matrix R is a special linear algebra operator that enables one to calculate the fundamental metamer from a spectrum.

Matrix R is derived solely from the color matching function.

When the spectrum N is multiplied by Matrix R the result is N* the fundamental metamer.

$$N^* = R \times N$$

The Black metamer is then found by subtracting N* from N $$B = N - N^*$$

Fig 2L

Application to Spectrum Enhancing

Black metamers can be added to fundamentals to create new metamers

New black metamers can be generated by multiplying the existing black metamer by a scaling factor and adding it back to the fundamental This essentially creates the opportunity for optimizing the black metamer for non visual effects without affecting the perceived color (aka color temperature) of the source The problem can be formulated as a linear programming problem to minimize/maximize an objective by changing weights on metamer For example, the black metamers that give the highest scotopic to photopic ratio could be solved for a given primary system to improve potential perceived brightness and acuity

Fig 2N

Software and Hardware Tools

Software Development

Using C#.NET to develop code modules:
- Base Color Calculations (substantially complete)
- Optimization code for finding metamers (in progress)
- Conversion of primary weights to DMX values (in progress)

Hardware Tools

- 2 Prism projection units configured to allow for individual LED channel control via DMX
- Stand alone DMX manual controller for demo and hand tweaking
- USB to DMX controller for automated control from computer during research studies
- USB spectrometer for measuring spectrum and color properties of LED primaries and output mixture
- S/P meter on order for field verification of mixture optimization

Fig 20

Brightness Equivalency (BE)
Proposed Simplified Approach by Sam Berman, et al $$BE\ (M/P) = Lux_{Source1} / Lux_{Source2} = [(M/P)_{Source2}/(M/P)_{Source1}]^{0.32}$$

Example with M/P as a function of CCT & CRI {M/P(CCT,CRI)}:

Source1: M/P(4500,81) = 5.0
Source2: M/P(6500,64) = 7.3;
Given: application of Source2 yields 100 lux of photopic illuminance
BE(M/P) = (7.3/5.0)$^{0.32}$ = 1.129 ≈ 113 lux with Source1 to have BE with Source2 which is at 100 lux Application Source1: Musco's LA-30Z-1: CCT @4,200K; M/P = 3.51; CRI = 68
Given: application of Source2 yields 100 lux of photopic illuminance
Source2: 4,500K LED: CCT 4,439; M/P = 3.55; CRI 75
  BE(M/P) = (3.55/3.51)$^{0.32}$ = 1.0036 ≈ 100.4 lux with Source1 to have BE with Source2

Source2: Cree XP-L: CCT 6,263; M/P = 3.92; CRI = 67
  BE(M/P) = (3.92/3.51)$^{0.32}$ = 1.036 ≈ 104 lux with Source1 to have BE with Source2

Source2: MET20160309_1: CCT 6,500K; M/P 7.3; CRI 64
  BE(M/P) = (7.3/3.51)$^{0.32}$ = 1.264 ≈ 126 lux with Source1 to have BE with Source2

Source2: MET20160309_4: CCT 5,600K; M/P 6.8; CRI 65
  BE(M/P) = (6.8/3.51)$^{0.32}$ = 1.226 ≈ 123 lux with Source1 to have BE with Source2

Source2: MET20160309_12: CCT 17,000K; M/P 9.5; CRI 65
  BE(M/P) = (9.5/3.51)$^{0.32}$ = 1.375 ≈ 138 lux with Source1 to have BE with Source2

Note: If using S/P ratio, use 0.436 as exponent

Fig 3B

Brightness Equivalency Variation $$R_2 = e^{(\ln(r^{-1} \cdot R_1^c) \cdot c^{-1})}$$

where:

- $R_1$ = Base Source Ratio, i.e. M/P = 2.50
- $R_2$ = Required Ratio of 2nd Source to achieve desired Light Reduction
- r = Light Reduction, i.e. to 75%
- c = Exponent for Brightness Equivalence, i.e. 0.32

Example:

$$R_2 = e^{(\ln(0.75^{-1} \cdot 2.50^{0.32}) \cdot 0.32^{-1})}$$

$$R_2 = 6.14$$

So, if you had a light source with an M/P ratio of 2.50 and wanted to reduce photopic light levels by 25% (to 75%) while maintaining equivalent brightness, you would need the second light source to have an M/P ratio of 6.14.

Fig 3C

Parameters / Inputs

- SPD Inputs (All normalized to 1.0 at peak):
  - 450[10]630 monochromatic light
  - Melanopic Curve
- Min CRI 60
- Metamers generated in Musco developed 'Light Metric' application
- Melanopic function taken from Lucas (Faculty of Life Sciences, University of Manchester, Manchester M13 9PT, UK), et al, *Lucas et al 2014 workbook.xls*, 2014
  - Maximum spectral efficacy ($K^*_m$)
    - $K^*_m = K_m / (\phi_{z,555} / \phi_{z,490}) = 4,214.6 \approx 4,215$
    - Where $K_m = 683$; $\phi_{z,555} = 0.0018483287$; $\phi_{z,490} = 0.0114055016$
    - $\phi_{z,\lambda}$ = spectral power from the melanopic function at the specified wavelength

Fig 3D

MET20160510_4
17,000K; CRI 86, R9 78; M/P 8.0; TLCI 74

MET20160510_5
10,000K; CRI 66, R9 77; M/P 8.5; TLCI 52

MET20160510_6
10,000K; CRI 75, R9 78; M/P 8.0; TLCI 75

MET20160510_12
5,700K; CRI 81, R9 60; M/P 6.0; TLCI 70

MET20160510_15
4,500K; CRI 78, R9 46; M/P 5.25; TLCI 59

Standard Observer: CIE1931_2de9
Chromaticity Coordinates (abscissa,ordinate): 0.26019, 0.26265
Primaries Used (Weight Function); Max
--------
User Input M/P Ratio: 9.5
Fitness: 3.306E-05
Color Weights
Melanopic_curve: 0.42
450:        1
460:        0.778
470:        0.592
480:        0.598
490:        0.413
500:        0.482
510:        0.282
520:        0.067
530:        0.089
540:        0.076
550:        0.059
560:        0.466
570:        0.188
580:        0.19
590:        0.255
600:        0.183
610:        0.083
620:        0.448
630:        0.673
Percentage of Maximum Fixture Flux: 25.75%

Fig 5

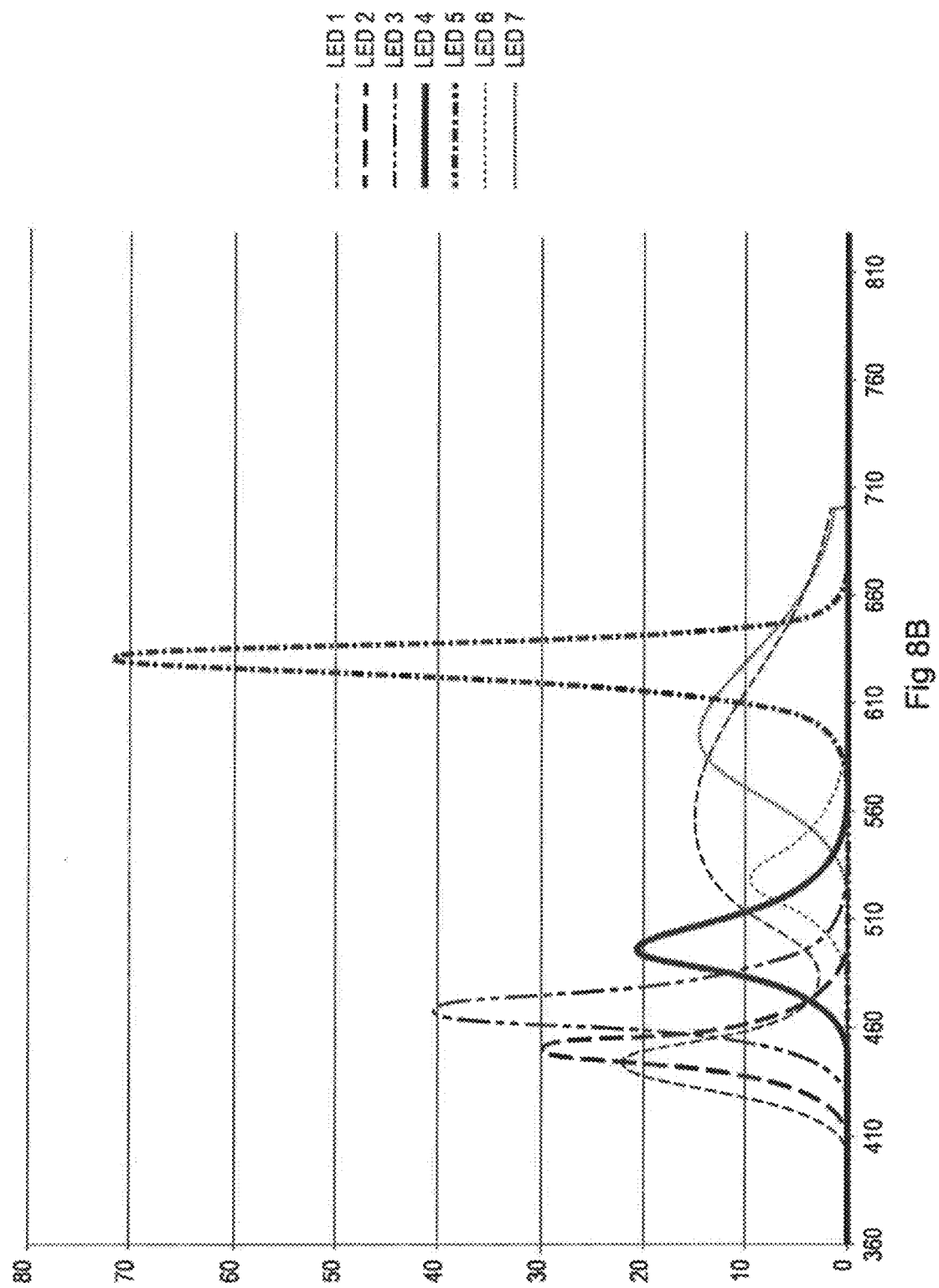

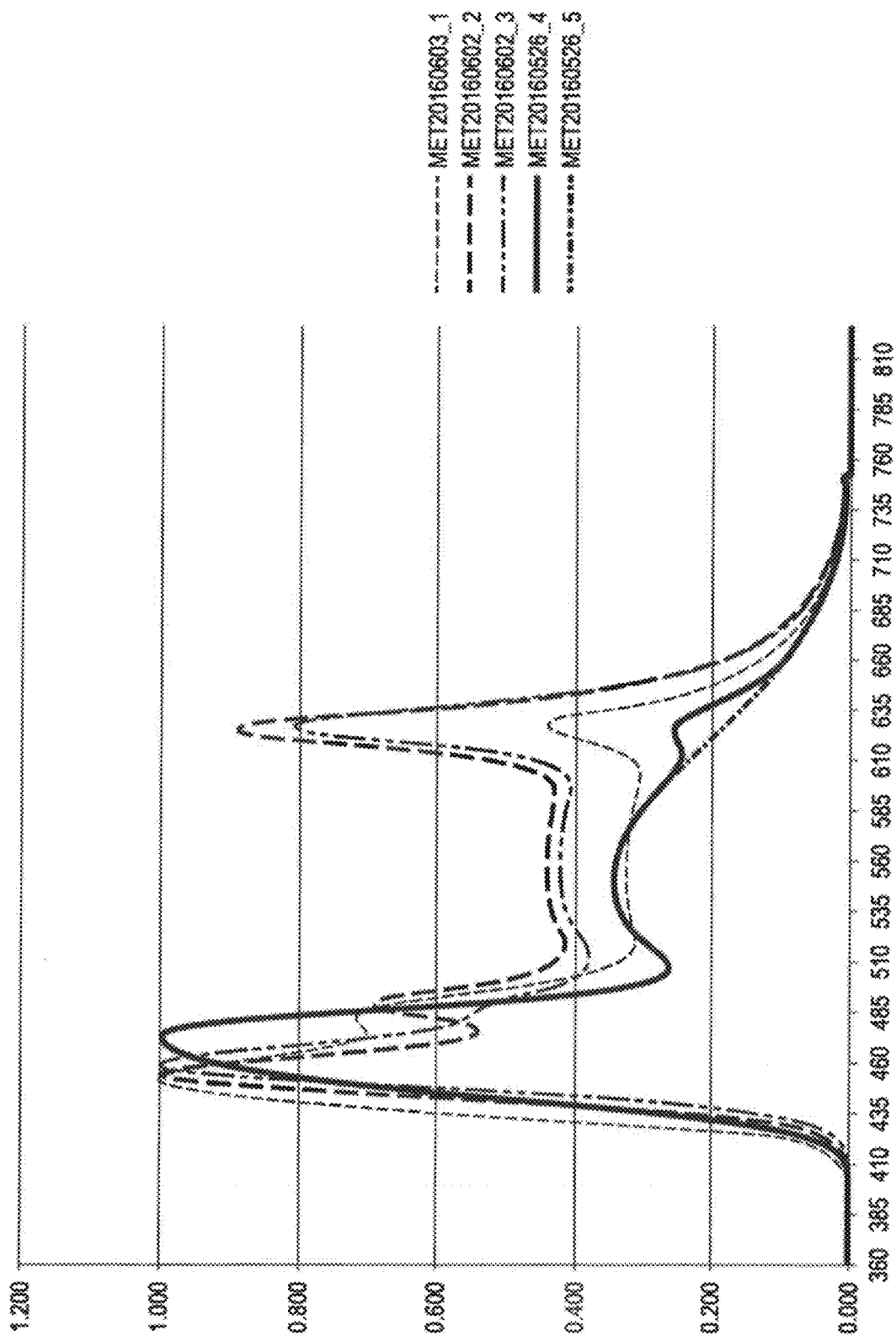

Figure 6: CIE Diagram of the seven LED sources and the resultant metamers.

Cross sectional view of simulated sports field and lighting layout. Observer is positioned looking at field simulation with 4' eye height achieved by adjustable height chair.

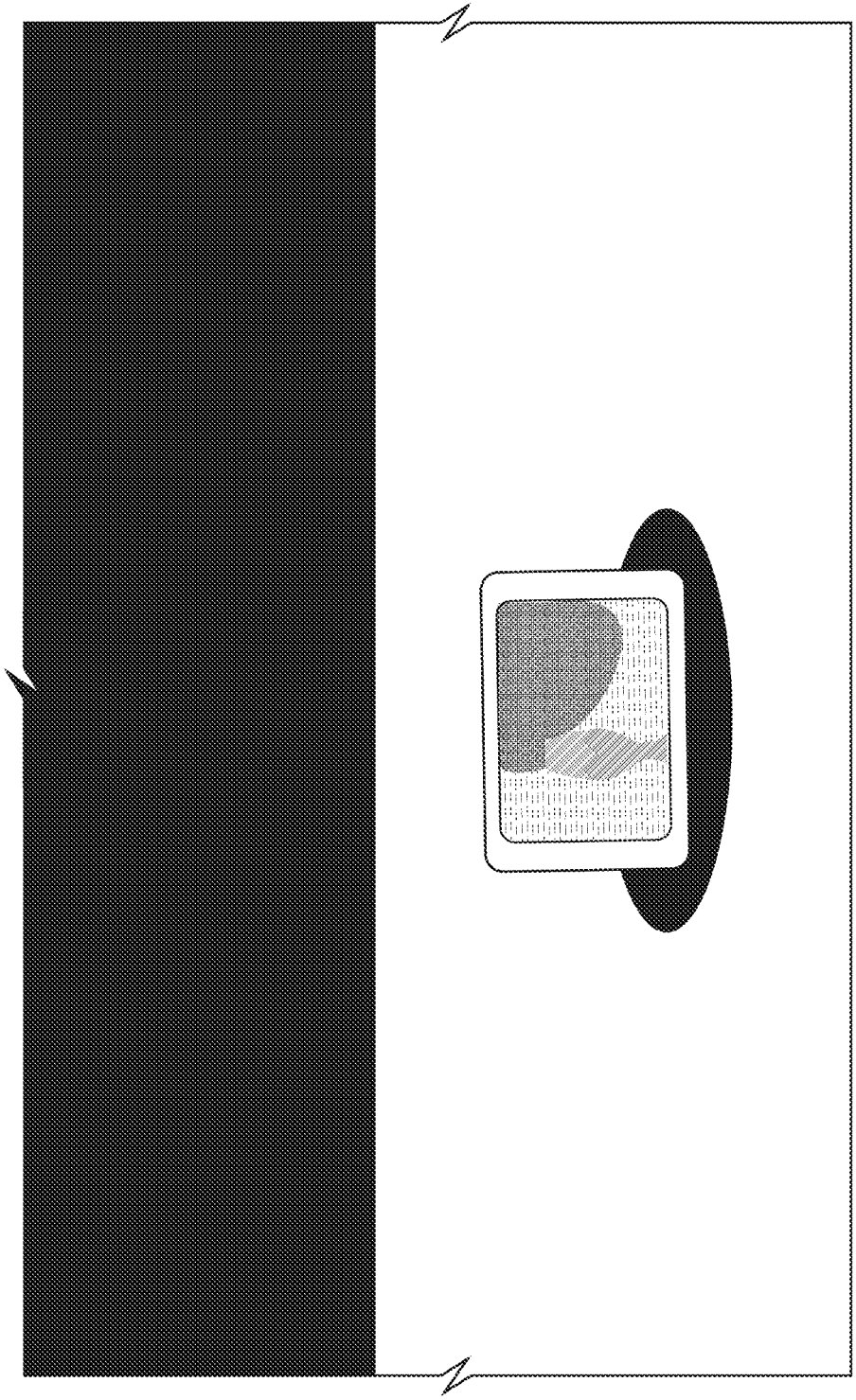

Floor, chair and lit platform, perspective view from right hand side of platform ETC fixture CIE Diagram of the seven LED sources and the resultant metamers Summary Findings: Brightness Comparison Results for 47 Subjects
% of Subjects Higher S/P Lighting as Brighter

| BC Test | | High S/P | 3.069 | 3.039 | 3.041 | 2.086 | 2.064 | 3.938 | 3.938 | 2.599 | 2.582 |
|---|---|---|---|---|---|---|---|---|---|---|---|
| | | Low S/P | 2.134 | 2.117 | 2.111 | 1.346 | 1.352 | 2.077 | 2.058 | 1.217 | 1.233 |
| | | Delta S/P | 0.935 | 0.922 | 0.930 | 0.740 | 0.712 | 1.861 | 1.880 | 1.382 | 1.348 |
| Age Group | Qty | Avg Across Tests | HS-60 | HS-150 | HS-450 | LS-60 | LS-150 | HW-60 | HW-150 | LW-60 | LW-150 |
| 18-30 | 17 | 84% | 65% | 76% | 82% | 88% | 94% | 76% | 88% | 88% | 94% |
| 31-50 | 16 | 91% | 81% | 81% | 88% | 94% | 100% | 94% | 94% | 88% | 100% |
| 51-Older | 14 | 92% | 86% | 93% | 93% | 93% | 93% | 79% | 93% | 100% | 100% |
| Total | 47 | 89% | 76.6% | 83.0% | 87.2% | 91.5% | 95.7% | 83.0% | 91.5% | 91.5% | 97.9% |
| Ave for both light levels | | | 79.8% | | 87.2% | 93.6% | | 87.2% | | 94.7% | |

Table 4: Summary results from the Brightness Comparison (BC) Test.

*FIG. 14*

| Pair | Description | Code | Illuminance Levels | | | Illuminance Levels | | |
|---|---|---|---|---|---|---|---|---|
| | | | 60 S/P | 150 S/P | 400 S/P | 60 CCT | 150 CCT | 400 CCT |
| 1 | High CCT Wide S/P Spread | HWH | 3.952 | 3.898 | | 5653 | 5475 | |
| | | HWL | 2.088 | 2.064 | | 6580 | 6380 | |
| | | Delta | 1.864 | 1.834 | | -927 | -905 | |
| 2 | High CCT Small S/P Spread | HSH | 3.087 | 3.009 | 2.937 | 6444 | 6224 | 5992 |
| | | HSL | 2.145 | 2.128 | 2.117 | 6706 | 6588 | 6434 |
| | | Delta | 0.942 | 0.881 | 0.820 | -262 | -364 | -442 |
| 3 | Low CCT Wide S/P Spread | LWH | 2.610 | 2.599 | | 2389 | 2373 | |
| | | LWL | 1.222 | 1.239 | | 3103 | 3149 | |
| | | Delta | 1.388 | 1.360 | | -714 | -776 | |
| 4 | Low CCT Small S/P Spread | LSH | 2.098 | 2.073 | | 2713 | 2688 | |
| | | LSL | 1.352 | 1.356 | | 3040 | 3054 | |
| | | Delta | 0.746 | 0.717 | | -327 | -366 | |

Table 1: Lighting Conditions: Verical DOG Illuminance, S/P values and CCT values.

*FIG. 15*

Summary Findings: Brightness Matching Results for 40 Subjects:
% of Subjects Selecting Lower Illumination for High S/P Lighting

| BM Test | | High S/P | 3.078 | 3.044 | | 2.087 | 2.066 | 3.943 | 3.943 | 2.599 | 2.581 |
|---|---|---|---|---|---|---|---|---|---|---|---|
| | | Low S/P | 2.133 | 2.117 | | 1.347 | 1.354 | 2.075 | 2.058 | 1.221 | 1.236 |
| | | Delta S/P | 0.945 | 0.927 | | 0.740 | 0.712 | 1.868 | 1.885 | 1.378 | 1.345 |
| Age Group | Qty | Avg Across Tests | HS-60 | HS-150 | | LS-60 | LS-150 | HW-60 | HW-150 | LW-60 | LW-150 |
| 18-30 | 16 | 87% | 69% | 63% | | 88% | 88% | 94% | 94% | 100% | 100% |
| 31-50 | 12 | 93% | 83% | 92% | | 100% | 92% | 83% | 92% | 100% | 100% |
| 51-Older | 12 | 97% | 100% | 100% | | 83% | 100% | 100% | 100% | 92% | 100% |
| Total | 40 | 92% | 82.5% | 82.5% | | 90.0% | 92.5% | 92.5% | 95.0% | 97.5% | 100.0% |
| Ave for both light levels | | | 82.5% | | | 91.3% | | 93.8% | | 98.8% | |
| Ave. Reduction Percentage (Using Low S/P as base) | | | 14.3% | 11.7% | | 13.6% | 15.1% | 20.7% | 25.1% | 27.3% | 27.9% |
| Ave for both light levels | | | 13.0% | | | 14.3% | | 22.9% | | 27.6% | |

Table 2: Summary results from the Brightness Matching (BM) Test.

*FIG. 16*

LIGHTING OPTIMIZED FOR MELANOPIC VISION

CROSS REFERENCE TO RELATED APPLICATIONS

This is a Divisional Application of U.S. Ser. No. 15/382,232, filed Dec. 16, 2016, which application claims priority under 35 USC § 119 to U.S. Provisional Application No. 62/269,642 filed Dec. 18, 2015 and to U.S. Provisional Application No. 62/345,559, filed Jun. 3, 2016, all of which are incorporated by reference in their entireties.

BACKGROUND OF INVENTION

Embodiments of the present invention generally relate to systems and methods for illumination. In particular, embodiments of the present invention relate to systems and methods for improving perceived brightness of lighting.

Terms Used

Many terms are used in this document which are not well-known in general, but are well-known in the lighting industry to those having ordinary skill in the art. Some included terms are less-well known or may refer to different standards and thus appear ambiguous. One such term is the "melanopic/photopic" or M/P ratio. In general, this refers to the value of light from the SPD of a particular light source which is measured and weighted according to both the melanopic and photopic effectiveness curves, respectively, wherein the melanopic value is summed and divided by the photopic value. In particular, there are at least two different metrics in use which can yield values that appear to differ in value but which differ essentially only in scaling of results. Both of these methods, the Lucas and the Wyszecki methods, which are both well-known in the industry, will be used in this application. Use of either method yields the same effective results since the difference is simply of scale in describing the M/P ratio, not a difference in the actual physical values for SPDs which are evaluated for melanopic and photopic content. The Lucas method is sourced from the 2014 Irradiance Toolbox published by Lucas et al (http://lucasgroup.lab.ls.manchesterac.uk/research/measuringmelanopicilluminance/ website accessed 2016-05-25). The Wyszecki method is discussed in the textbook "Color Science: Concepts and Methods, Quantitative Data and Formulae" $2^{nd}$ Edition by Wyszecki and Stiles, ISBN-13: 978-0471021063. Further, the term "scotopic/photopic ratio" (S/P ratio) may be found in the literature cited herein; when not differentiated from M/P ratio, it may be understood to provide very similar, though not technically identical, results, since the scotopic sensitivity curve which peaks at 507 nm is very close (though again, not identical) to the melanopic sensitivity curve which peaks at 490 nm and since the scotopic sensitivity curve is better known in the industry. Refer to FIG. 7B for a representation of the melanopic, scotopic, and photopic sensitivity curves.

References

The following documents are included by reference and incorporated in their entireties:

Schlesselman et al, *Brightness judgments in a simulated sports field correlate with the S/P value of light sources* (hereinafter cited as IES #1) (reproduced infra.).

Schlesselman et al, *Brightness matching determines the trade-off between S/P values and illuminance level* (hereinafter cited as IES #2) (reproduced infra.).

Schutz, Jason T., "Metamer Optimization" Unpublished Paper, Musco Sports Lighting, Oskaloosa Iowa 2015, Jun. 2, 2016.

Boxler, Larry, "Color Temperature and Sports Vision," Unpublished Paper, Musco Sports Lighting, Oskaloosa Iowa 2015 (also attached as FIG. 2A-P.

U.S. patent application Ser. No. 14/955,378 filed Dec. 1, 2015.

Provisional Application No. 62/269,642 filed Dec. 18, 2015.

U.S. Provisional Application No. 62/345,559 filed Jun. 3, 2016.

Berman, S. M. The Reengineering of Lighting Photometry, July 1995, Lawrence Berkeley National Laboratory Berkeley, Calif.; downloaded 12/14/2016 from https://gaia.lbl.gov/btech/papers/42327.pdf (hereinafter Berman 1995).

Zollers, M. "Phosphor Modeling in LightTools" 2011, Synopsys Inc., 700 East Middlefield Road, Mountain View, Calif. 94043, downloaded from https://optics.synopsys.com/lighttools/pdfs/ModelingPhosphorsInLightTools.pdf on Dec. 14, 2016.

Hsu et al, "Selecting Conversion Phosphors for White Light-Emitting Diodes Package by Generalized Reduced Gradient Method in Dispensing Application," 2015, Green Energy and Environment Research Laboratories, Chutung, Hsinchu, 31040, Taiwan, downloaded from http://www.nusod.org/2015/nusod15_paper46.pdf on Dec. 14, 2016

"What is the LED R9 Value? A new color quality terminology" available from www.candleray.com; downloaded from http://www.candleray.com/resources/led-lighting/new-color-quality-terminology-led-r9-value on Dec. 14, 2016.

Lucas, Robert J. et al. "Measuring and Using Light in the Melanopsin Age." *Trends in neurosciences* 37.1 (2014): 1-9. PMC. Web. 14 Dec. 2016.

"LED Color Mixing: Basics and Background" by CREE; downloaded from http://www.cree.com/~/media/Files/Cree/LED-Components-and-Modules/XLamp/XLamp-Application-Notes/LED_colormixing.pdf on 12/17/2015 (describes LED colorimetry and binning in great detail).

"Understand color science to maximize success with LEDs (MAGAZINE)" was downloaded from http://www.ledsmagazine.com/articles/2012/05/understand-color-science-to-maximize-success-with-leds-magazine.html on 12/17/2015.

In the lighting industry, several factors are important for overall desirability for a given lighting application such as sports field or wide area lighting. These factors include, among others, consideration of such concepts as brightness, human perception of brightness, color rendering and metrics for color rendering, color temperature/correlated color temperature, and spectral power distribution.

Color Metrics

As is well-known in the industry, light can be evaluated using various color metrics, such as Color Rendering Index (CRI), Television Lighting Consistency Index (TLCI), and TM-30 which is based on the Illuminating Engineering Society (IES) Technical Memorandum TM-30-15. These standards provide the industry with metrics for suitability of light and light sources for a particular purpose, such as for broadcasting. In general, it is desirable to have a "high" or "favorable" rating or measured value in accordance with these standards for lighting; thus new light sources and new methods for lighting will be evaluated in the industry for their ratings or measured values. For an example of the CRI rating, low pressure sodium lights, which emit at monochromatic light at about 589 nm wavelength, and which are generally considered to have an undesirably light quality, have a "0" CRI rating, since no colors are rendered other than around 589 nm. Typical fluorescent lamps can range from about 50 CRI (fairly poor) to up to about 90 CRI (quite good) for tri-phosphor types. In general terms, incandescent lamps are essentially the standard for CRI so generally by definition, they will have a CRI of 100. Information on these standards and their use is readily available in the industry.

A further color metric is the "CRI R9" metric (or sometimes just "R9"), which in comparison to the CRI metric, provides a better metric of "saturated red" which is considered important in some contexts.

U.S. Provisional Applications No. 62/269,642 and No. 62/345,559 further provide extensive background on the concepts of brightness and perception of brightness to the present application. Light having a higher melanopic content, as measured by e. g. the M/P or S/P ratio (explained further below), and in IES #1 and IES #2, is perceived of as brighter than light having a lower melanopic content. Thus, lighting that is designed to incorporate high melanopic content that also provides or improves upon benefits of effectiveness and quality as previously described would be very desirable in the industry based on at least the criteria discussed above. For example, as discussed in IES #2, a "25% light level reduction in a lighted athletic field employing a typical MH source of S/P=1.4" [as measured by the "Lucas method", see below] when replaced by an LED source of S/P=2.4 while maintaining the same brightness perception is possible. This would be perceived of as very valuable in the industry.

Correlated Color Temperature (CCT) and Metamerism

As is well-known in the industry, a "black body radiator" (such as e.g. a tungsten filament in an incandescent light) heated to a specific temperature (i.e. its "color temperature" measured in Kelvins) will emit visible light having a specific spectral power distribution (SPD)—see FIG. 7A. Correlated Color Temperature (CCT) basically describes a light source in terms of its visual similarity to the light from a black body heated to the corresponding color temperature; it is used to describe and compare "white" light sources. In general, if two light sources have the same CCT, they appear the same to an observer. It is also well-known in the industry that light at a given CCT, also measured in Kelvin, has an SPD that can be measured, and still further, given the SPD of a light source, the CCT may be calculated using methods well-known in the industry.

The study of human vision has led to the industry understanding that the human eye has receptor cells, known as "cones" which respond to the cumulative energy from a broad range of wavelengths. These cones are generally associated with the colors red, green, and blue, and produce a receptor response known as the "tri-stimulus" response which translates to the perception of a color in the human visual system. Further, since the human eye does not have individual receptors which register discrete wavelengths, it is known in the industry that different combinations of light across all wavelengths (i.e. different SPDs) can produce an equivalent tri-stimulus response known as a "metamer." "Metamerism" therefore is generally the existence of light with differing SPD having a very similar or identical CCT and a normal human visual perception that they are the same color. FIG. 1A illustrates in graphic form SPDs for three different sources of white light, where the X axis represents the specific wavelength in nm, and the Y axis represents the relative power of the spectral components, scaled to normalize the highest value as 100%. The three SPDs illustrated are similar but not identical and represent three different CCTs. FIGS. 1B and 1C similarly show a graphic representation of the SPD of two different white light sources that are metameric. This means that their calculated CCTs are approximately the same in spite of their differing SPD. Note that FIG. 1C shows a sharp peak at 450 nm and a pronounced trough just below 500 nm, in comparison with FIG. 1B which shows approximately 50% less power at 450 nm.

Brightness, Perceived Brightness, and Melanopsin Receptors

In the lighting industry, several factors are important for overall desirability for a given lighting application such as sports field or wide area lighting. "Brightness" of light as measured in various ways is well-known in the lighting industry as a very important aspect of lighting design and installation. The concept of "perception of brightness" as now understood to be related to the function of "melanopsin receptor response" in the human eye is relatively new to the industry. These melanopsin receptors are believed to function differently than, and more or less in addition to, the functions of the "cone receptors" of the human eye that are associated with color perception.

Until recently, it was thought that "brightness" was sensed entirely or almost entirely by these cone receptors at photopic levels; however now there is empirical evidence that these melanopsin receptors play a very important part in human perception of brightness. Their function—at least in terms of human perception of brightness—has been discussed in several recent papers which are cited in U.S. Provisional Application No. 62/269,642, to which the present application claims priority, and which is incorporated in its entirety by reference herein. Papers by Schlesselman et al (IES #1, IES #2) which were incorporated in U.S. 62/269,642 and which are also included by reference herein in their entirety show that a "measured 25% light level reduction" with "no decrease in perceived brightness" is considered possible. Thus, when it is understood there are additional receptor mechanisms, it may be understood, and the reader may appreciate as will be further explained herein, that the metamers represented by FIGS. 1B and 1C may have different perceived brightness levels for a given measured luminosity. Thus, one metamer may be selected over another to provide the desired CCT and improved brightness relative the other.

As previously noted, any decrease in measured light level, much more a "measured 25% light level reduction" with no decrease in perceived brightness, and which takes advantage of the principle of metamerism to provide a lighting quality that is similar, identical to, or even improved over existing light sources would be considered extremely desirable in the lighting industry.

Thus there is room for improvement in the art.

SUMMARY OF INVENTION

It is therefore a principle object, feature, advantage, or aspect of the present invention to improve over the state of the art and/or address problems, issues, or deficiencies in the art.

An embodiment according to aspects of the invention comprises a method of illumination comprising comparing metamers at a known and similar CCT with at least one metamer having a higher M/P or S/P ratio; selecting at least one of said metamers for improved perceived brightness; evaluating the selected metamer(s) for desired CCT and acceptable CRI; manufacturing a lighting apparatus which emits light of a given CCT having increased melanopic content compared to one or more extant metameric variations of the same or similar CCT; wherein said light has an acceptable CRI.

Another aspect according to the invention comprises producing LED lighting with high melanopic content, wherein the relative content comprises above approximately 50% within 5° of 490 nm and above approximately 25% within 10° below and 15° above 490 nm. In one embodiment the lighting comprises an M/P ratio on the order of 1.2.

Mother aspect according to the invention comprises producing LED lighting with high melanopic content, wherein the lighting comprises values of CCT 17,000K; CRI 74, R9 69; M/P Wyszecki 9.0, Lucas 1.78; TLCI 77.

Another aspect according to the invention comprises producing LED lighting with high melanopic content, wherein the lighting comprises values of CCT 5,700K; CRI 82, R9 59; M/P Wyszecki 6.0, Lucas 1.19; TLCI 75.

Mother aspect according to the invention comprises producing LED lighting with high melanopic content, wherein the lighting comprises values of CCT 17,000K; CRI 74, R9 69; S/P 3.57; TLCI 77.

In another aspect, the invention relates to an apparatus for improved illumination with improved brightness comprising a solid state light source having an SPD output which has similar CCT compared to existing lighting but which is perceived of as significantly brighter for the same power input, or requires less power input for the same perceived brightness, by providing light which is a metamer of the existing lighting and which has a higher S/P or M/P ratio than the existing lighting.

In another aspect, the invention relates to a method of improved perceived brightness and/or visual acuity for observers of a scene illuminated with a plurality of light sources comprising: providing a target area to illuminate; designing illumination for the target area with light of at least relatively high melanopic content, wherein (1) the light of relatively high melanopic content is determined by quantifying a scotopic/photopic ratio (S/P) or melanopic/photopic ratio (M/P); and (2) selecting a quantified S/P or M/P ratio which (i) uses a high color temperature to increase the S/P or M/P ratio; while (ii) maintaining a predetermined acceptable color temperature; and implementing the designed illumination at the scene with a lighting system comprising a plurality of light sources operated collectively according to the designed illumination. The method can allow illumination which meets a given lighting standard relative to intensity and/or uniformity with lower energy usage and/or fewer light sources than illumination meeting the lighting standard but of lower melanopic content because of higher perceived brightness and/or visual acuity of the designed illumination.

Mother aspect of the invention relates to a method of improved lighting of a scene or target with a plurality of light sources comprising: determining an illumination color or CCT and intensity for the scene or target; installing the plurality of light sources to direct light from them to illuminate the scene or target; coordinating the operating characteristics of individual light sources of the plurality of light sources to elicit an effective amount of perceived increased brightness and/or visual acuity by normal human observers of the lighting from not only cones but other optical receptors relevant to pupil response of the observer to the light.

Another aspect of the invention relates to a method of operating an LED lighting system capable of high melanopic content lighting comprising: selecting desired color properties of the LED lighting system based, at least in part, on the general purpose of the lighting or a task to be performed thereunder; selecting a high melanopic content LED at a specified correlated color temperature wherein: the correlated color temperature is based, at least in part, on the task or general purpose; calculating equal perceived brightness of the high melanopic content LED; and varying the operating conditions of the high melanopic content LED and a low melanopic content LED at a constant perceived brightness in accordance with an operating profile.

Another aspect of the invention relates to an LED lighting fixture comprising: a thermally conductive housing; with one or more subsets of LEDs; a first subset of LEDs in said housing having a first melanopic content and SPD; a second subset of LEDs in said housing having a second melanopic content and SPD; and electrical means to power said LEDs according to one or more of the methods described above or herein. The electrical means can take many forms. One non-limiting example is a single controller adapted to adjust the power to the first and second subset of LEDs according to an operating profile wherein the profile is determined, at least in part, on physiological/biological benefits associated with the melanopic content of the first and second subsets of LEDs. Another example is a controller having two or more control means adapted to adjust the power to the first and second subset of LEDs to create a composite beam from said lighting fixture having a specific and high melanopic content at a specific CCT. In one example the CCT is on the order of 5,700K and the melanopic content as described by the M/P (Lucas) ratio is 2.0 or greater.

These and other objects, features, aspects, or advantages of the invention will become more apparent with reference to the accompanying specification and claims.

BRIEF DESCRIPTION OF THE DRAWINGS

From time-to-time in this description reference will be taken to the drawings which are identified by figure number and are summarized below.

FIG. 5 lists color weights for known sources (such as e.g. monochromatic LEDs or phosphors used with known LEDs) to create a CCT represented by the listed chromaticity coordinates.

FIGS. 8A-C illustrate SPDs for various light sources.

FIGS. 13A-I are illustrations and graphs referred to in IES #1 and IES #2.

FIG. 14 is Table 4 discussed at IES #1 in the Detailed Description of Exemplary Embodiments of the Invention.

FIG. 15 is Table 1 discussed at IES #2 in the Detailed Description of Exemplary Embodiments of the Invention.

FIG. 16 is Table 2 discussed at IES #2 in the Detailed Description of Exemplary Embodiments of the Invention.

DETAILED DESCRIPTION OF EXEMPLARY EMBODIMENTS OF THE INVENTION

A. Overview

Figure 1A:
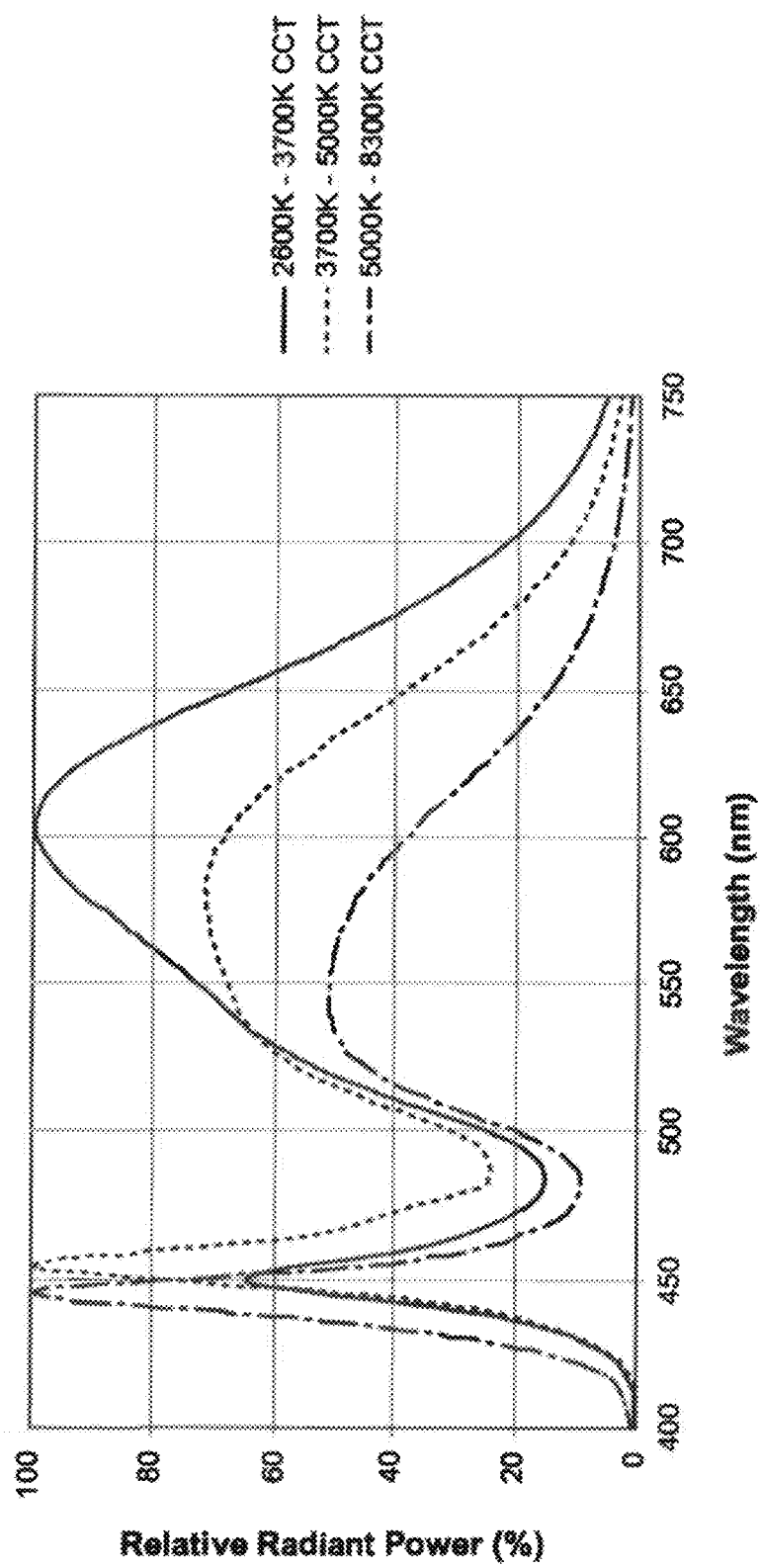
FIG. 1A illustrates typical SPDs of various sources of white light at different color temperatures.
Figure 1B:
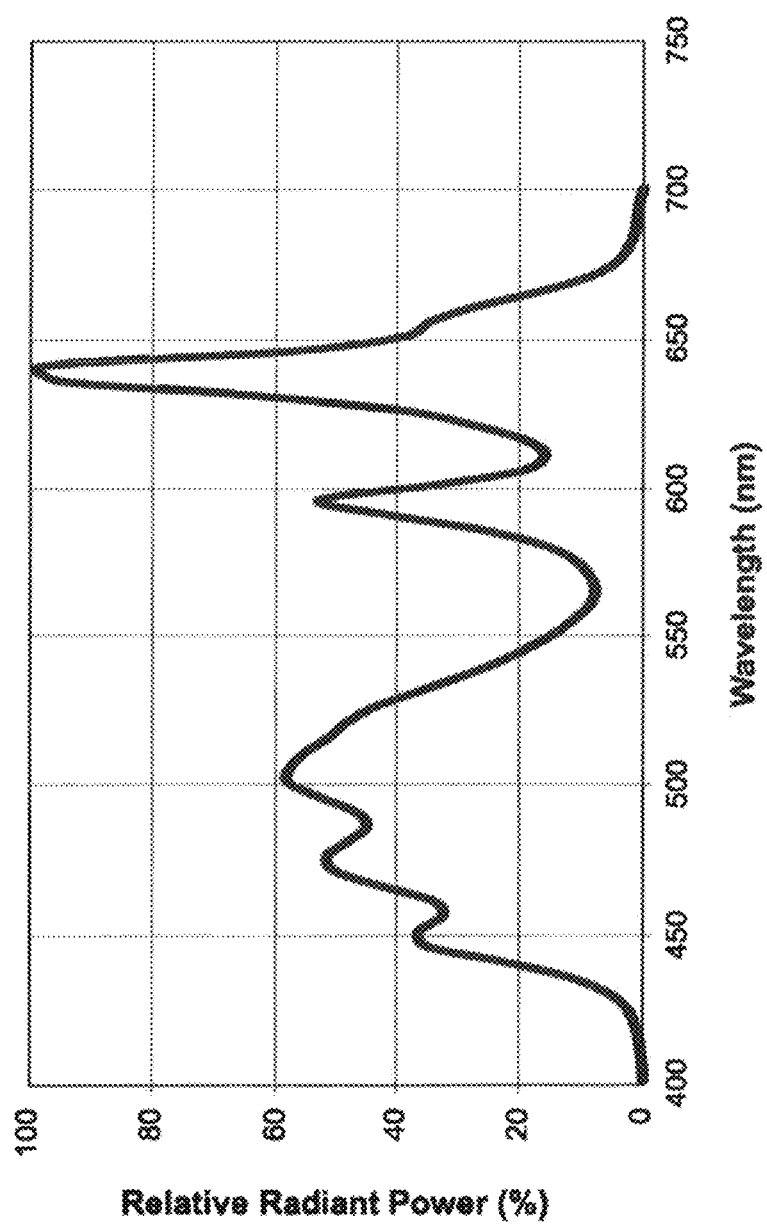
FIGS. 1B-C illustrate SPDs of light sources that are mutually metameric.
Figure 1C:
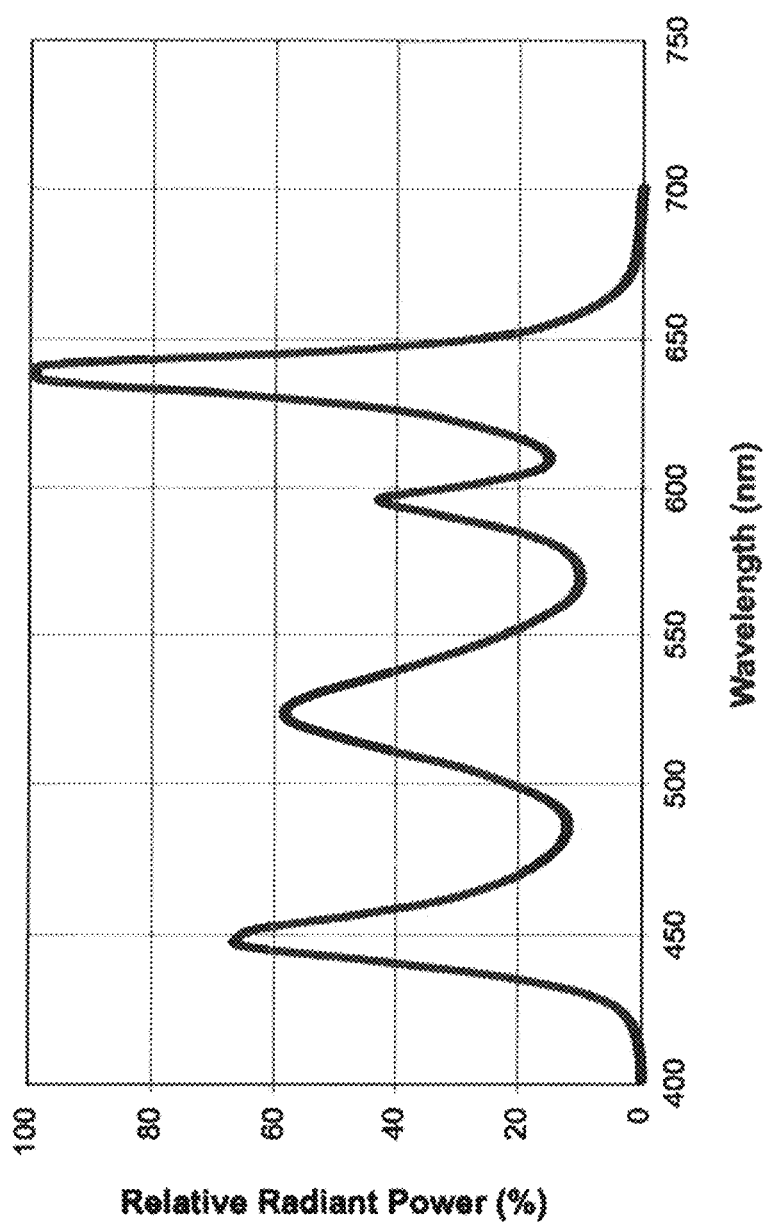

To further an understanding of the present invention, specific exemplary embodiments according to the present invention will be described in detail. Frequent mention will be made in this description to the drawings. Reference numbers will be used to indicate certain parts in the drawings. Unless otherwise stated, the same reference numbers will be used to indicate the same parts throughout the drawings.

It should again be noted that while the primary focus of this application is working with the light having a specific melanopic content as expressed by the M/P ratio, the term and concept "scotopic/photopic ratio" (S/P ratio) may be found in literature cited herein (and indeed the scotopic sensitivity curve is better known in the industry). When not differentiated from M/P ratio (or if the terms "scotopic/photopic ratio" or "S/P ratio" are used by themselves without further explanation), it should be understood that the S/P ratio provides a very similar, though not technically identical, results, since the scotopic sensitivity curve which peaks at 507 nm is very close (though again, not identical) to the melanopic sensitivity curve which peaks at 490 nm.

Figure 11A:
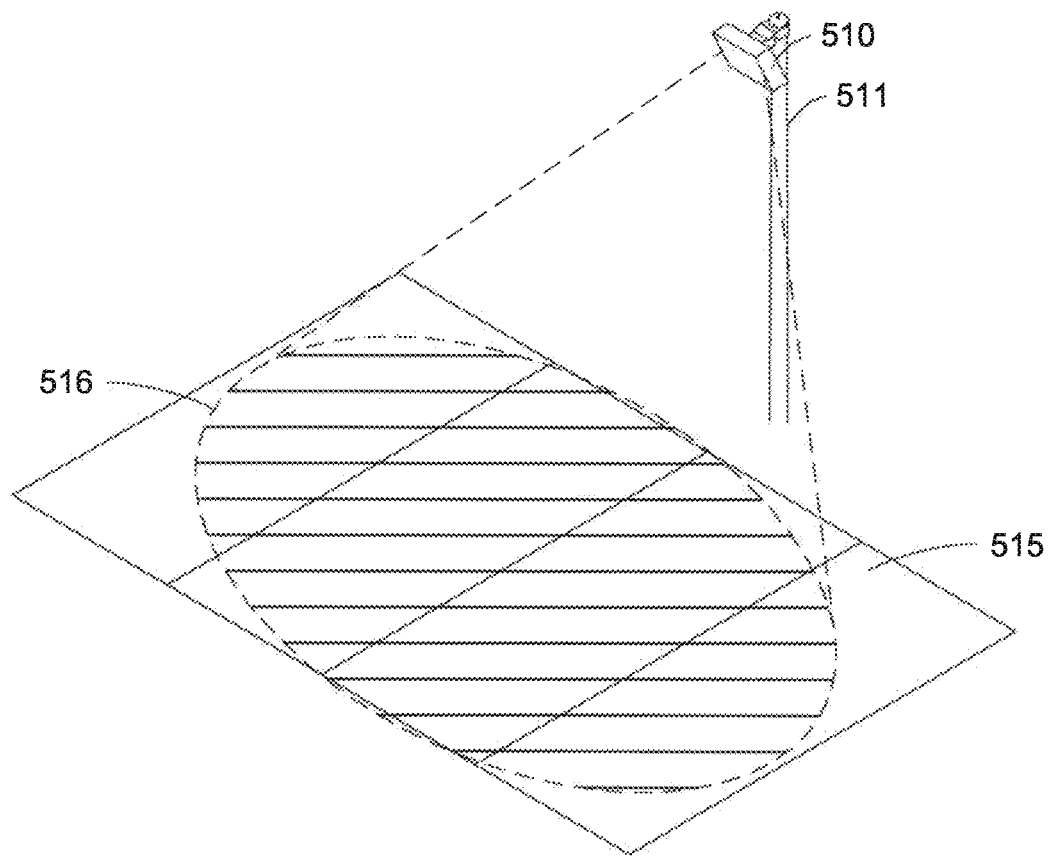
FIGS. 11A-B illustrate an apparatus for LED light output according to aspects of the invention.
Figure 11B:
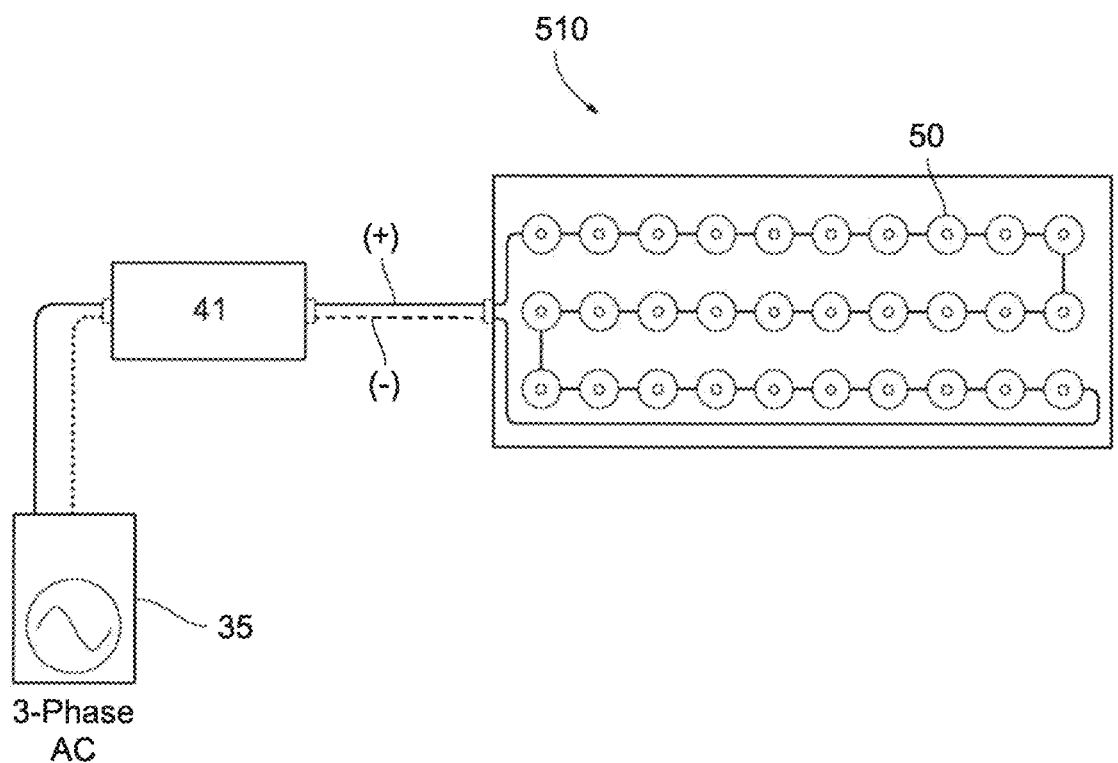

B. Embodiment 1—Apparatus for Improving Perceived Light Brightness Using High M/P Ratio Light FIGS. 11A-B show a lighting system according to aspects of the invention. Pole 511 holding LED luminaire 510 is installed at field 515 illuminating target area 516; power is distributed and conditioned by power means 35 and driver, respectively.

Multiple LEDs 50 as shown in FIG. 11B, each having the same CCT and SPD, are used to create a composite beam illuminating target area 516. This composite beam has a specified CCT and SPD and has high melanopic content as measured by an M/P ratio on the order of 1.5, 2.0, 3.0 or even higher.

In another variation, a mixture of several different kinds of LEDs 50 are used in a combination that yields a composite beam having a specified CCT and SPD and having high melanopic content as measured by an M/P ratio on the order of 1.5, 2.0, 3.0 or even higher, on a target.

LEDs 50 comprising a light source emit light having high melanopic content at a specific CCT. One such light source is illustrated by FIG. 3CC which describes a light source having a 5,700K CCT with CRI 79, CRI-R9 23, M/P 6.0, and TLCI 94. Other CCTs from e.g. 3000K to 17,000K are possible and envisioned, as described and illustrated in FIGS. 3A-3DD.

C. Embodiment 2. A Method for Creating Metamers with High Melanopic Content and Greater Perceived Brightness than Conventional LED Light Sources Note: Except as noted below, this embodiment lists and measures M/P ratios according to the "Wyszecki method" as discussed previously.

Figure 3A:
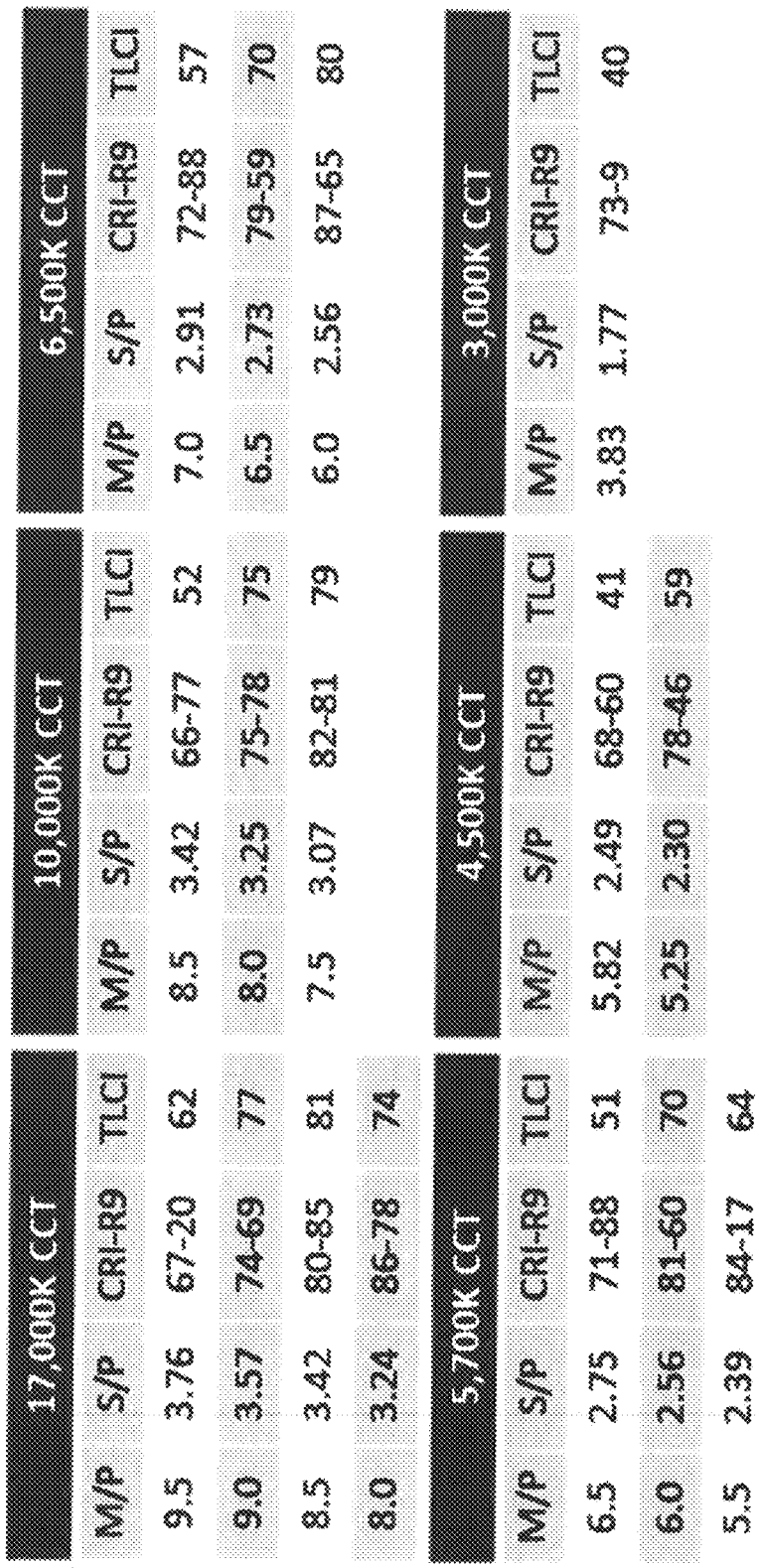
FIGS. 3A-Z and 3AA, 3BB, 3CC, and 3DD illustrate further methods according to aspects of the invention.
Figure 3E:
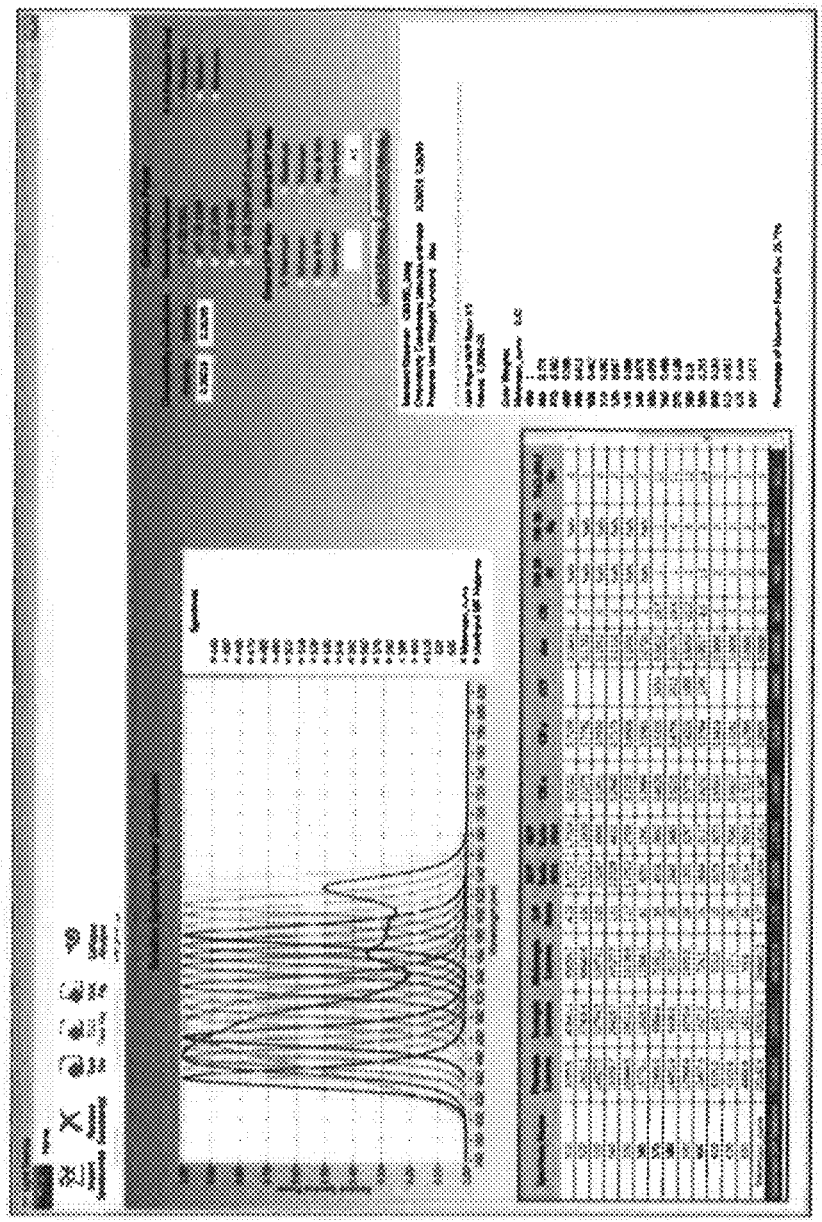
Figure 3F:
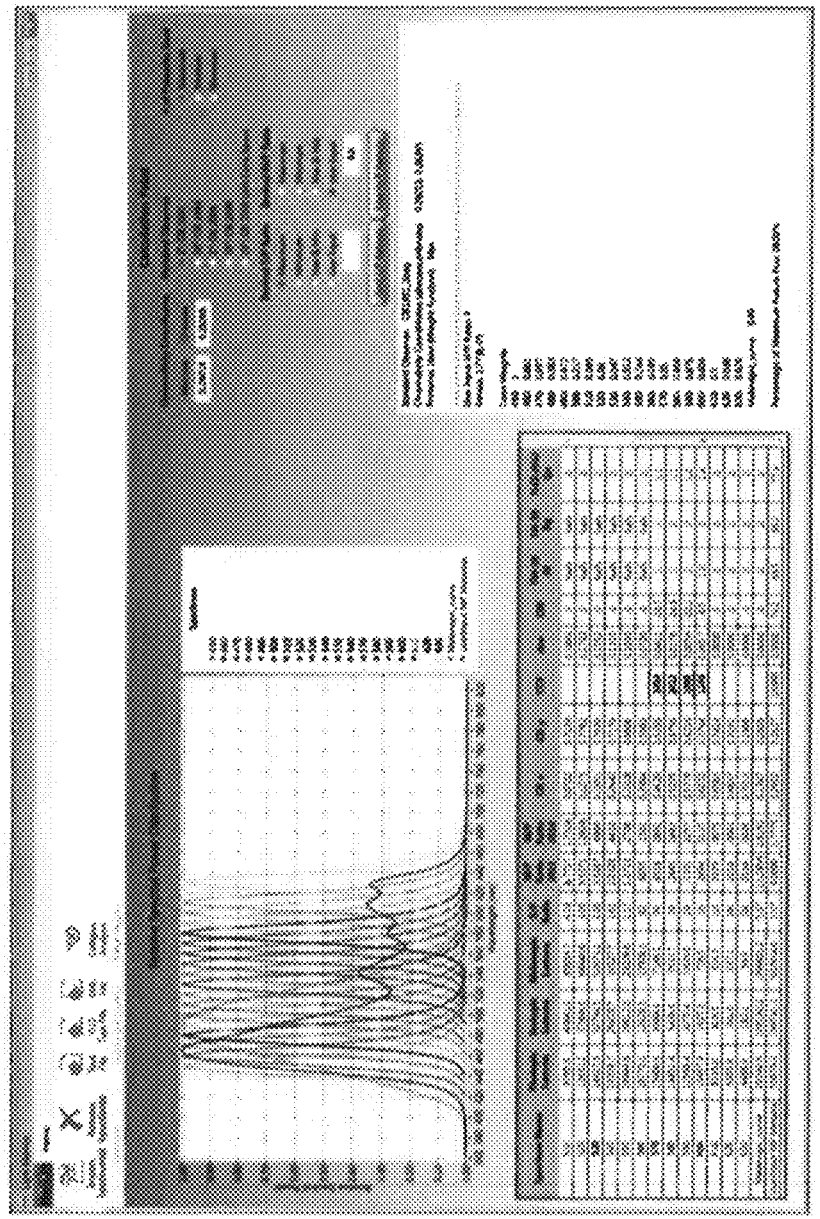
Figure 3G:
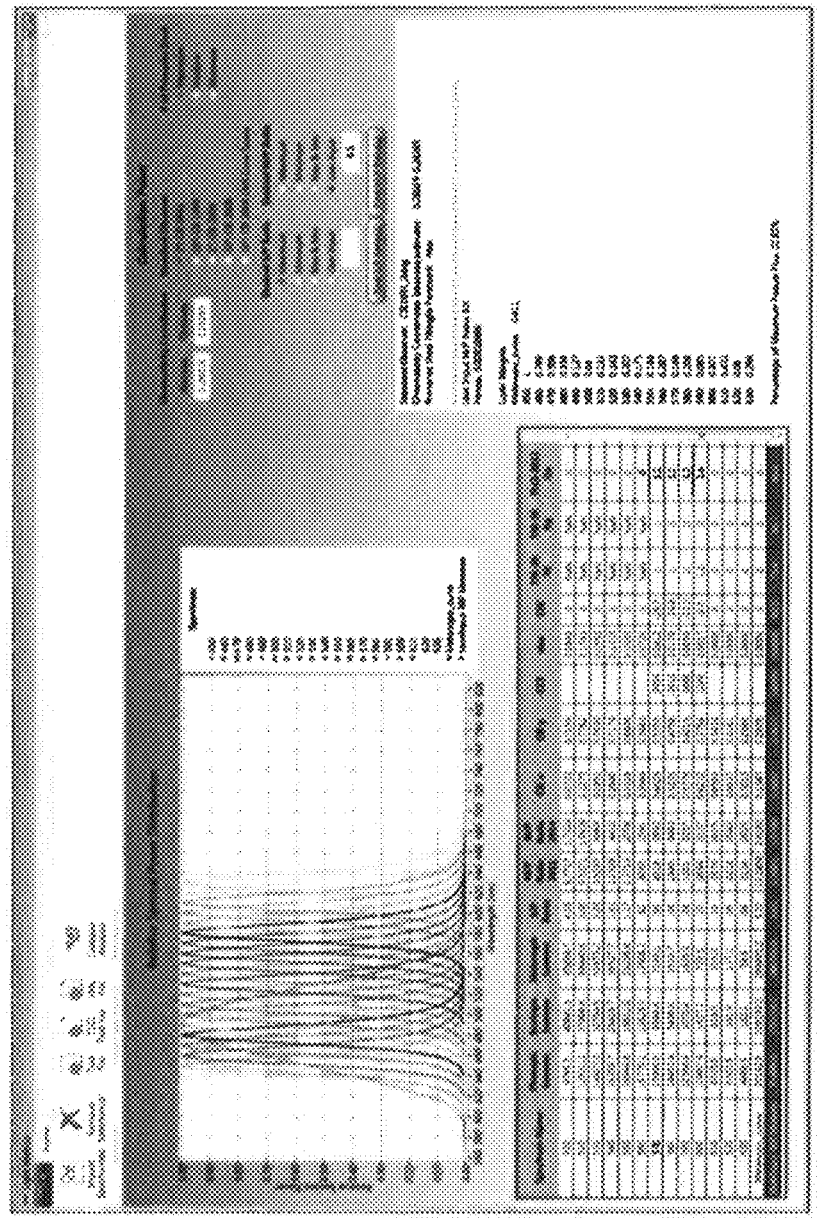
Figure 3H:
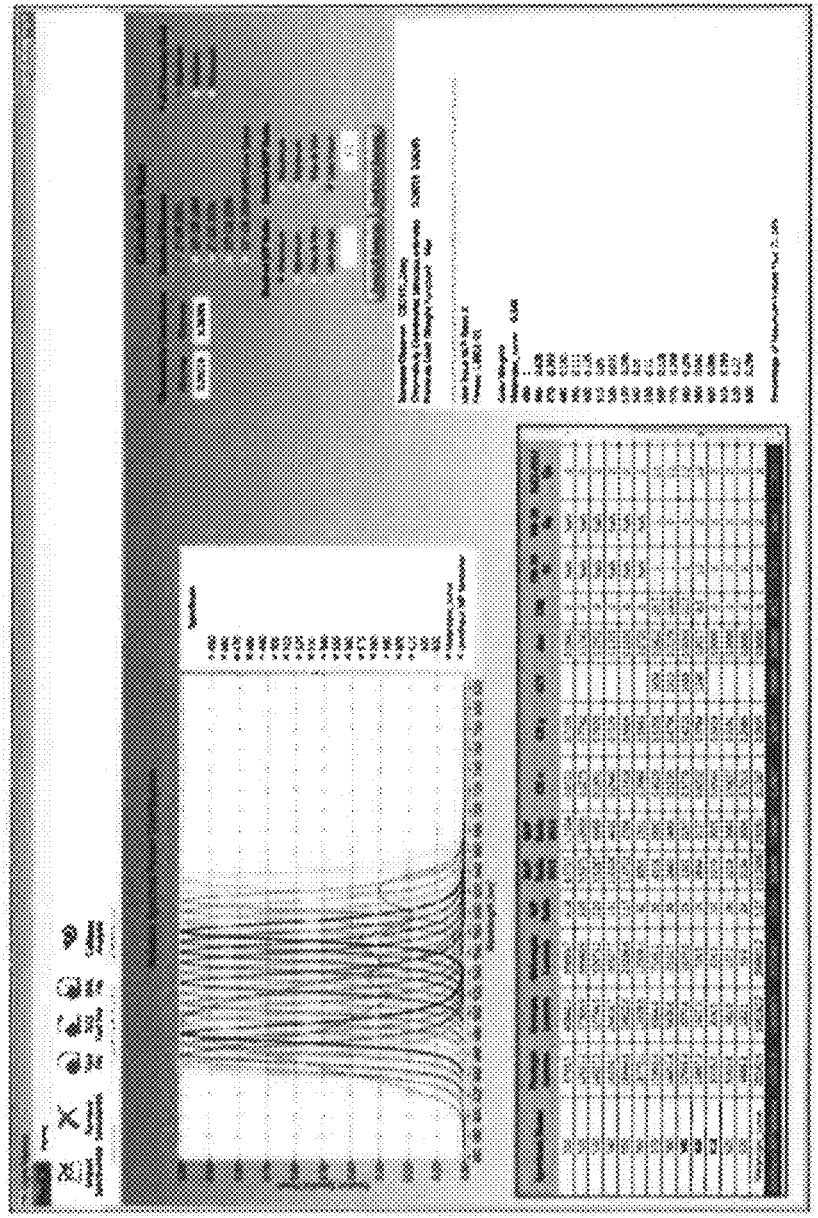
Figure 31:
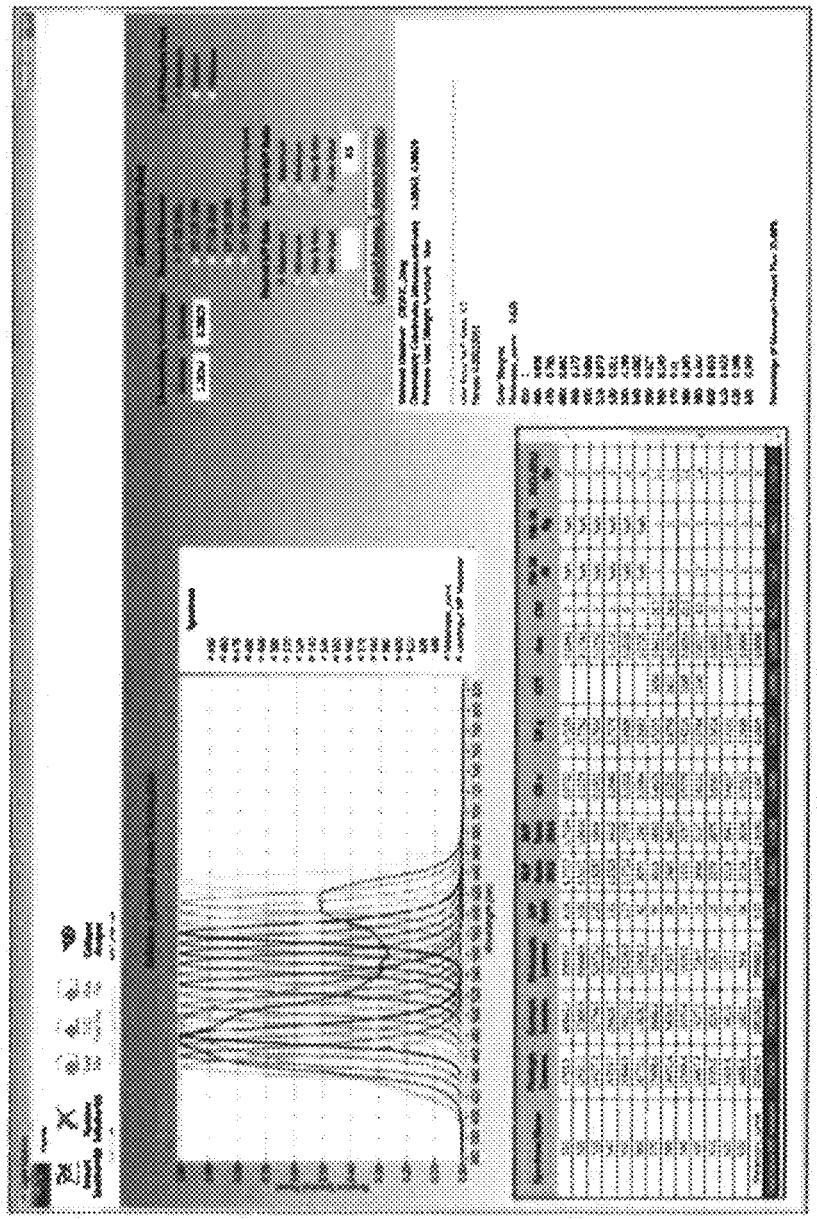
Figure 3J:
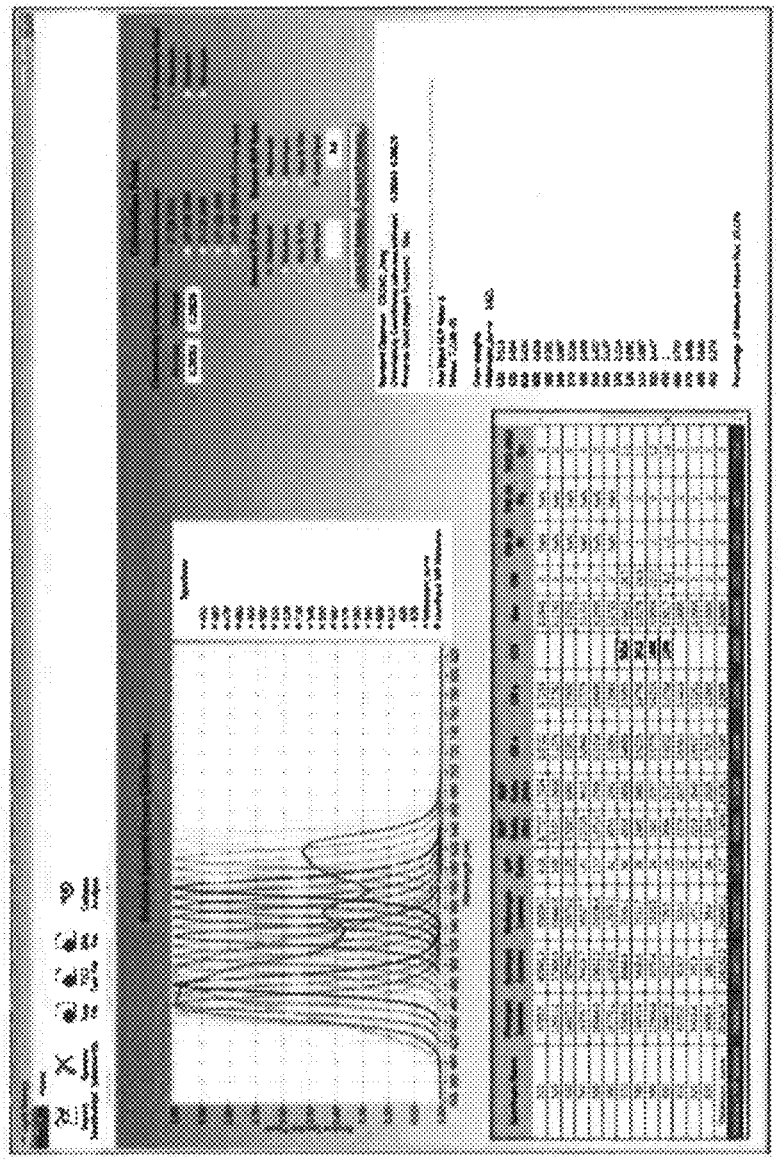
Figure 3K:
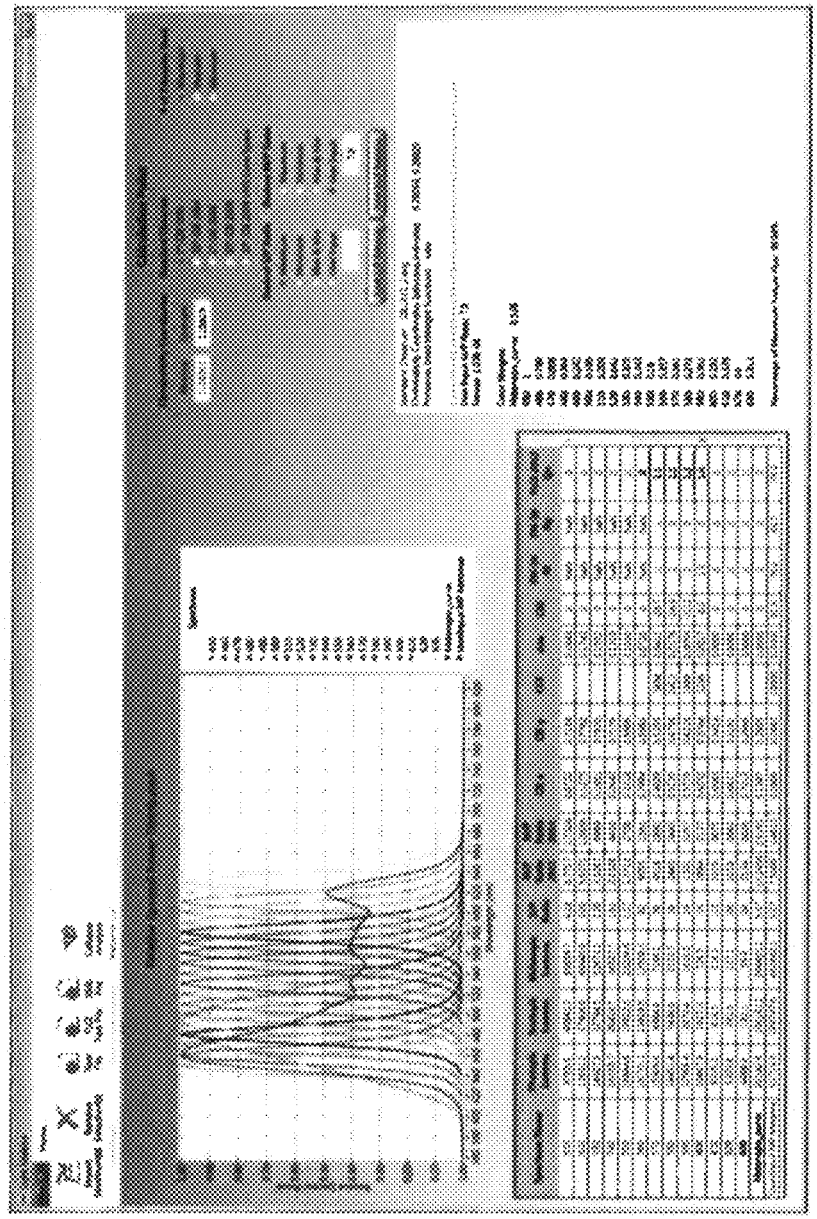
Figure 3L:
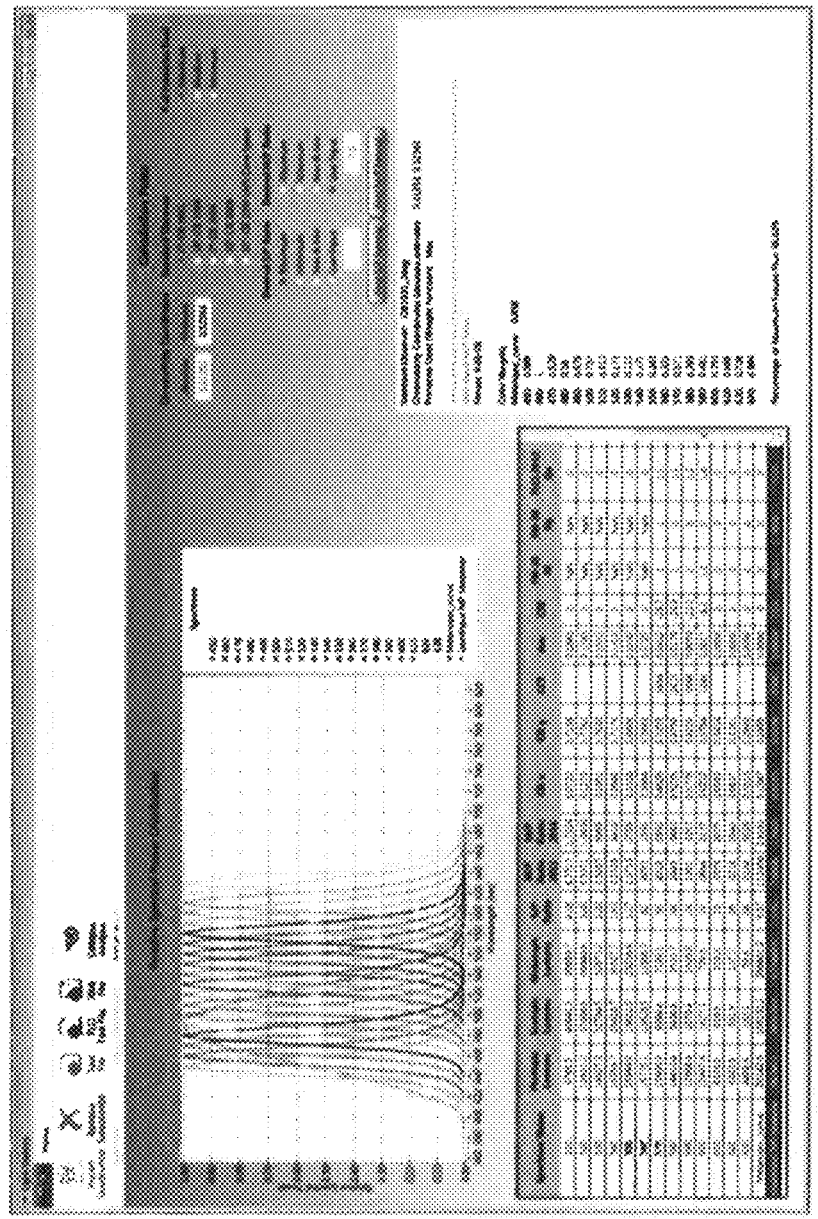
Figure 3M:
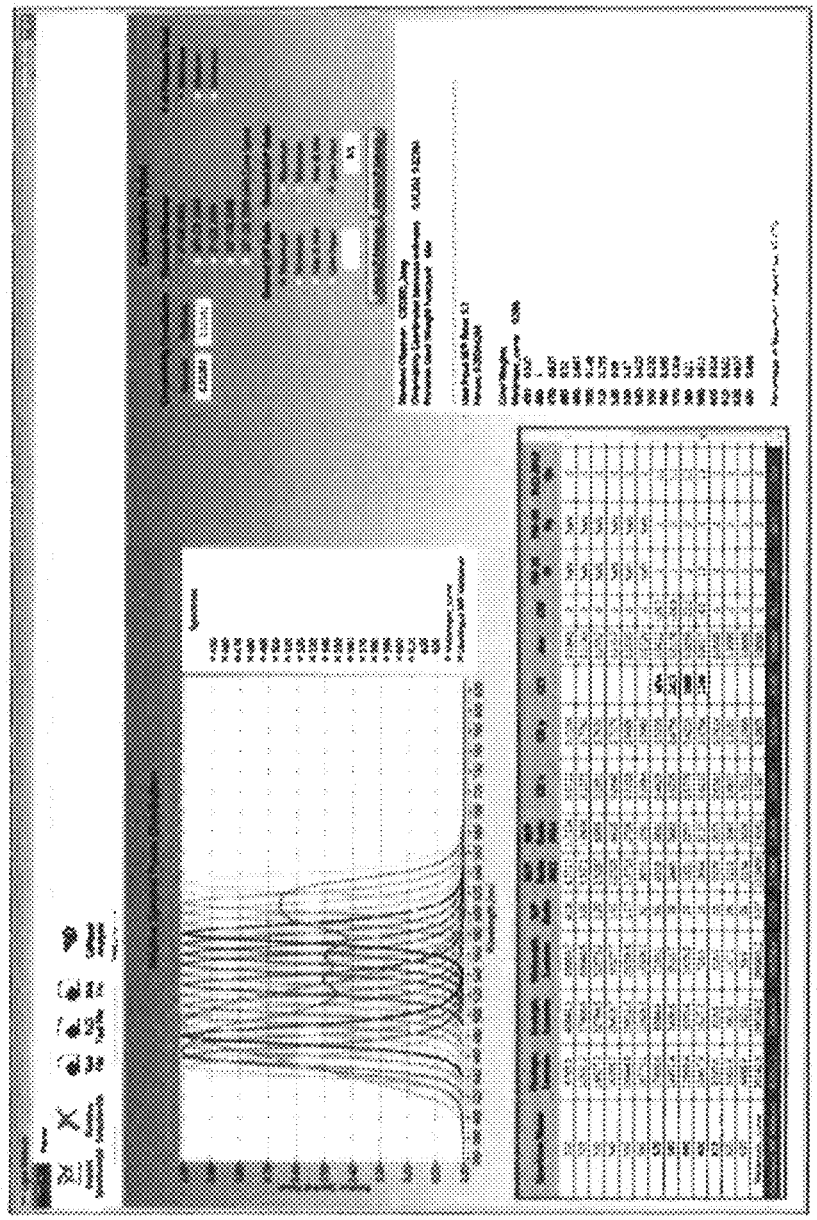
Figure 3N:
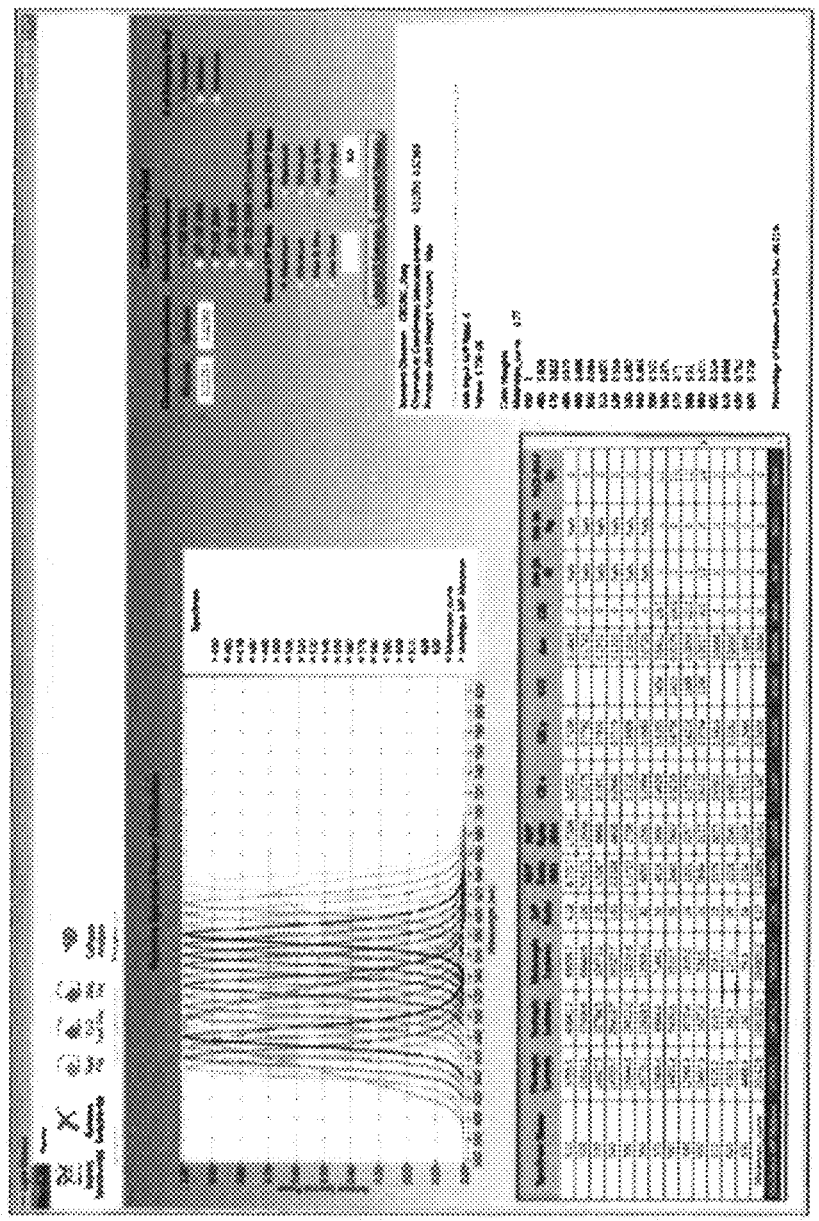
Figure 30:
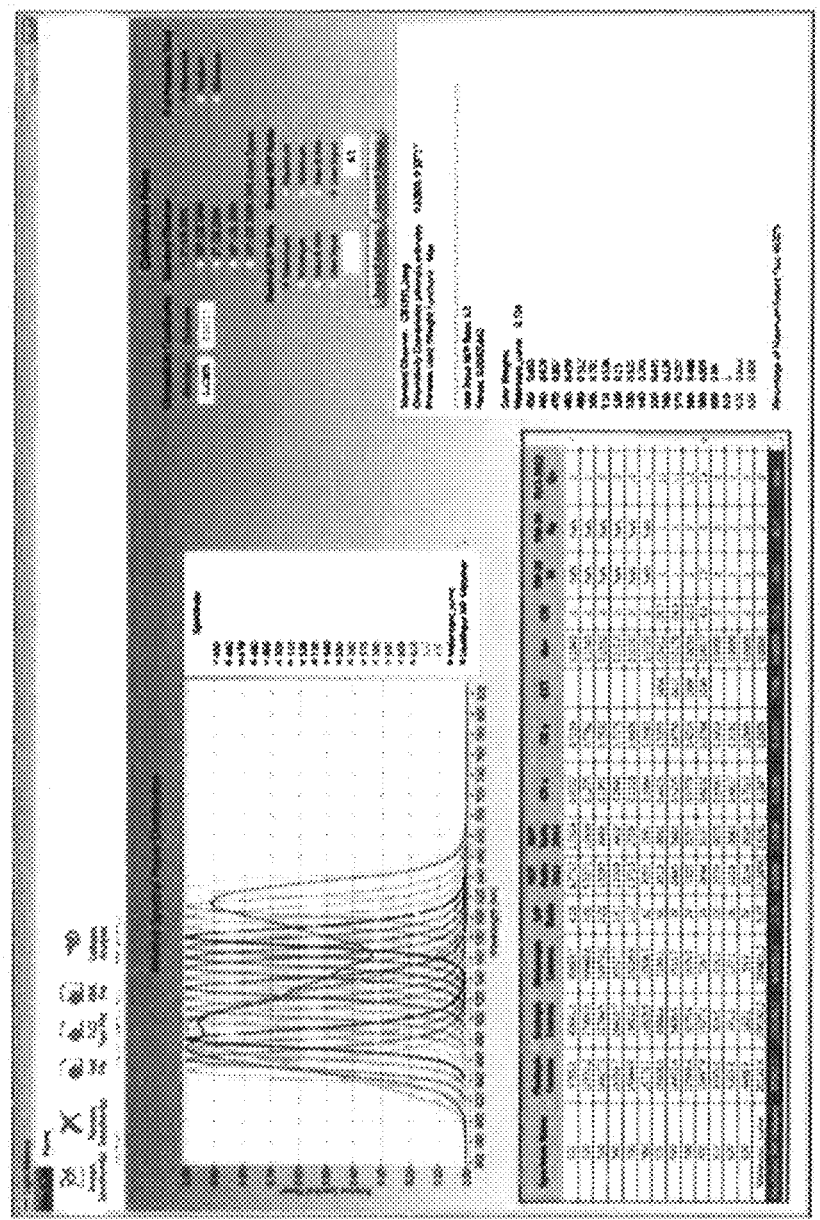
Figure 3P:
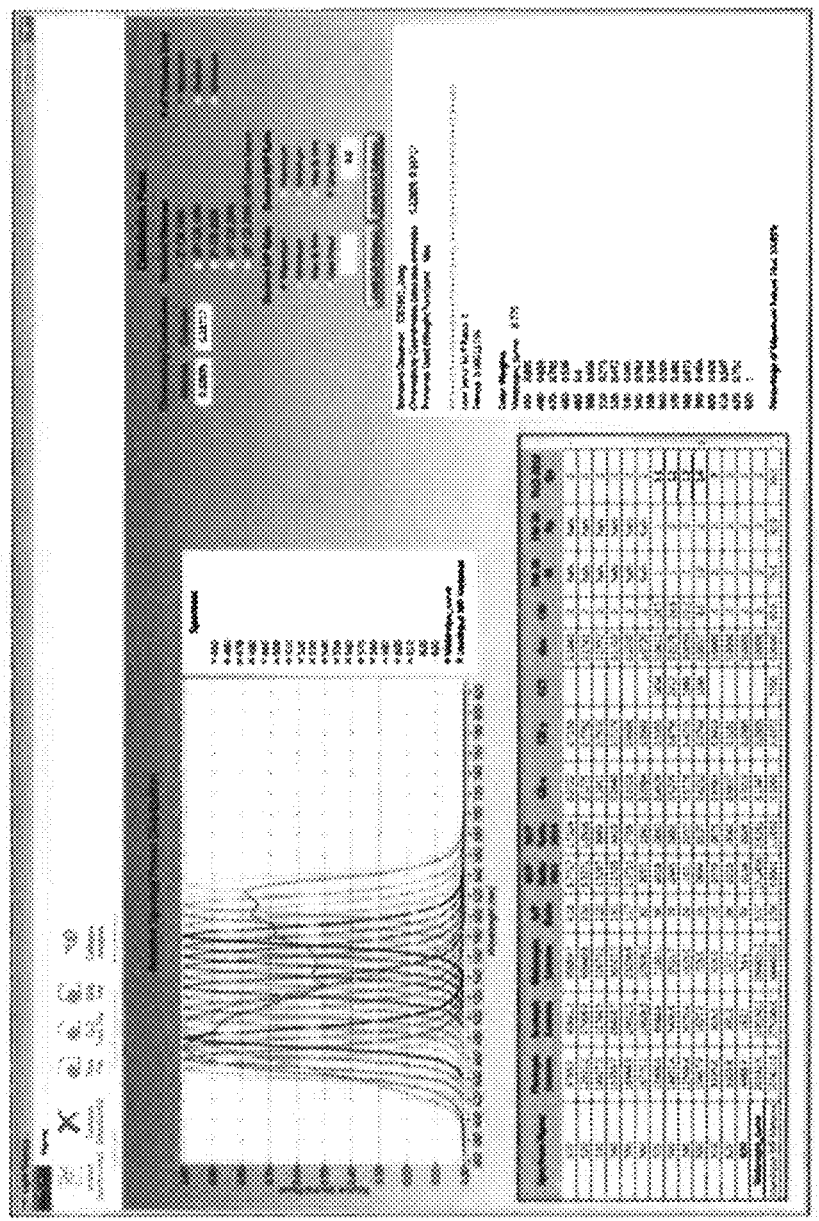
Figure 3Q:
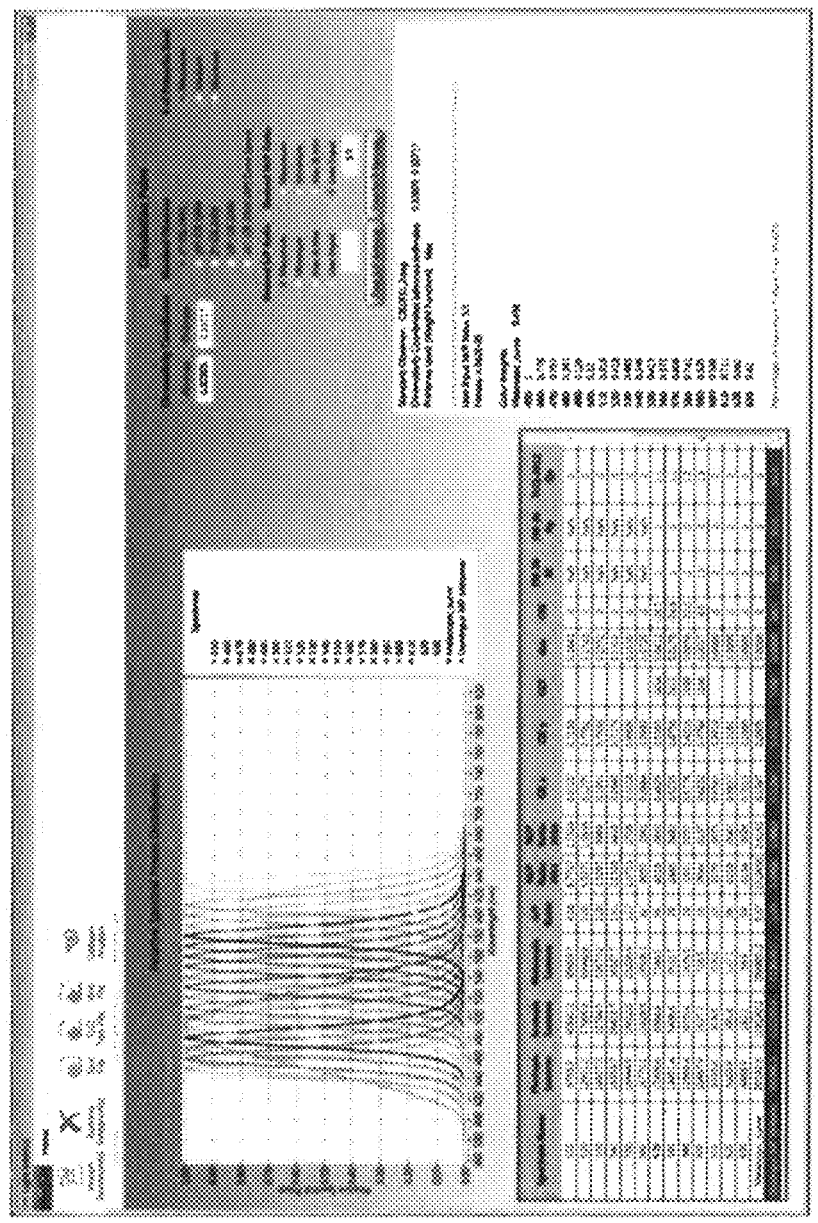
Figure 3R:
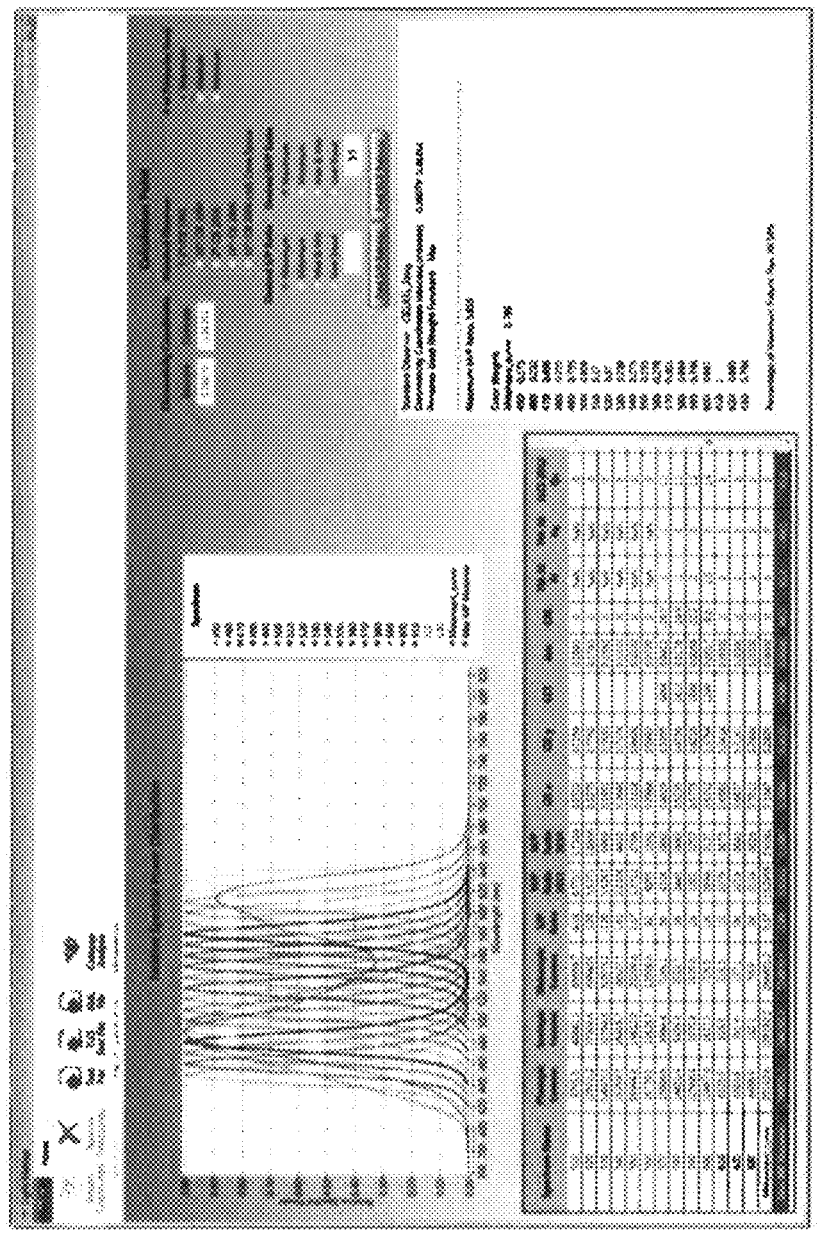
Figure 3S:
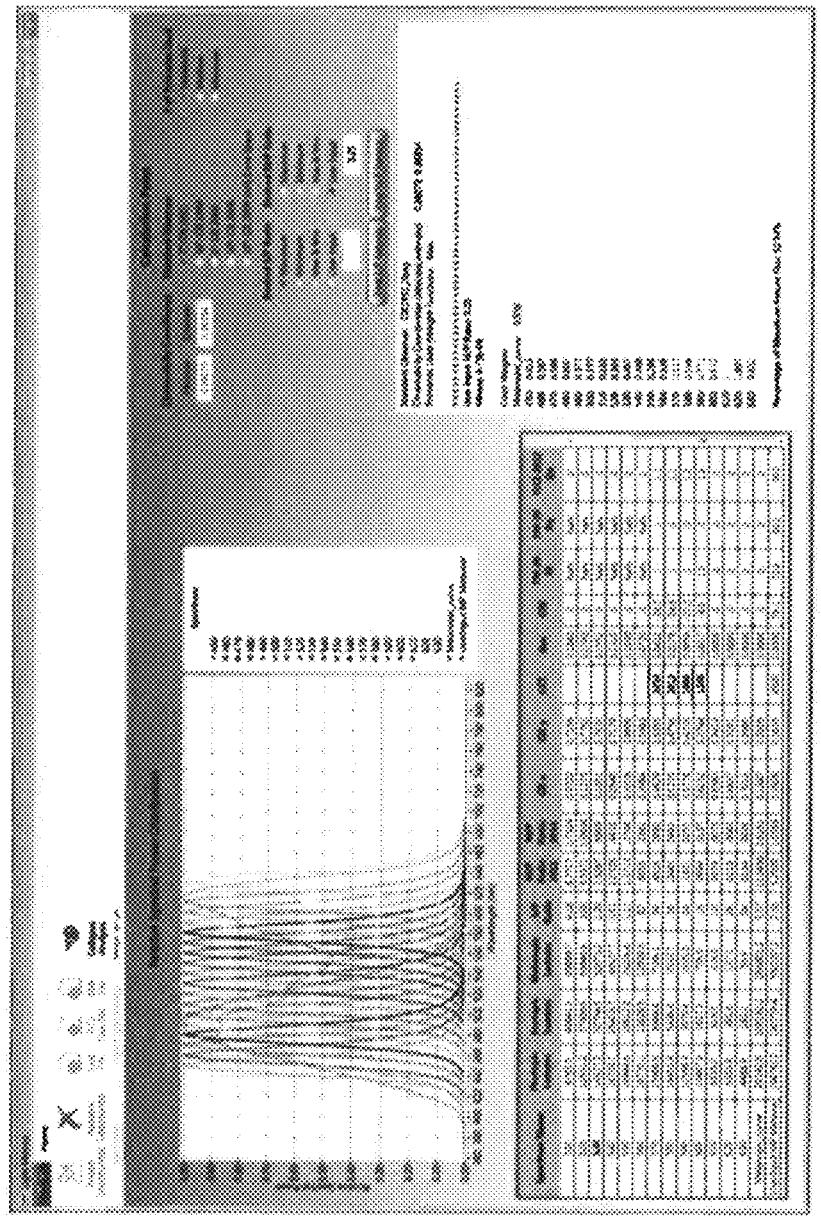
Figure 3T:
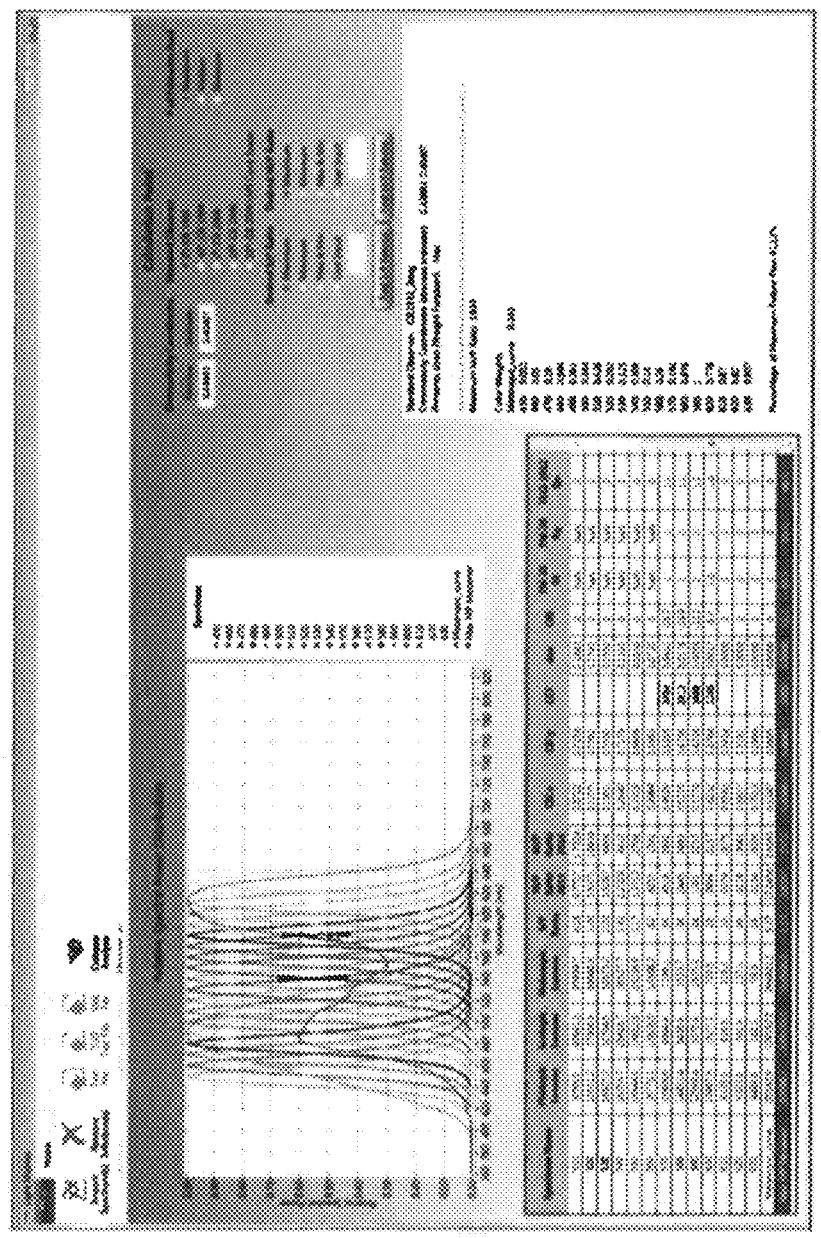
Figure 3U:
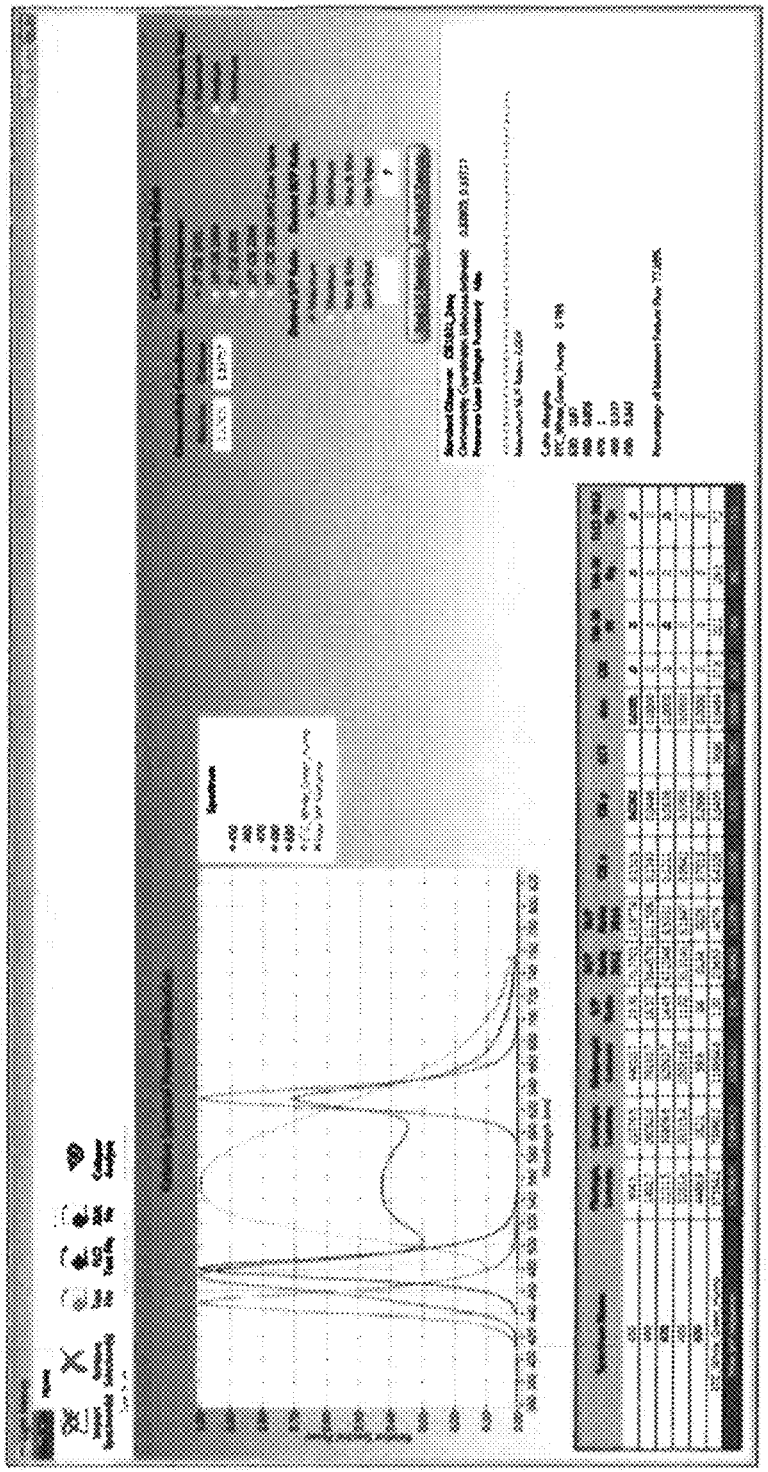
Figure 3V:
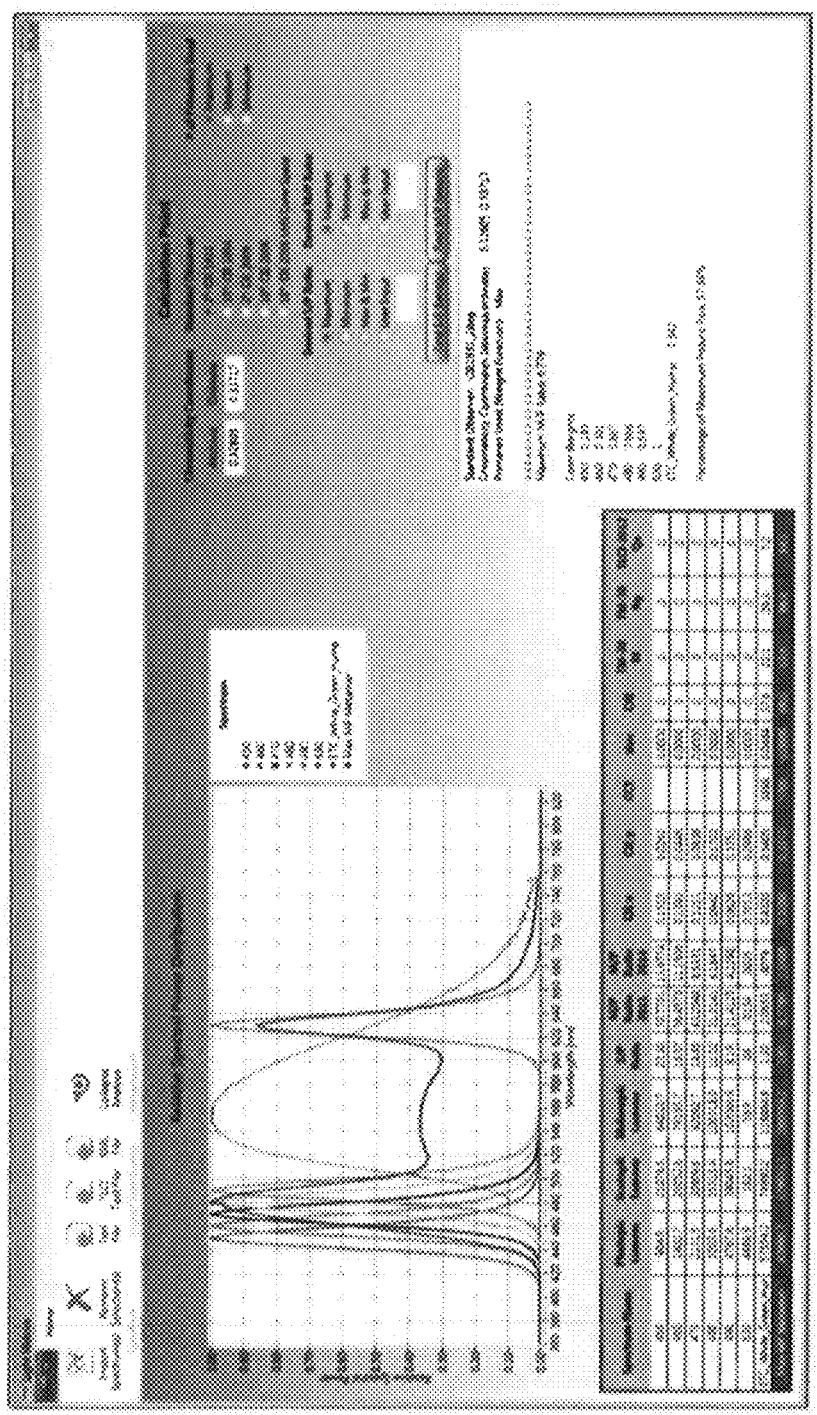
Figure 3W:
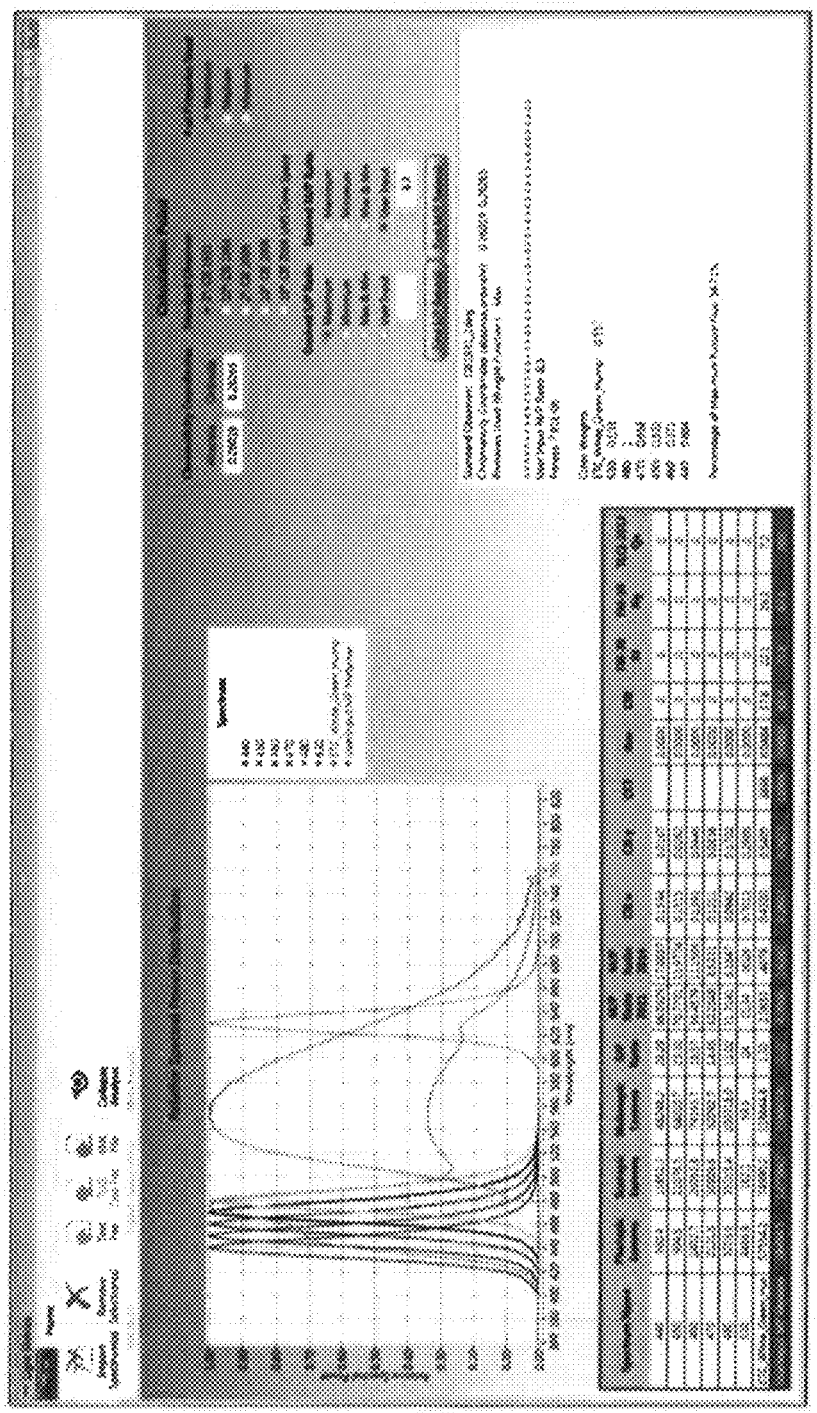
Figure 3X:
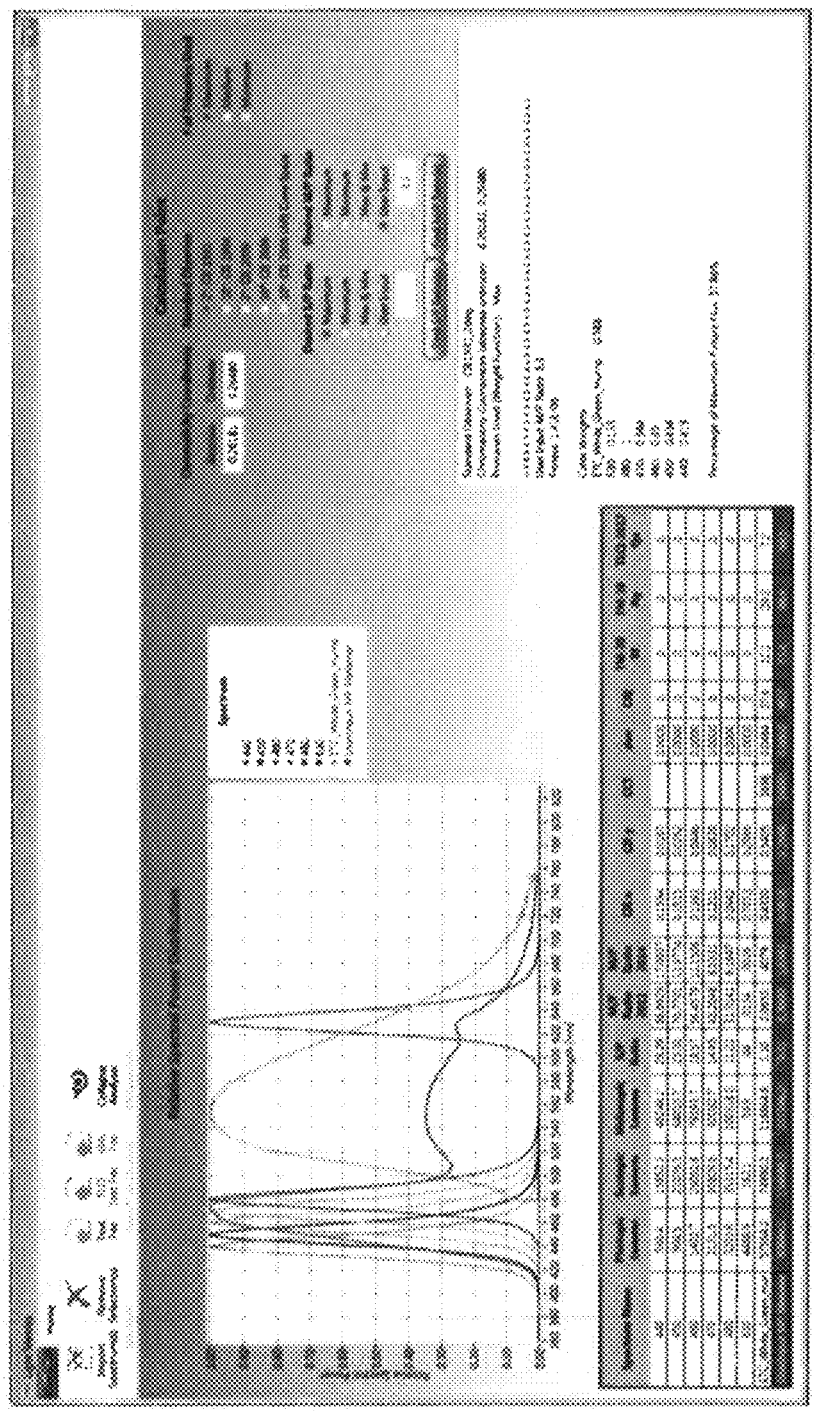
Figure 3Y:
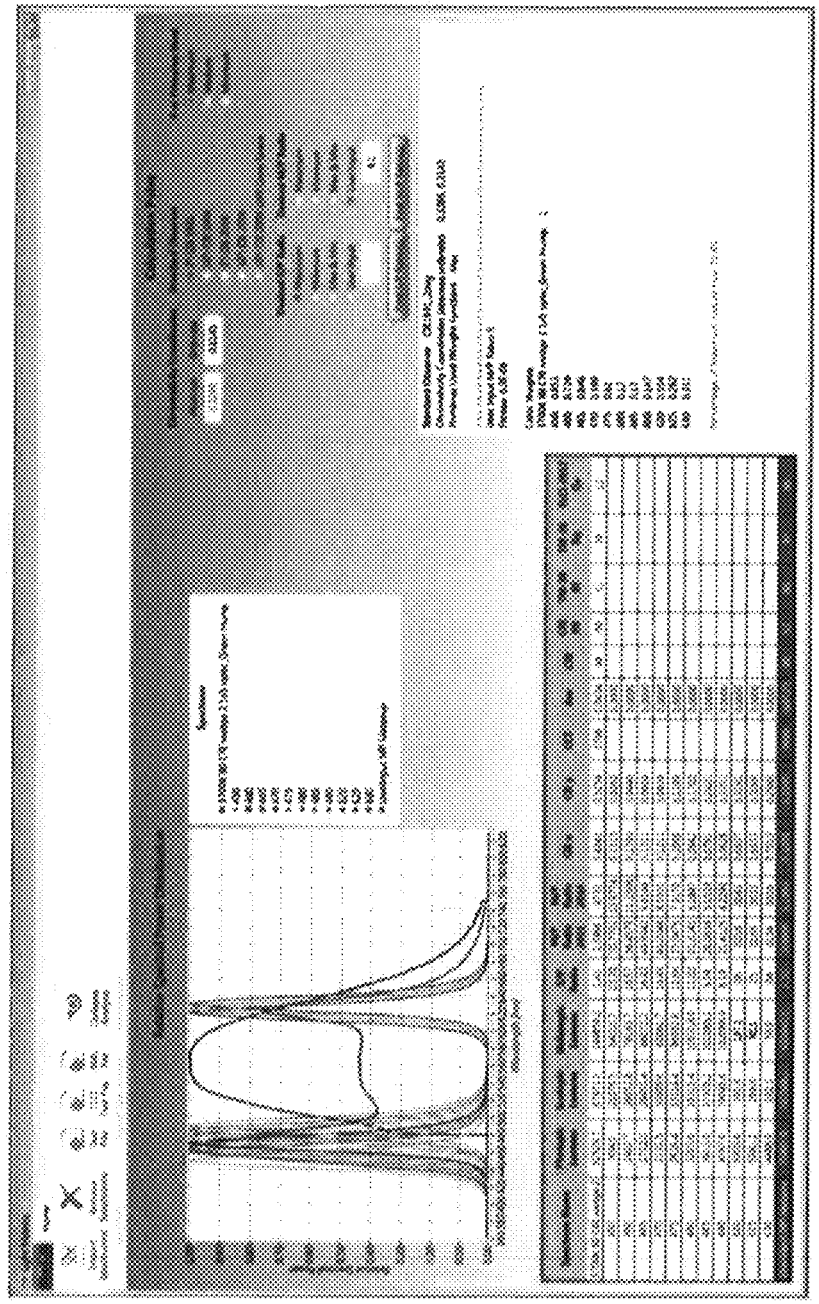
Figure 3Z:
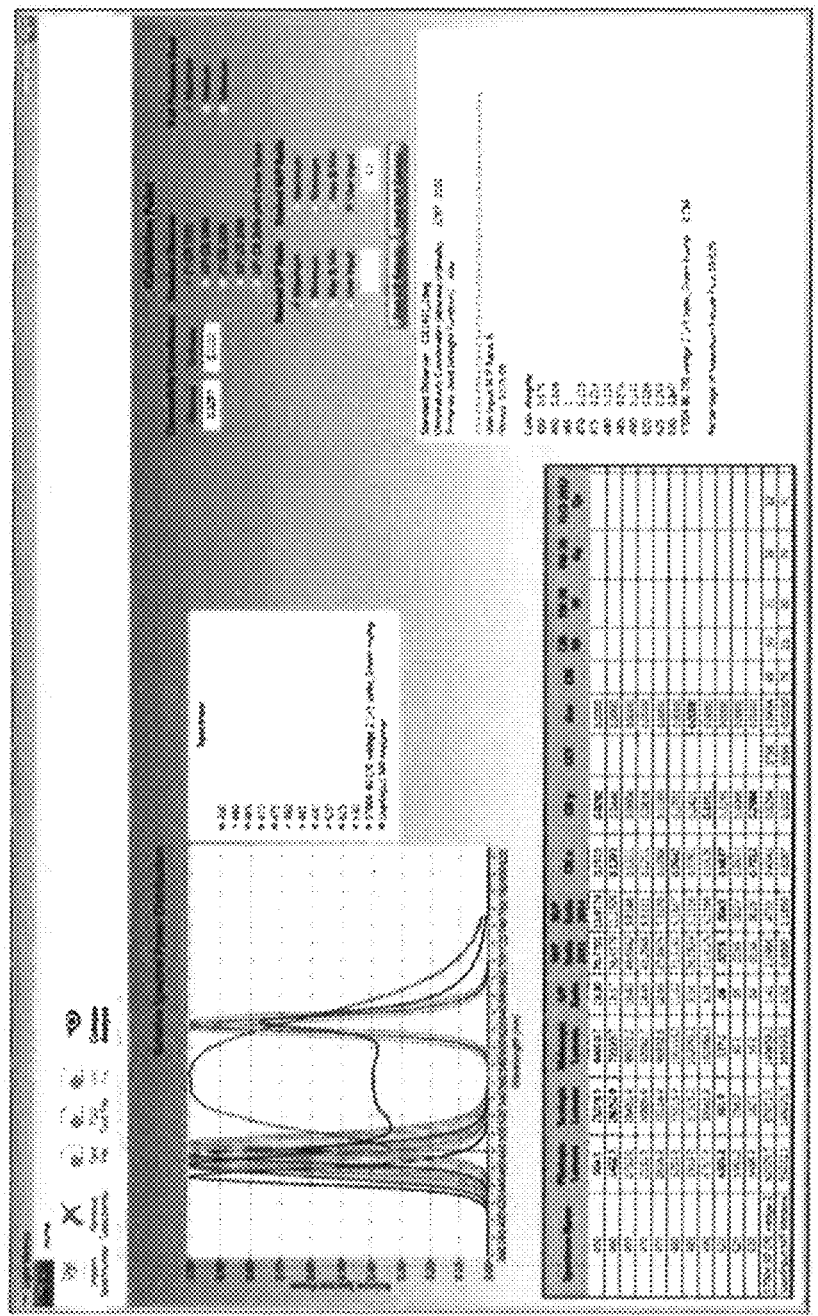
Figure 3A:
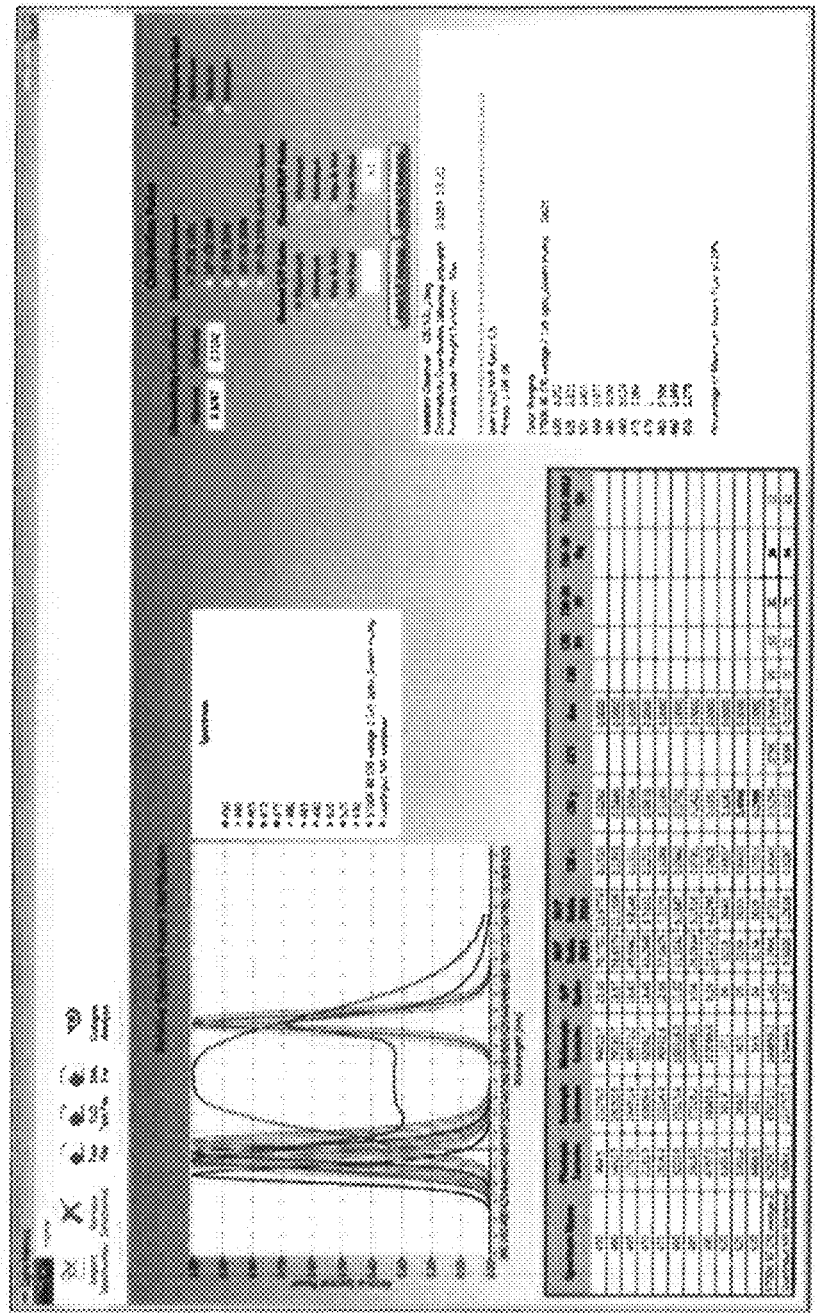
Figure 3B:
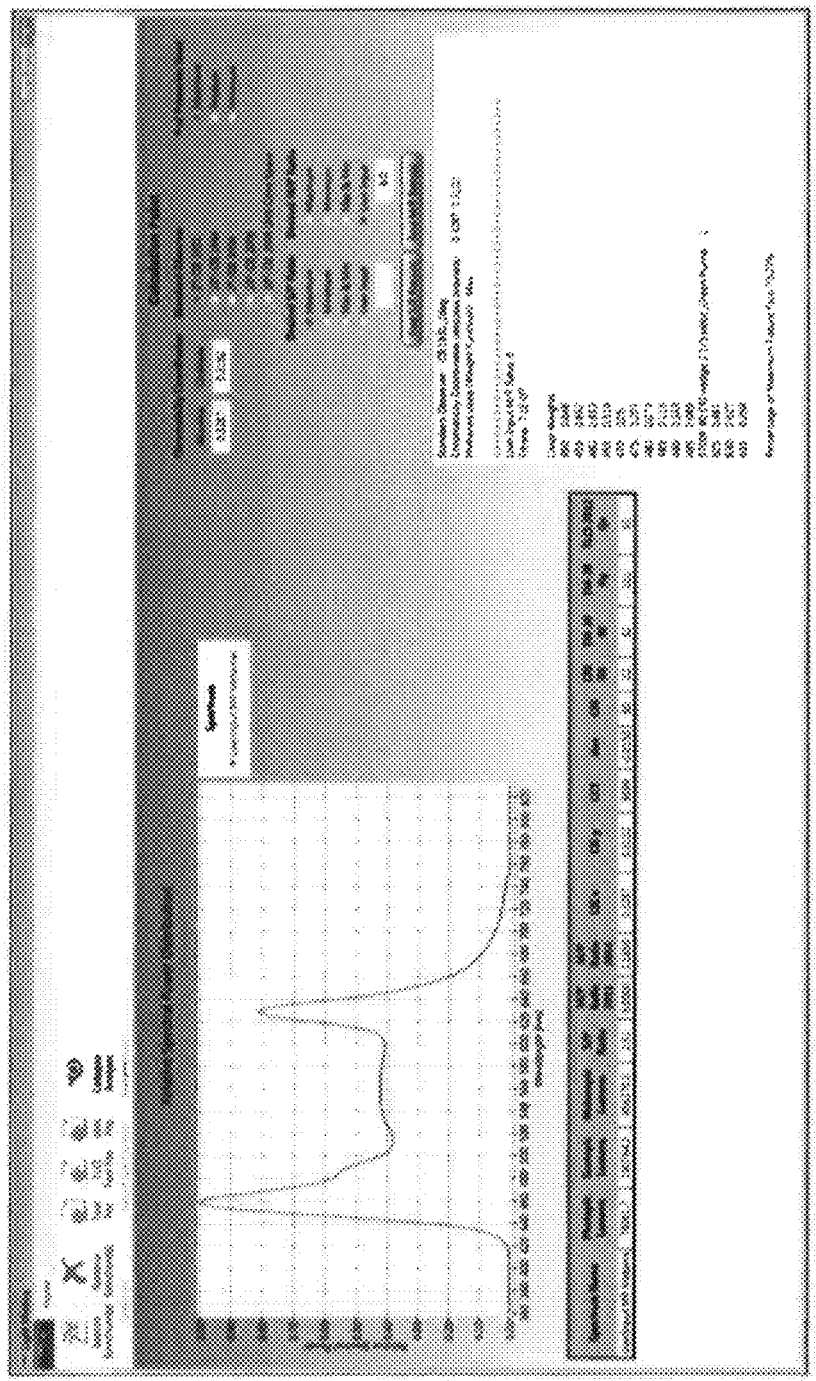
Figure 3C:
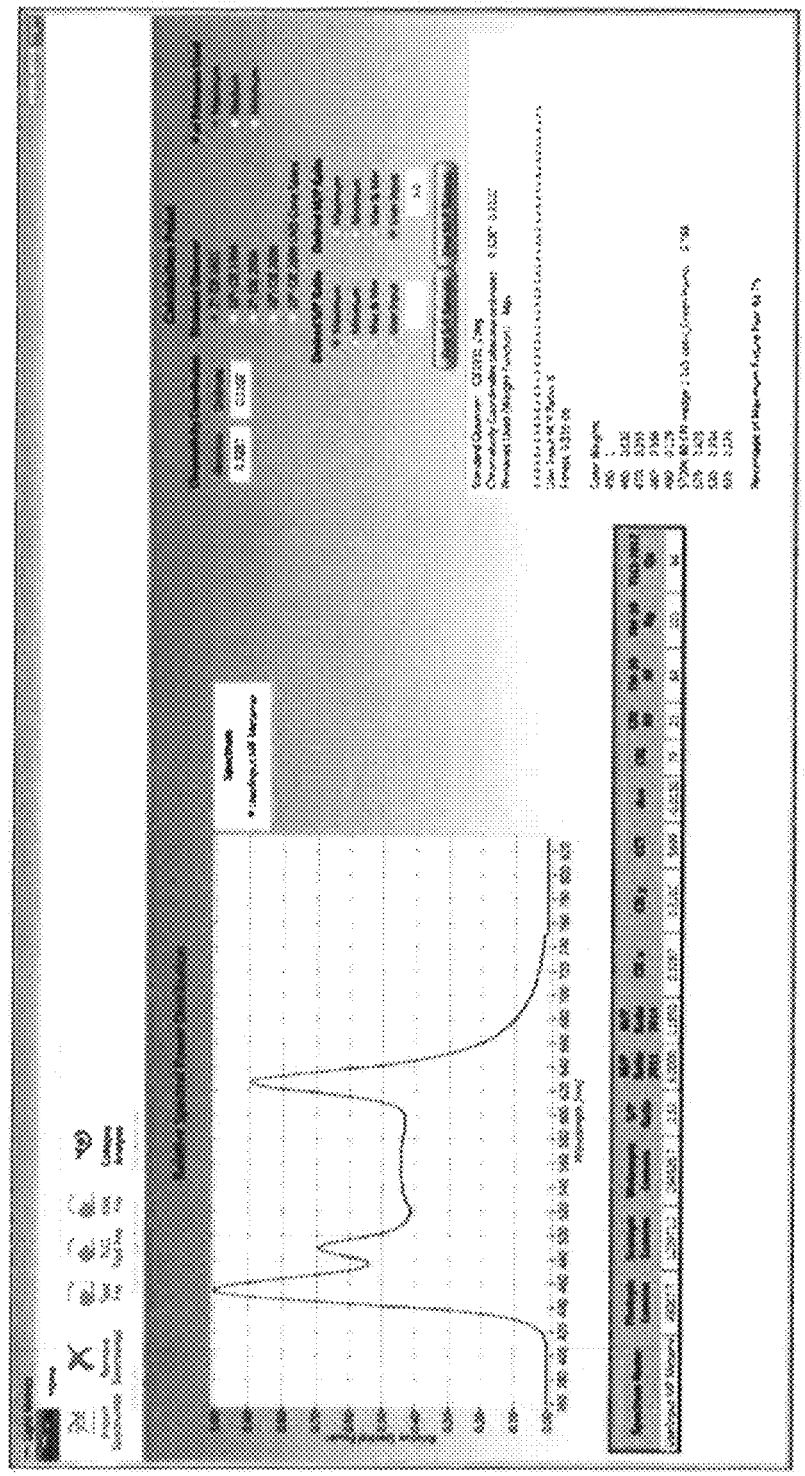

A method according to aspects of the invention for creating metamers with high melanopic content/greater perceived brightness than other metamers with lower melanopic content is described in FIGS. 3A-3DD. Various SPDs are created at several CCTs, with CRI and TLCI mapped as a function thereof (FIG. 3A). These SPDs represent metamers at each of the CCTs and represent desirable SPDs for lighting for which the respective color temperatures are desired, and further which may be designed into "white" LEDs of the respective color temperature, in accordance with methods well-known in the industry for creating a specific SPD for LEDs. Examples of industry methods for LED design with phosphors may be found e.g. in Zollers, M. "Phosphor Modeling in LightTools" 2011, Synopsys Inc., 700 East Middlefield Road, Mountain View, Calif. 94043, downloaded from optics.synopsys.com/lighttools/pdfs/ModelingPhosphorsInLightTools.pdf on Dec. 14, 2016; also in Hsu et al, "Selecting Conversion Phosphors for White Light-Emitting Diodes Package by Generalized Reduced Gradient Method in Dispensing Application," 2015, Green Energy and Environment Research Laboratories, Chutung, Hsinchu, 31040, Taiwan, downloaded from www.nusod.org/2015/nusod15_paper46.pdf on Dec. 14, 2016.

Figure 4A:
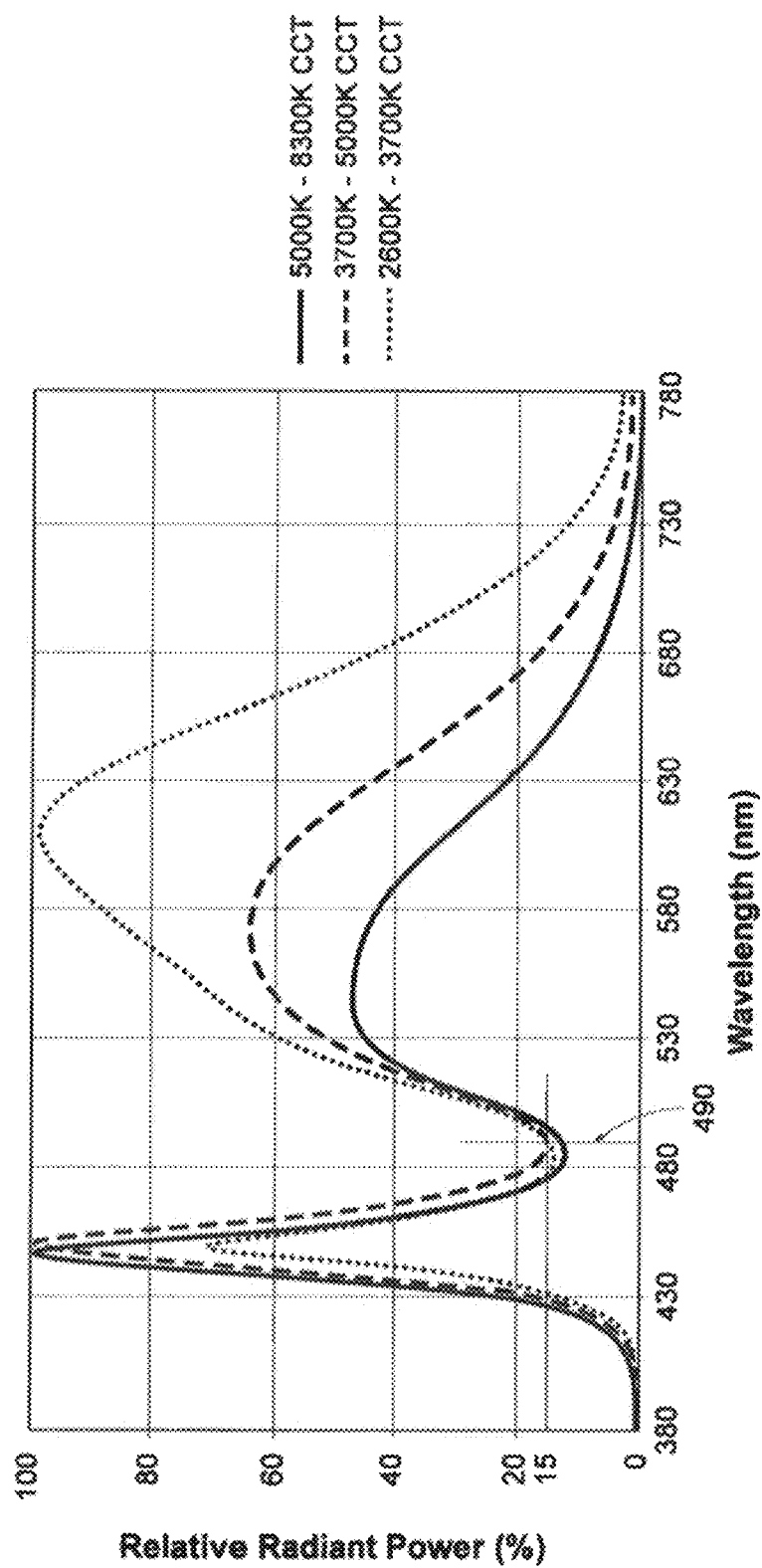
FIGS. 4A-B illustrate SPDs for various light sources.

An SPD having a high melanopic content may be described in several ways. One important way is simply to note the relative value of the spectral content at and around 490 nm wavelength. FIG. 4A illustrates an SPD for a commonly used LED, the "Cree XP-G" as described extensively in the Cree XP-G Datasheet previously cited.

Figure 4B:
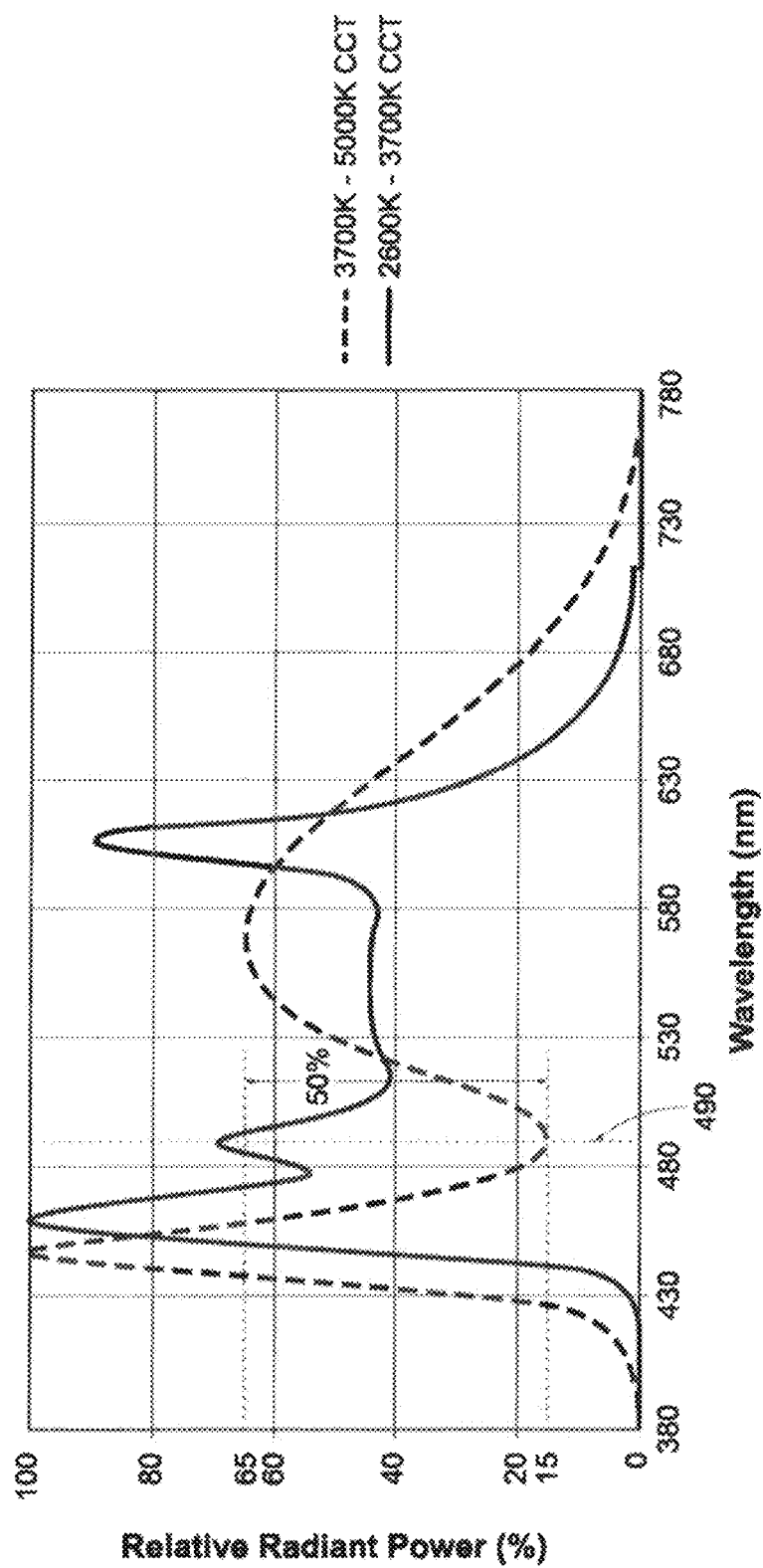

Three different CCTs are represented in the graph. Each of the SPDs for the different CCTs represented have a pronounced trough at 490 nm, with a relative value of approximately 15%. FIG. 4B illustrates, for example, the SPD designated as 3700K-5000K, juxtaposed at the same scale with the value for a high melanopic content SPD (i.e. the 5700K MET20160602_2, as shown in FIG. 3CC) developed in accordance with aspects of the present invention. It is very important to notice that the CREE LED is typical of the current approach in industry; further that the 5700K MET20160602_2, as shown in FIG. 3CC has a relative value of 70% at the 490 nm wavelength which is over 3.5 times as much melanopic content at the crucial 490 nm locus.

Brightness Equivalency Calculation—FIG. 3B

A simplified approach for brightness equivalency calculation is illustrated in FIG. 3B, where BE (M/P)=Lux-Source1/LuxSource2=[(M/P) Source2/(M/P) Source1]0.32

And for example with M/P as a function of CCT & CRI [M/P(CCT,CRI)]:

Source1: M/P(4500,81)=5.0

Source2: M/P(6500,64)=7.3;

Given: application of Source2 yields 100 lux of photopic illuminance

BE(M/P)=(7.3/5.0)0.32=1.129≈113 lux with Source1 to have BE with Source2 which is at 100 lux This is applied as follows:

Source1: Musco's LA-30Z-1: CCT @4,200K; M/P=3.51; CRI=68

Given: application of Source2 yields 100 lux of photopic illuminance
Source2: 4,500K LED: CCT 4,459; M/P=3.55; CRI 75
BE(M/P)=(3.55/3.51)0.32=1.0036≈100.4 lux with Source1 to have BE with Source2
Source2: Cree XP-L: CCT 6,261; M/P=3.92; CRI=67
BE(M/P)=(3.92/3.51)0.32=1.036≈104 lux with Source1 to have BE with Source2
Source2: MET20160309_1: CCT 6,500K; M/P 7.3; CRI 64
BE(M/P)=(7.3/3.51)0.32=1.264≈126 lux with Source1 to have BE with Source2
Source2: MET20160309_4: CCT 5,600K; M/P 6.8; CRI 65
BE(M/P)=(6.8/3.51)0.32=1.226≈123 lux with Source1 to have BE with Source2
Source2: MET20160309_12: CCT 17,000K; M/P 9.5; CRI 65
BE(M/P)=(9.5/3.51)0.32=1.375≈138 lux with Source1 to have BE with Source2
Note: If using S/P ratio, use 0.436 as exponent
Brightness Equivalency Variation Calculation—FIG. 3C
A brightness equivalency variation is calculated as follows as shown in FIG. 3C:

$$R_2 = e^{(\ln(r^{-1} \cdot R_1^{-c}) \cdot ^{-1})}$$

where:
R1=Base Source Ratio, i.e. M/P=2.50
R2=Required Ratio of 2nd Source to achieve desired Light Reduction
r=Light Reduction, i.e. to 75%
c=Exponent for Brightness Equivalence, i.e. 0.32
Example:

$$R_2 = e^{(\ln(0.75^{-1} \cdot 2.50^{\hat{}} 0.32) \cdot -0.32^{\hat{}} -1)}$$

$R_2 = 6.14$

So, if you had a light source with an MIP ratio of 2.50 and wanted to reduce photopic light levels by 25% (to 75%) while maintaining equivalent brightness, you would need the second light source to have an M/P ratio of 6.14.

Figure 3D:
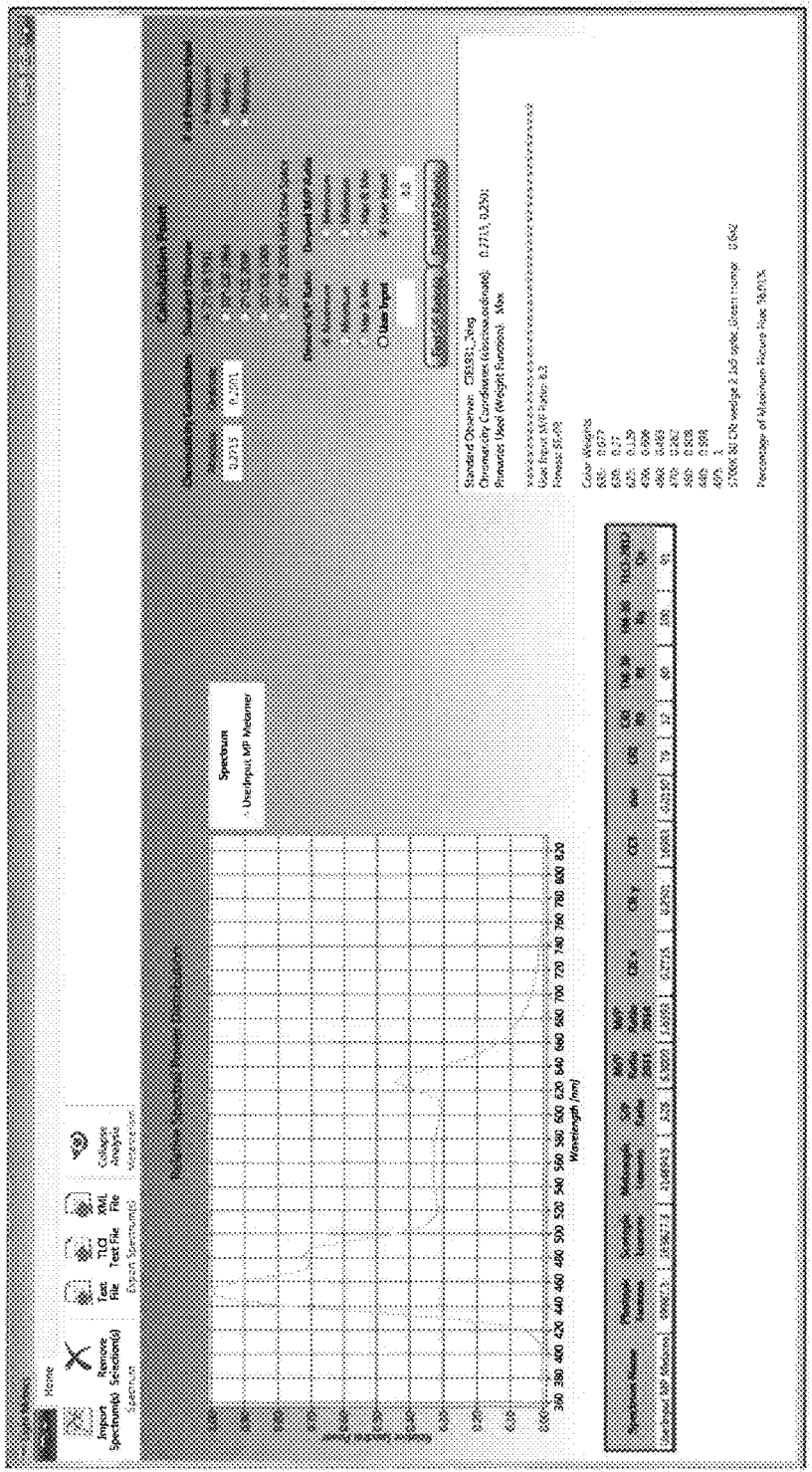

Parameters and Inputs—FIG. 3D
FIG. 3D lists Parameters/Inputs
SPD Inputs (All normalized to 1.0 at peak):
  450[10]630 monochromatic light
  Melanopic Curve
Min CRI 60
Metamers generated in Musco developed 'Light Metric' application Melanopic function taken from Lucas (Faculty of Life Sciences, University of Manchester, Manchester M13 9PT, UK), et al, Lucas et al 2014 workbook.xls, 2014
Maximum spectral efficacy (K*m)
K*m=Km/(φz,555/φz,490)=4,214.6≈4,215
  Where Km=683; φz,555=0.0018483287; φz,490=0.0114055016
  φz,λ=spectral power from the melanopic function at the specified wavelength
Calculated Metamers—FIGS. 3E-3DD
FIGS. 3E-3DD represent various metamers having high melanopic content for use in lighting for sports or wide-area lighting, with their calculated CRI, R9, M/P and TLCI figures. For example, FIG. 3E represents a metamer designated MET20160510_1, having the following specifications:
CCT 17,000K
CRI 67
R9 (CRI R9) 20
M/P 9.5;
TLCI 62

Figure 10:
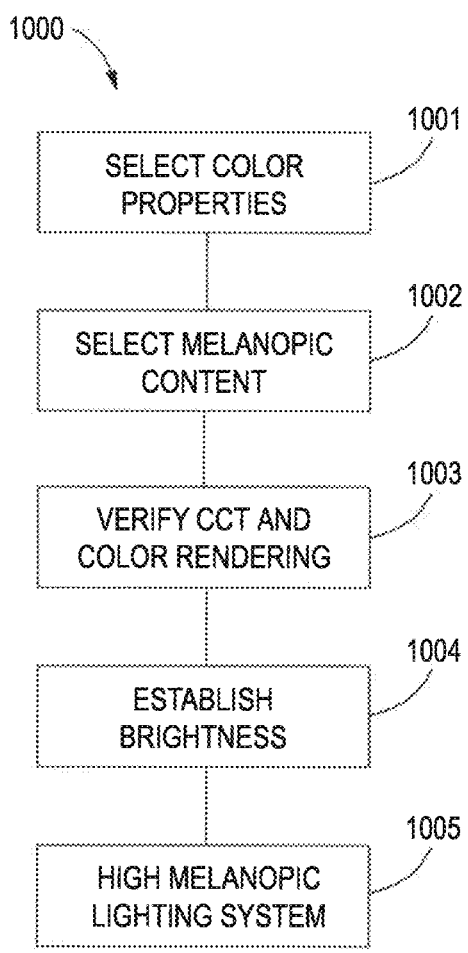
FIG. 10 illustrates a flow chart describing a method according to aspects of the invention.

The remaining figures represent other metamers at the following CCTs, with other specifications as listed in the figures:
17,000K: FIGS. 3E-H, W, AA, and DD
16,000K FIG. 3X
10,000K: FIGS. 3I-K
6,500K: FIGS. 3L-N
5,700K: FIGS. 3O-Q, U-V, Y-Z, BB and CC
4,500K: FIGS. 3R and S
3,000K: FIG. 3T D. Embodiment 3—a Method for Creating, Modifying, or Adding Lighting Equipment for Increasing Perceived Light Brightness by Using Light Having High Melanopic Content A method according to aspects of the invention is illustrated in the block diagram 375 of FIG. 12B wherein, lighting equipment is created, modified, or added to in order to increase perceived light brightness by using light having high melanopic content, as measured by its M/P (melanopic/photopic) ratio.

First, either an existing lighting apparatus such as 510, FIG. 11A, which provides a lighting pattern 516 on a surface or target area such as sports field 515, is selected for improvement, step 380. Alternatively, a need for a lighting apparatus is recognized, step 382. Metamers having a desired CCT are compared for optimum perceived brightness, step 384. These metamers are evaluated for improved brightness and desired CCT, as well as for meeting target values for color rendering. If they are not within parameters step 388, steps 384 and 386 are repeated. If they are within parameters, the lighting apparatus is manufactured, step 390. The result is an improved lighting apparatus, step 392, which per step 394 emits high brightness light having high melanopic content, further having an M/P ratio and a CCT that are sufficiently high to create the desired effect.

Note that while field conditions, type of venue, average age of audience, or other factors may have a large influence on actual desired limits, an S/P ratio of 2.0 or greater, possibly as high as 3.0, and a CCT of 6,500K or less, and a CRI of 65 or greater are believed to be acceptable for sports lighting. However, since some standards or local expectations for sports lighting can require a CCT lower than 6,000K, several 5,700K CCT metamers having high melanopic content and good color rendering, as measured by several standards, are described in e.g. FIGS. 3O-Q, U-V, Y-Z, BB and CC. Further, an S/P ratio of 3.0 or greater and a CCT of 10,000K or less may be acceptable. Desired limits for M/P or S/P ratio and for CCT can be verified with laboratory and/or field testing of the manufactured lighting to validate results for actual usage conditions. Still further, CCTs as high as 17,000K may be acceptable or desirable for some locations such as sports fields, parking lots, ship yards, etc., where the highest possible perceived brightness is desired.

For embodiments of the invention, metamers may be created by selecting LEDs having specific SPD characteristics. Zollers 2011 and Hsu 2015 both describe methods and techniques for designing phosphor combinations for LEDs. Note that LEDs as currently manufactured can have varying SPDs based on variances within the process. They are currently typically sorted into "bins" indicating their color temperature, but could also be sorted within a given color temperature range for SPD, and the ones exhibiting a desired metamer selected. Or a combination of two or more types of white LEDs each having a specific SPD that combine to form the desired metamer could be selected. Or sets of three or more generally monochromatic LEDs could be selected to create a desired SPD having high melanopic content using well-known RGB or other tri-chromatic schemes for creating white light. This would build on available and anticipated techniques for manufacturing, creating, and classifying LEDs according to SPD. Thus it can be seen that techniques exist for potentially creating high melanopic metamers at a given color temperature, assuming availability of sufficient variations of SPDs of white LEDs or of sets of three or more monochromatic LEDs.

"LED Color Mixing: Basics and Background" by CREE, as previously cited, describes LED colorimetry and binning in great detail. Also "Understand color science to maximize success with LEDs (MAGAZINE)" describes how light sources can have identical chromaticity coordinates (i.e. have identical color temperatures) but differing SPDs.

Figure 2A:
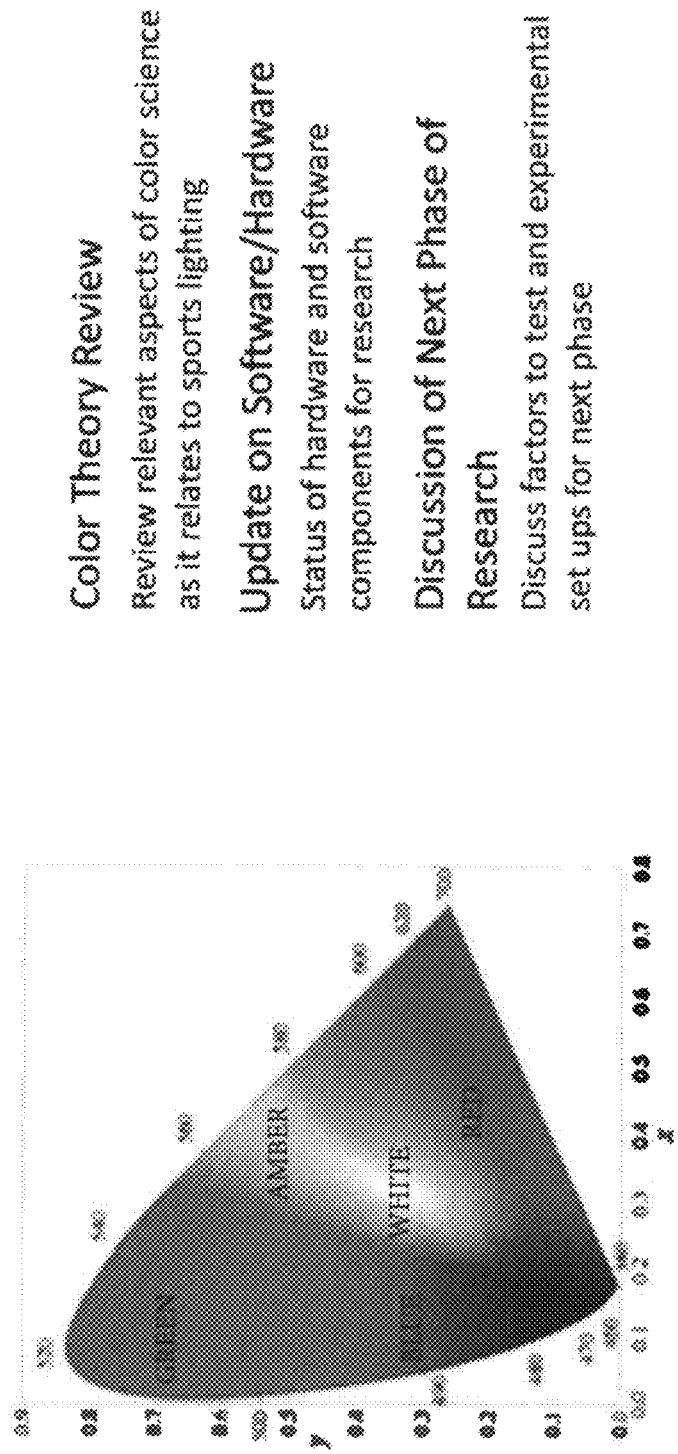
FIGS. 2A-P illustrate methods according to aspects of the invention.
Figure 2D:
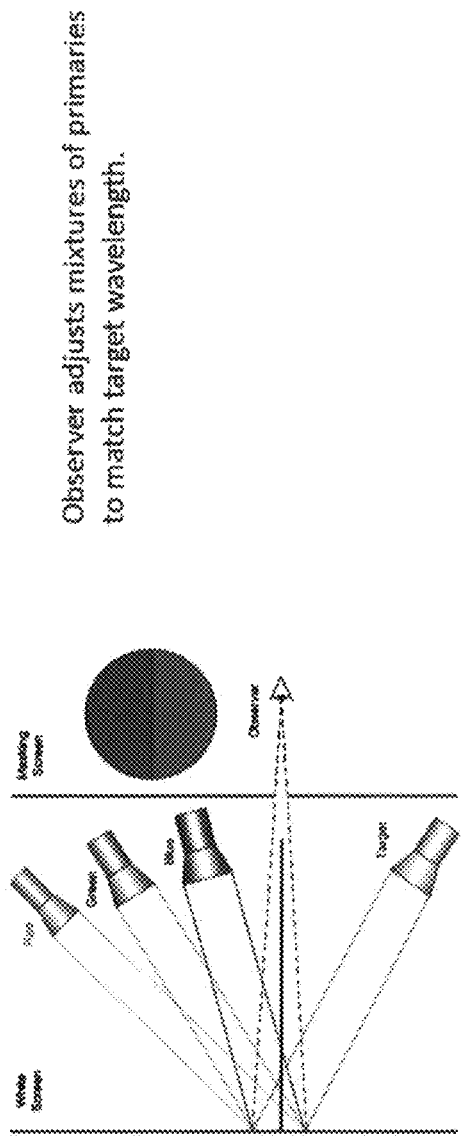
Figure 2F:
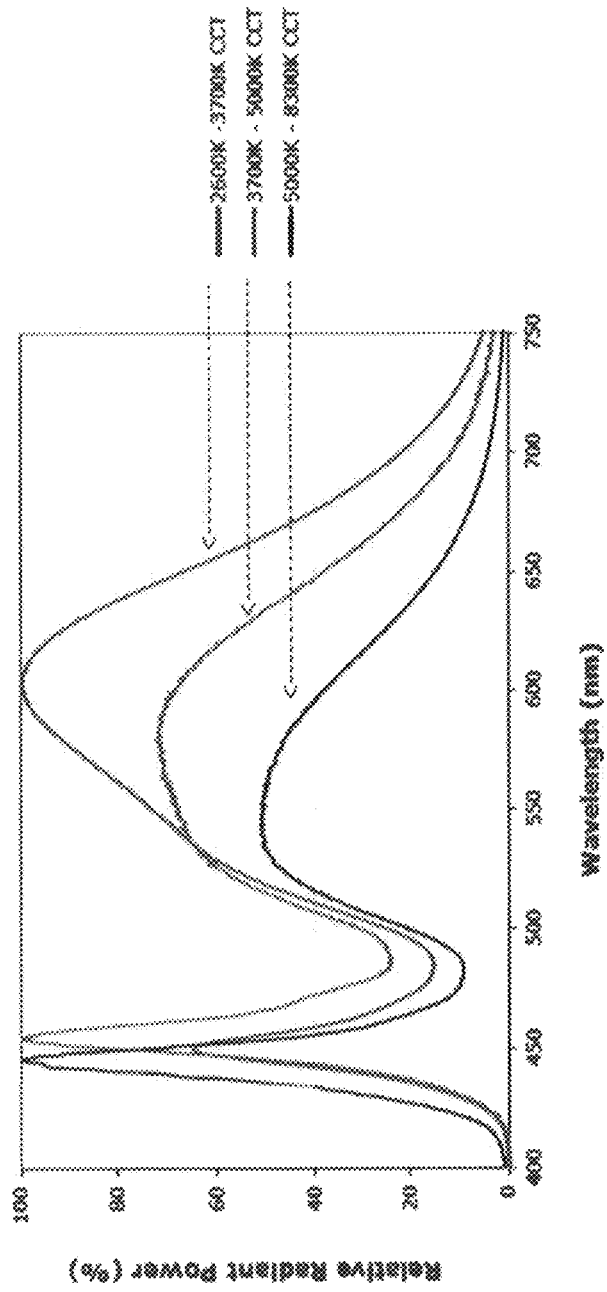
Figure 2G:
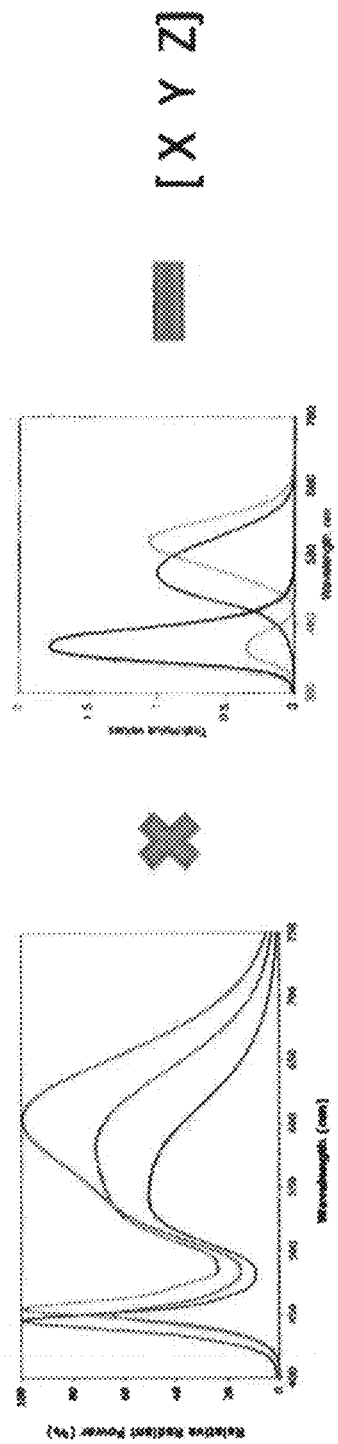
Figure 2H:
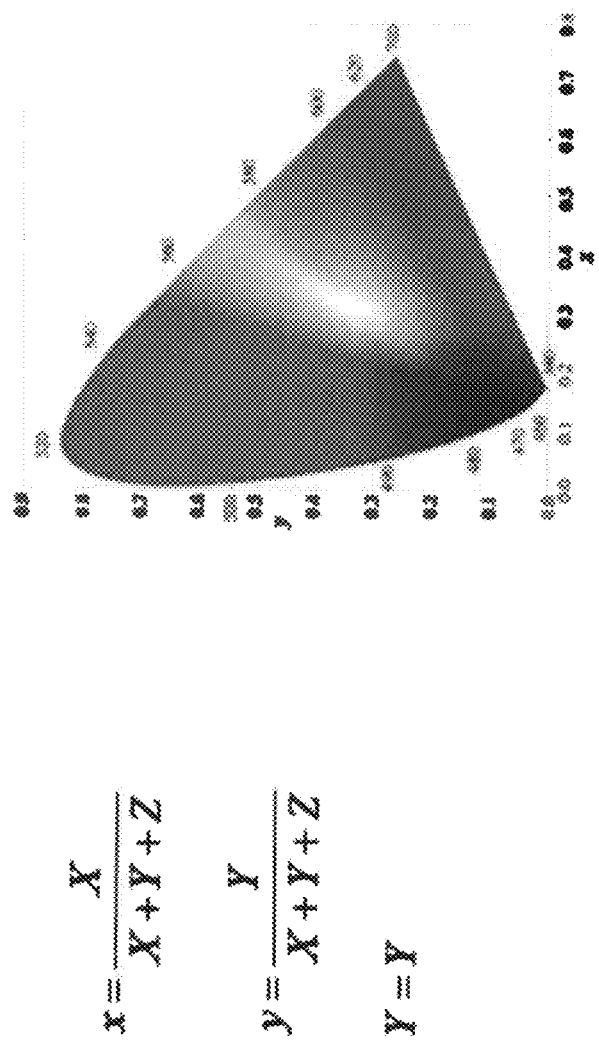
Figure 2J:
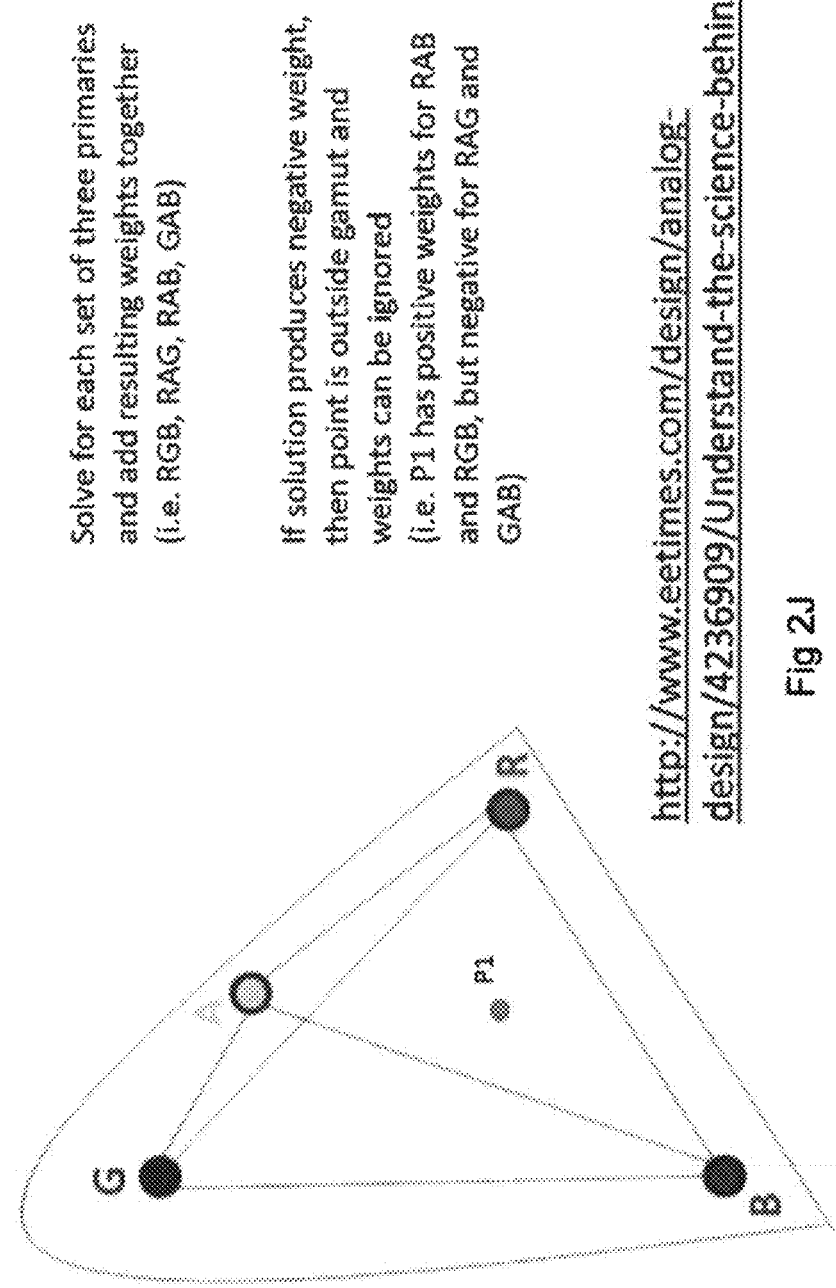
Figure 2M:
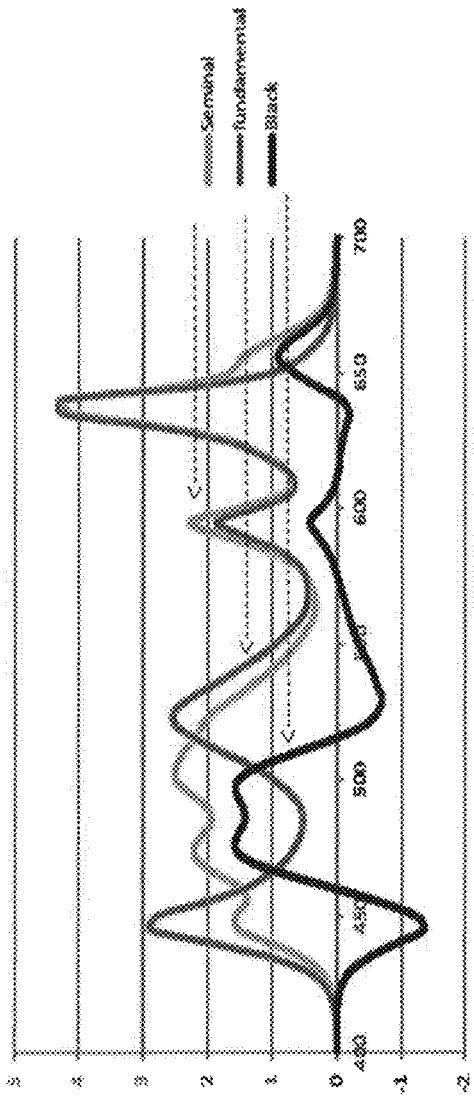
Figure 2P:
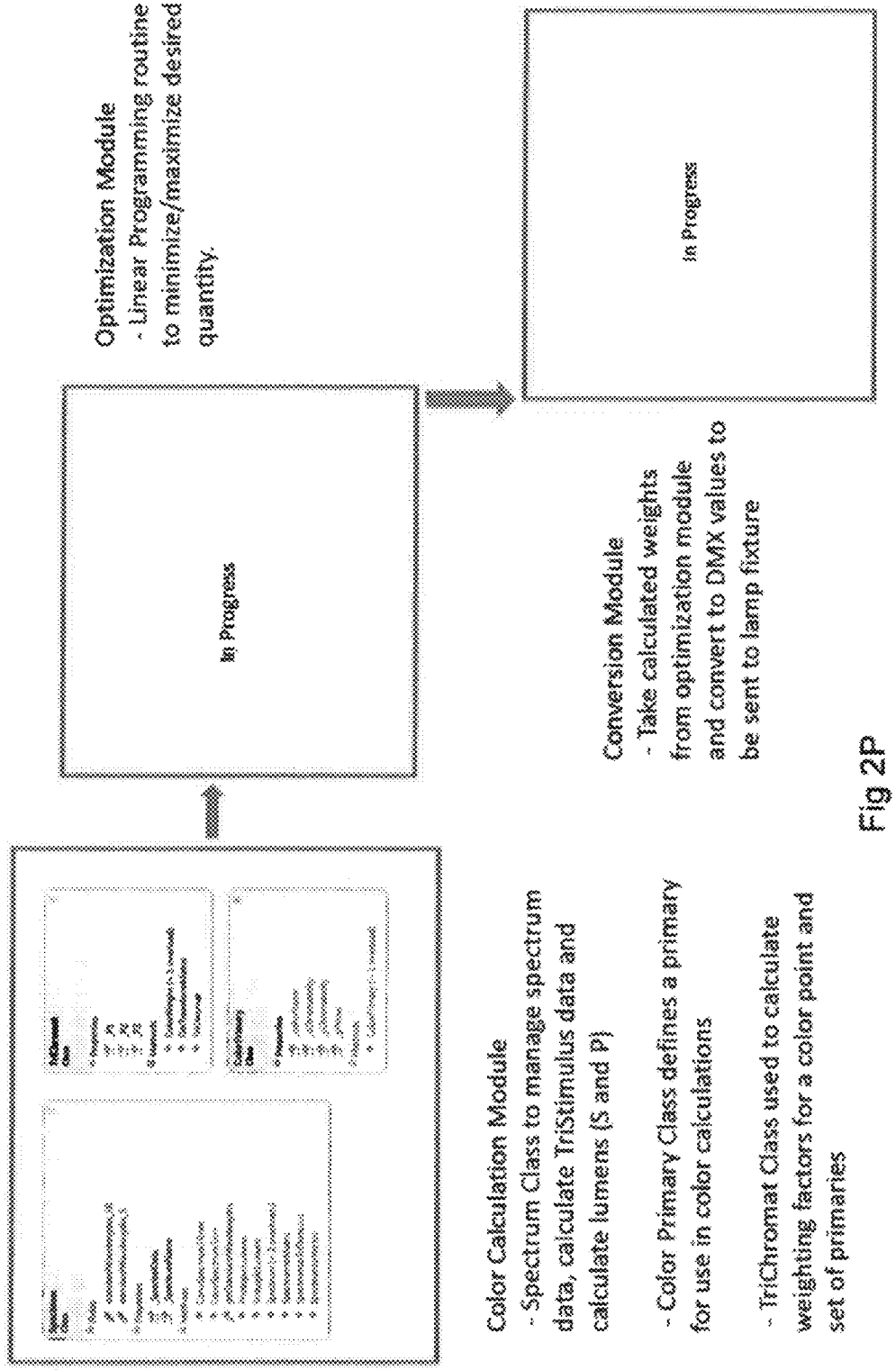

E. Embodiment 4—a Method for Creating Metamers or SPDs for Desired CCTs and High Melanopic Content, Wherein the Known Sources or Inputs Comprise SPDs from Existing Monochromatic or Polychromatic LEDs In an embodiment according to aspects of the invention, known sources or inputs for known SPDs are used in conjunction with calculation methods known in the industry some of which are described herein (e.g. as discussed in Boxier, see FIGS. 2A-P; also Schutz, see FIGS. 3A-3DD, and IES #1 and #2 as referenced) to assist with creating metamers for desired CCTs and high melanopic content, wherein the known sources or inputs comprise SPDs from existing monochromatic or polychromatic LEDs, or from existing phosphors known to produce certain SPDs under excitation from known LED sources. Further known sources or inputs comprise posited SPDs from known industry methods for creating phosphors or for creating monochromatic or polychromatic LEDS.

The chart found in FIG. 3S, reproduced as FIG. 5, lists color weights for known sources (such as e.g. monochromatic LEDs or phosphors used with known LEDs) to create a CCT represented by the listed chromaticity coordinates (i.e. abscissa, ordinate of 0.32805, 0.33717) in the CIE 2006 color space (see IES #2, p. 5).

FIGS. 8A-D illustrate aspects of this embodiment as also explained in IES #1 and #2.

Figure 6:
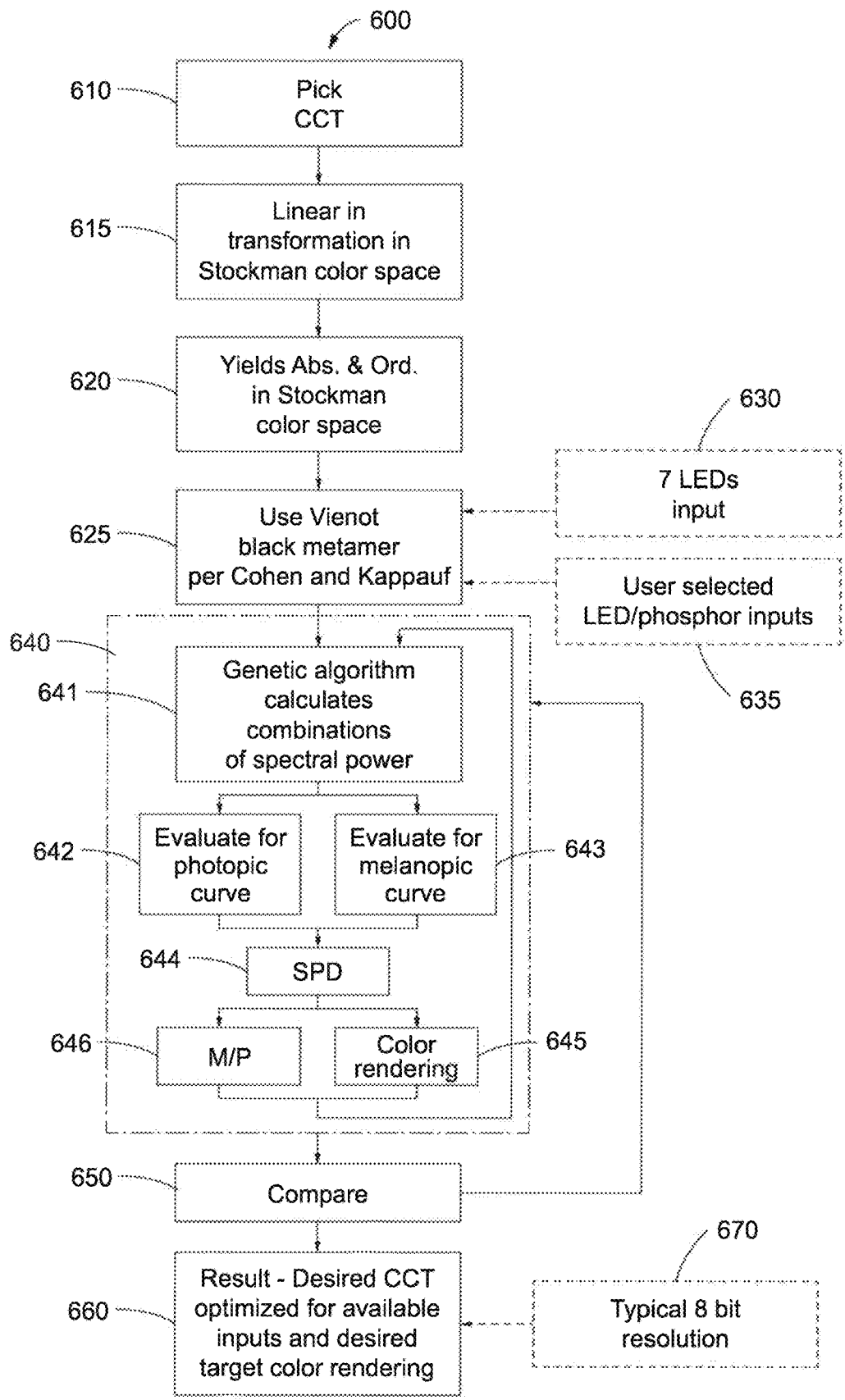
FIG. 6 illustrates a flow chart according to aspects of the invention.
Figure 7A:
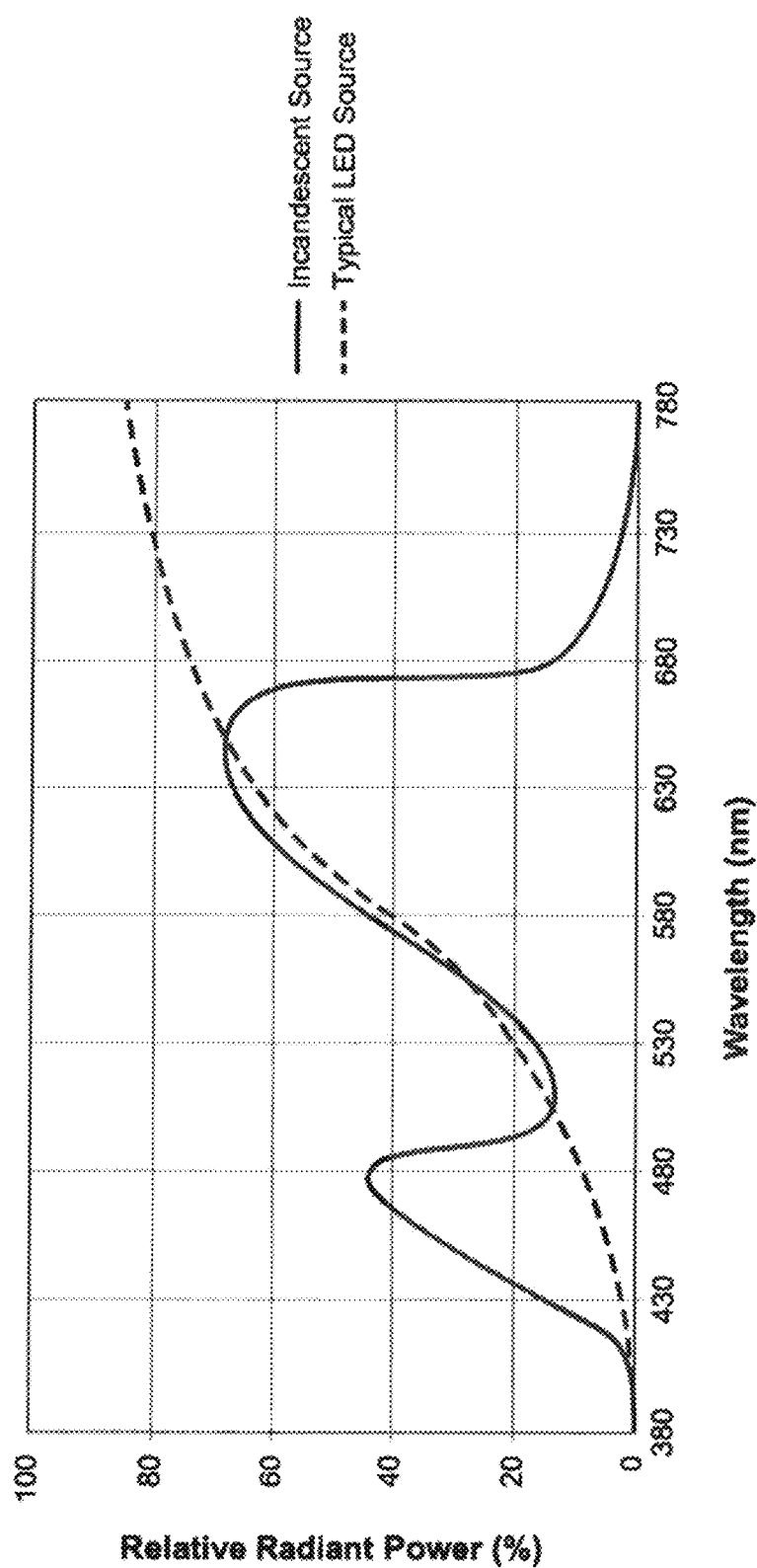
FIG. 7A illustrates SPDs for typical incandescent vs. LED light sources.
Figure 7B:
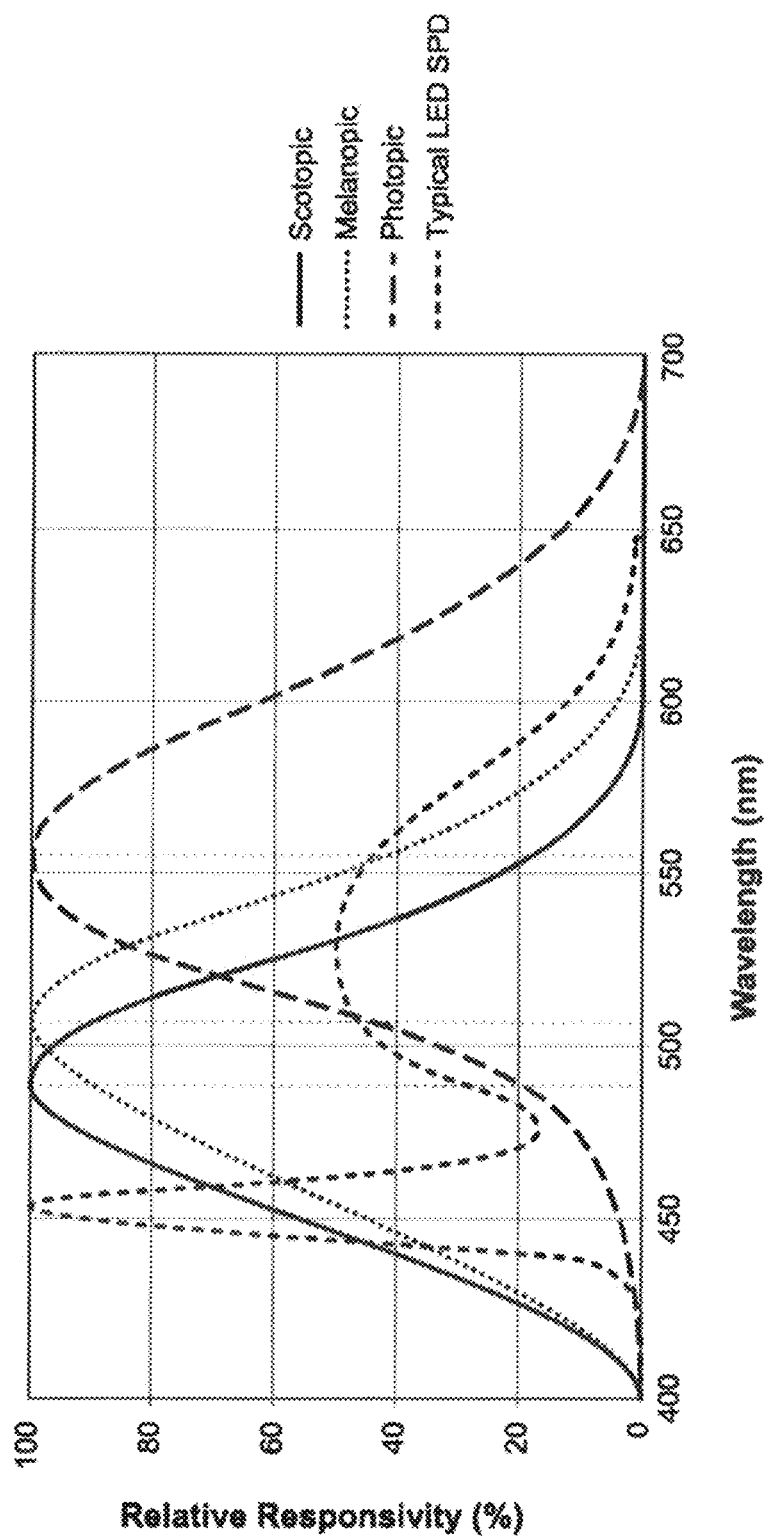
FIG. 7B illustrates a typical LED SPD vs. the Melanopic, Scotopic, and Photopic Sensitivity Curves.

F. Embodiment 5—Creating an SPD at a Desired CCT with Acceptable Color Rendering FIG. 6 illustrates in flow chart form an embodiment 600 according to aspects of the invention. First, step 610, a desired CCT for lighting is selected. Second, linear transformation is used to locate the desired color in the Stockman CIE 2006 color space (see IES #2, p. 5), step 615. This yields a calculated abscissa and ordinate in the said color space, step 620. Next, a black metamer per Vienot, Cohen and Kappauf is created (step 625) to begin selection of a metamer that can be created using various inputs. Inputs can be e.g. the seven LEDs used in the IES studies #1 and #2, step 630, or can be from lighting sources that are available or can reasonably be believed to be available based on existing technology for creating e.g. phosphors for LEDs, step 635. Next a genetic algorithm is used iteratively, step 641 to calculate possible solutions and compare with other possible solutions. Within this process, a combination of sources at various relative SPDs is presented, then evaluated and weighted according to melanopic and photopic curves shown in FIG. 7B; in this step luminous flux is evaluated/weighted according to the following "formula for visual sensitivity curve" applied to the photopic curve (FIG. 7B), step 642, and to the melanopic curve (FIG. 7B) step 643 where a sample SPD for the desired luminous flux is input.

Formula for the Photopic Curve $$\Phi_v = K_m \Sigma_{360}^{830} \Phi_{e,\lambda} V(\lambda) d\lambda$$

Where, $\Phi_v$=total flux, $K_m$=maximum spectral luminous efficacy of radiation.
This is 683 for photopic vision, 4215 for melanopic vision using the Wyszecki method, and 832.4 for melanopic vision using the Lucas method.

$\Phi_{e,\lambda}$=spectral radiant flux emitted from the light source,
$V(\lambda)$=spectral responsivity of human vision in a 2° field of view for photopic vision.
This can be substituted for the spectral responsivity function with different fields of view and human responses, i.e. the melanopic spectral responsivity function peaks around 490 nanometers and necessitates a 10° field of view to elicit a response from ipRGC.

$d\lambda$=wavelength delta

Within the iterative process 640, a resultant non-final SPD step 644 is generated. This SPD is then evaluated for M/P ratio (step 646) and color rendering metrics (step 645), and (in simplified terms) is compared by the genetic algorithm with previous results. The best results are kept and then further refined iteratively for as many repetitions as are practical or desired, step 650. When the process is completed, and if sufficient color sources were included in the calculation, the result, step 660, is an SPD that is at or very close to the desired CCT with acceptable color rendering. This SPD is then formulated, using the values provided from the algorithm, into a desired combination of LEDs or desired LED construction of a base LED source plus added phosphors (or other color conversion agents). It is noted that the formulation can generally be satisfactorily obtained using 8-bit (0-255) resolution, step 670.

Figure 12A:
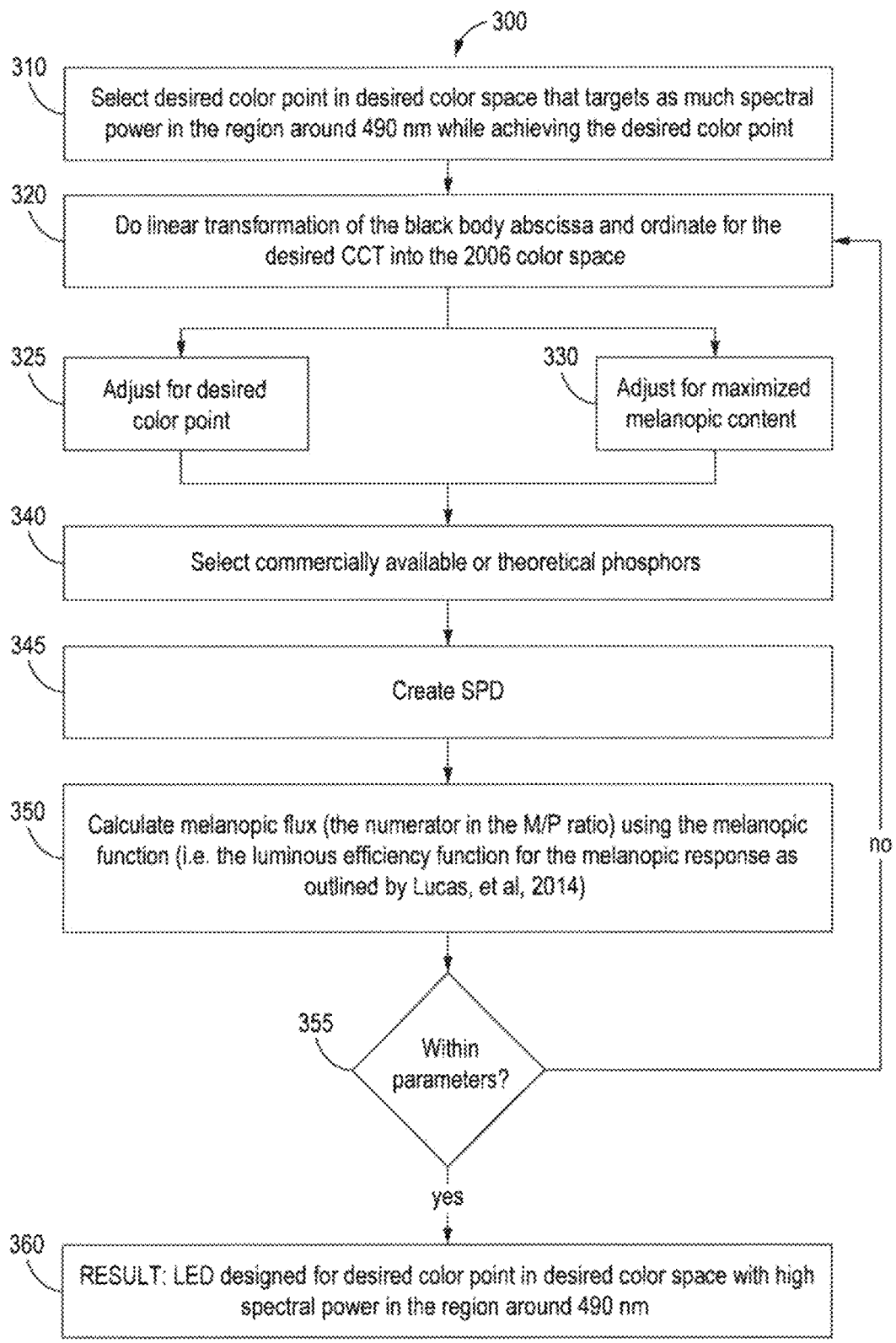
FIGS. 12A-B illustrate flow charts describing methods according to aspects of the invention.
Figure 12B:
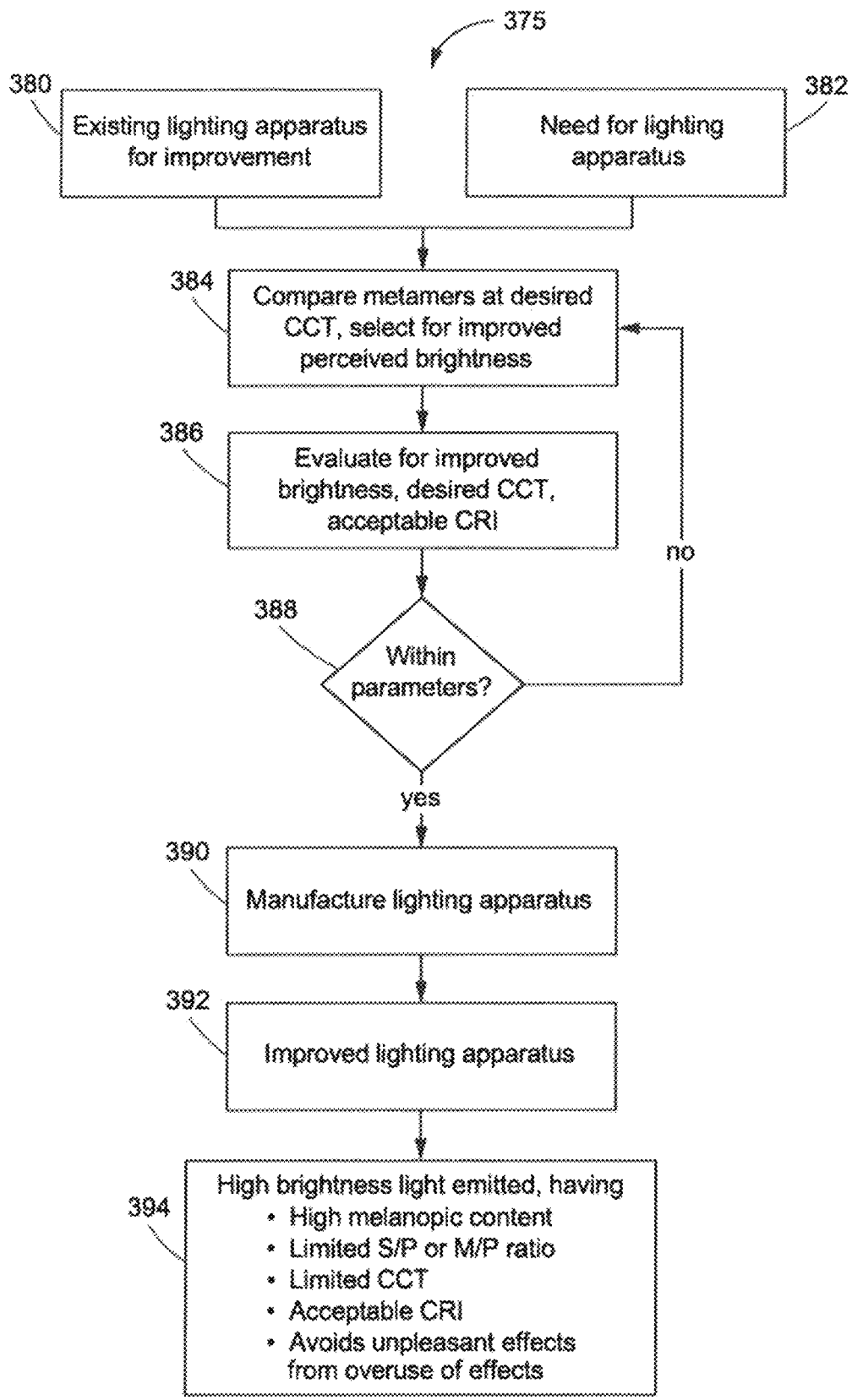

G. Embodiment 7—LED Lighting Fixture Employing a Plurality of LEDs Having a High Melanopic Content FIG. 12A illustrates in flow chart form an embodiment 300 for creating high melanopic light according to aspects of the invention. First, step 310, select desired color point in desired color space that targets as much spectral power in the region around 490 nm while achieving the desired color point. Next do a linear transformation of the black body abscissa and ordinate for the desired CCT into the 2006 color space, Step 320. Adjust for desired color point step 325 and maximized melanopic content step 330. Select commercially available phosphors or specify desired phosphors for commercial creation according to existing art, Step 340. Next, create the desired SPD having desired CCT and color rendering, Step 345. Then calculate the melanopic flux of the created SPD using the melanopic function (e.g. as outlined by Lucas), step 350. Then per Step 355, if melanopic flux, CCT, and color rendering is within parameters, result is an LED design for desired color point in desired color space with high spectral power in the region around 490 nm, Step 360. If not, repeat the process with modified inputs to obtain desired results.

Figure 9A:
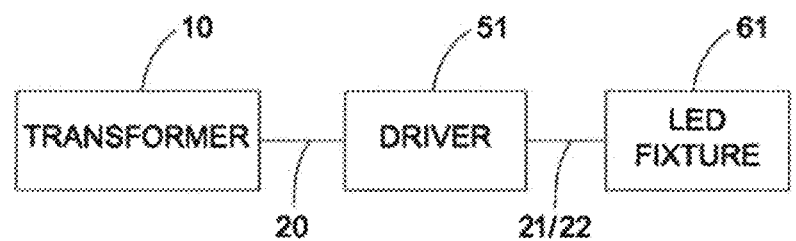
FIGS. 9A-D illustrate an apparatus for LED light output according to aspects of the invention.
Figure 9B:
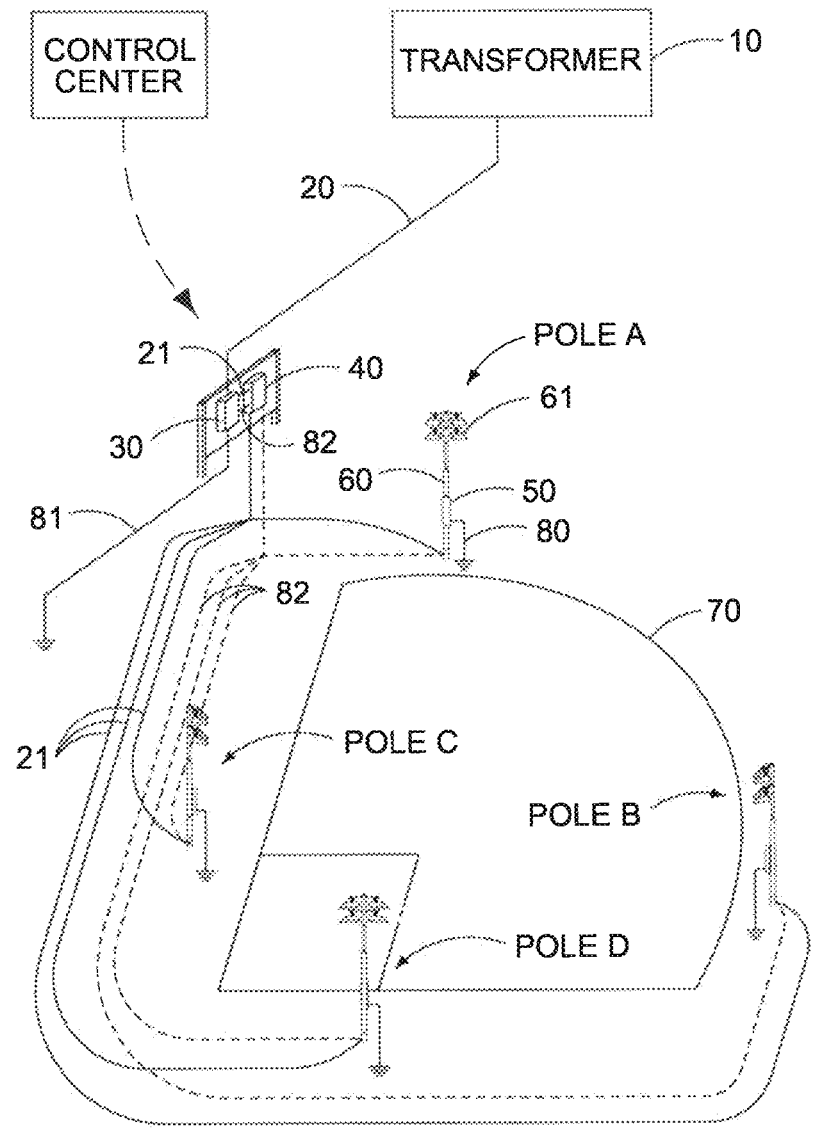

H. Embodiment 8—LED Lighting Fixture Employing a Plurality of LEDs Having a High Melanopic Content This exemplary embodiment sets forth an LED lighting fixture employing a plurality of LEDs having a high melanopic content. The aforementioned LED lighting fixture could take a number of forms—some of which are later described in greater detail—but generally speaking may be described according to FIGS. 9A-D. An LED lighting system generally comprises a power source 10 which distributes power via means 20 to a driver 41 which then distributes power which has been conditioned for use with LEDs via means 21/22 to one or more LEDs 62, FIG. 9D within luminaires 61. The general principle illustrated in FIG. 9A is repeated and customized as needed for a specific task or general purpose, the corresponding lighting system becoming larger or more customized as needed; this is illustrated in FIG. 9B for a baseball field. As can be seen from FIGS. 9A and B, a power source 10 generally comprises a transformer (e.g., from a utility company) which provides electrical power to a service distribution cabinet 30 via a distribution wire 20. Said electrical power travels from service distribution cabinet 30 to a control/contactor cabinet 40 via a power line 21 where it further travels to a pole cabinet 50 housed on each lighting support structure 60 via power line 21, and finally powers one or more LEDs. The result is illumination of field 70. Of course, other considerations are important to note, even in a generic LED sports lighting system such as that illustrated in FIGS. 9A and B. For example, grounding to protect against adverse electrical effects (e.g., lightning) may be provided by earth grounds 80. Equipment grounding may likewise be provided via equipment grounds 81 in combination with ground wiring 82.

I. Exemplary Method and Apparatus Embodiment 9

As previously stated, according to aspects of the present invention a light source having high melanopic content may be provided, and in a manner where perceivable brightness (e.g., as measured by a true brightness meter) and perceivable color (e.g., as measured by the aforementioned tristimulus value) is equivalent to currently available LED lighting sources, but with lower luminous flux required in comparison.

It should be noted that for one or more alternative embodiments discussed herein, luminaire 61 illustrates how subsets of LEDs could be used if multiple LEDs were selected to provide a composite beam having high melanopic content. In this case, a luminaire 61 is envisioned to comprise at least two subsets of LEDs; a first subset having a first composite SPD, and a second subset having a different composite SPD. Additional subsets having still different SPDs could be created if desired.

It should be noted that what comprises "high" melanopic content is dependent upon, among other things, which version of the following efficiency function is used, but for purposes of the invention is generally 1.10-2.20 for a high melanopic content and in the range of 0-1.0 for a low melanopic content (using the following K*m), where melanopic content is a unitless value which represents the ratio of the melanopic luminous efficiency function to the photopic luminous efficiency function (M/P) for a given light source having an SPD. It should be noted, however, that it is the ratio of the high M/P source to the low M/P source which is most relevant—see Equation 1. The melanopic luminous efficiency function ($V^z(\lambda)$) is sourced from the 2014 Irradiance Toolbox published by Lucas et al (lucasgroup.lab.ls.manchester.ac.uk/research/measuringmelanopicilluminance/ website accessed 2016-05-25) assuming a maximum spectral efficiency (K*m) of 832.4, and the photopic luminous efficiency function ($V(\lambda)$) is sourced from the Commission internationale de l'eclairage (CIE) assuming a standard observer angle of 2°; both are known calculations in the art. Also, what comprises a metameric pair is often dependent upon the illumination source (i.e., illuminant metamerism) or the observer (i.e., observer metamerism); for purposes of the invention, the subsets of LEDs are considered metamers if perceived to be the same color by a typical observer under a predefined general purpose (e.g., sports lighting) or with respect to a predefined task (e.g., typical office work).

Figure 8A:
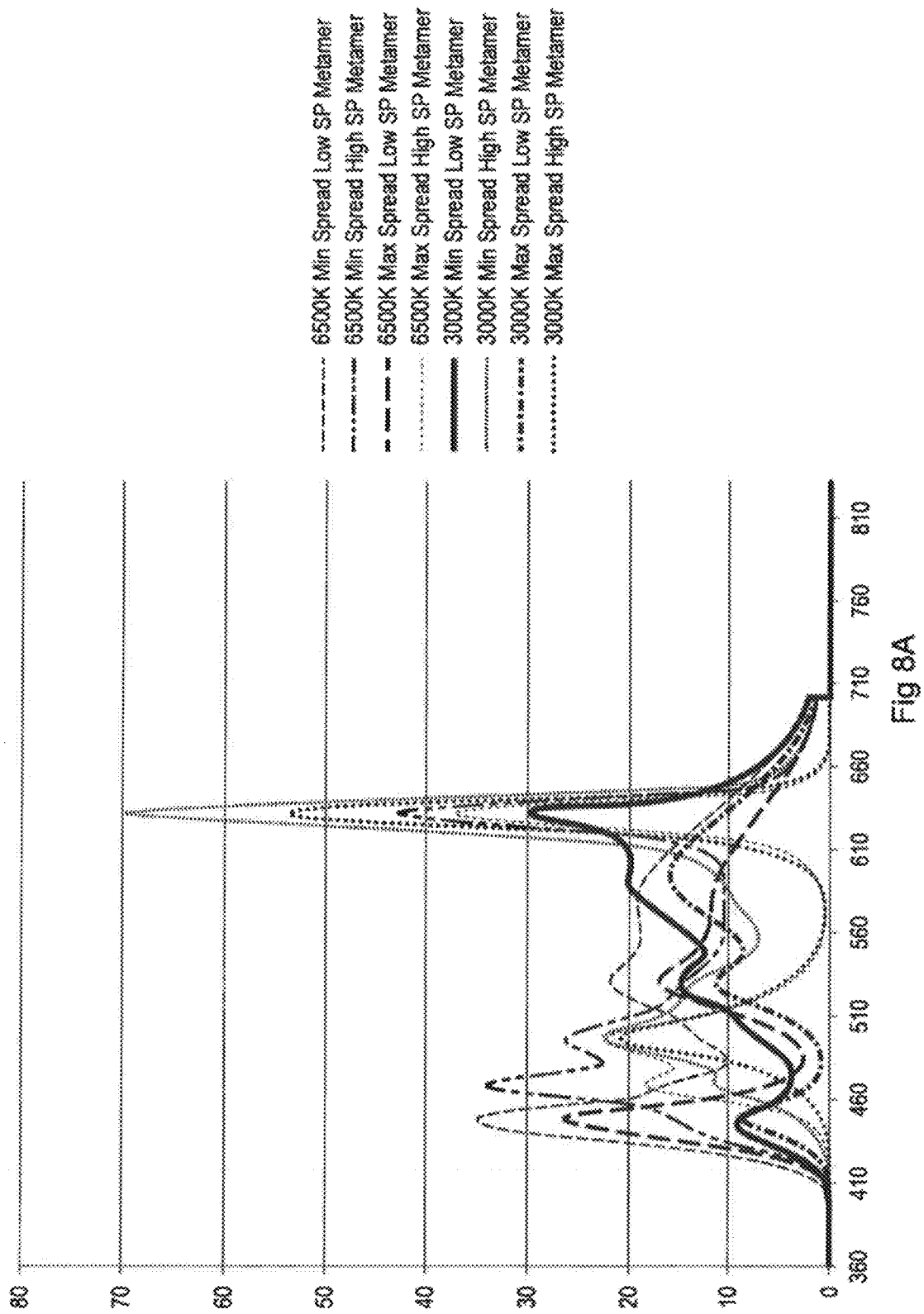
Figure 8D:
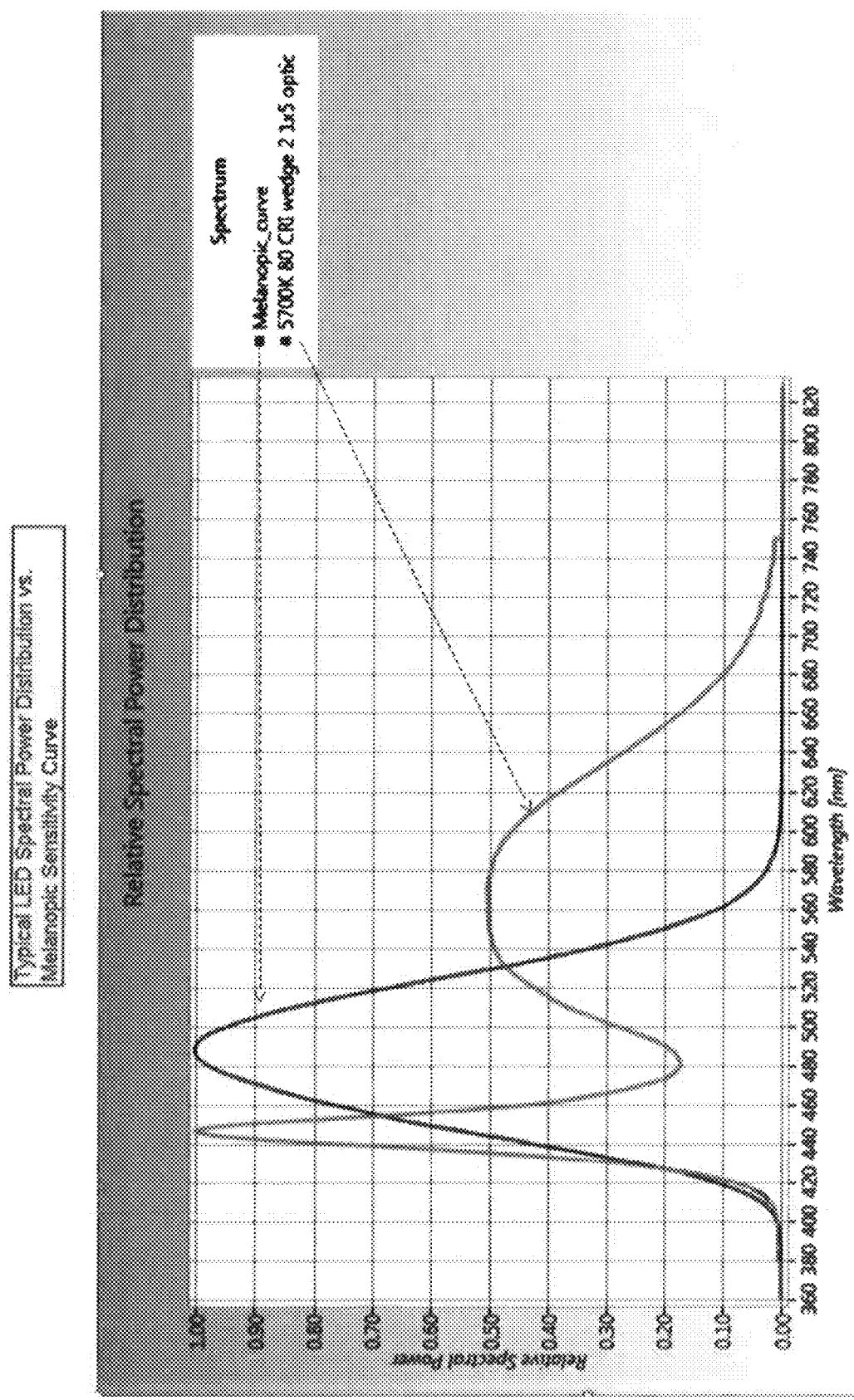
FIG. 8D illustrates a typical LED SPD vs the Melanopic sensitivity curve.
Figure 8E:
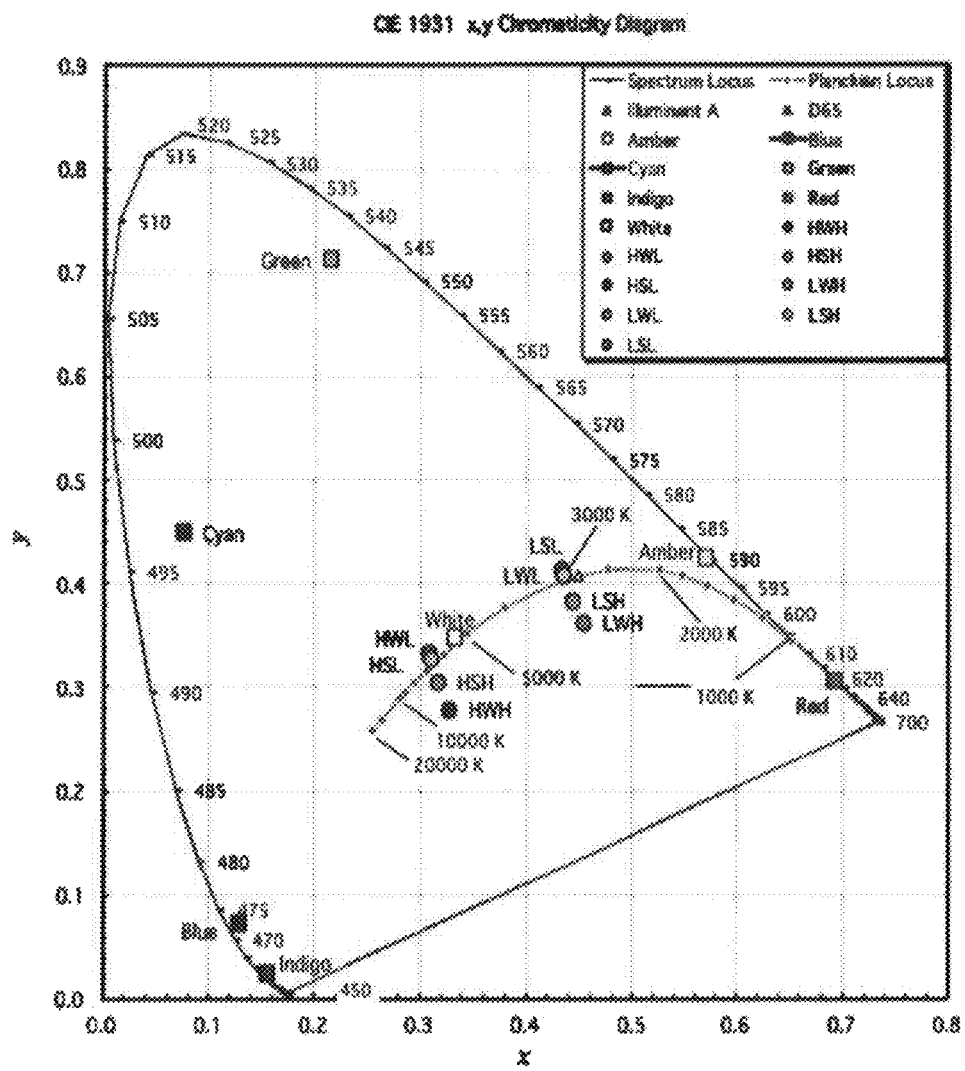
FIG. 8E illustrates the seven light sources and resultant metamers from FIGS. 8A-B located on the 1931 CIE chromaticity diagram.

As such, according to a first step 1001 of a method 1000 (FIG. 10), a lighting designer or other person determines desired color properties of the envisioned high melanopic content LED lighting system. Said lighting designer or other person may evaluate the general purpose of the lighting system (e.g., sports lighting, office lighting, façade lighting, street lighting) or a task to be performed thereunder (e.g., sports with high speed traveling objects such as baseball, high detail assembly work, general office work). This helps to inform what kind of white light is to be employed. Conceptually, one may consider the typical CIE chromaticity diagram with which one of average skill in color science is accustomed. A "white" source is generally considered to be anywhere along the blackbody curve (i.e., Planckian locus—see FIG. 8E); a metameric pair would comprise one source on one side of the curve directly opposite one source on the other side of the curve. Practically speaking, a "white" metameric pair is generally considered to be relatively proximate the Planckian locus, in the range of 2 k-20 k CCT, and having equal stimulation of the cones at a DUV of ±0.03 with respect to the CIE chromaticity diagram; though this could differ and not depart from aspects according to the present invention. Table 1 illustrates color properties of several different light sources (including some developed according to aspects of the present invention) with corresponding M/P ratios.

TABLE 1

| Source | CCT | S/P | M/P |
| --- | --- | --- | --- |
| High Pressure Sodium | 1960 | 0.63 | 0.24 |
| High Pressure Mercury | 2970 | 0.81 | 0.29 |
| Warm White | 2850 | 1.03 | 0.43 |
| Warm White | 2900 | 1.09 | 0.47 |
| Metal Halide 27k | 2650 | 1.16 | 0.53 |
| Metal Halide 32k | 3320 | 1.36 | 0.63 |
| Metal Halide 30k | 2910 | 1.38 | 0.65 |
| Metal Halide 37k | 3440 | 1.48 | 0.70 |
| Metal Halide 40k | 3880 | 1.54 | 0.73 |
| Lite White | 4250 | 1.49 | 0.70 |
| RE Compact Fluorescent | 3170 | 1.19 | 0.48 |
| White Fluorescent | 3540 | 1.26 | 0.56 |
| Ultralume Fluorescent | 3130 | 1.28 | 0.55 |
| Cool White | 4060 | 1.30 | 0.57 |
| LED Roadway Light | 5010 | 1.68 | 0.79 |

TABLE 1-continued

| Source | CCT | S/P | M/P |
| --- | --- | --- | --- |
| LED Lamp | 5500 | 2.09 | 1.11 |
| Daylight Fluorescent | 5140 | 2.09 | 1.07 |
| Fluorescent 65k | 6380 | 2.26 | 1.18 |
| GE75 | 9530 | 2.62 | 1.43 |
| M/P LED | 17000 | 3.31 | 1.66 |
| M/P LED | 5700 | 2.51 | 1.18 |

If desired, additional color properties could be considered according to step 1001 of method 1000. For example, if an identified task requires accurate color rendering, a lighting designer or other person may opt to also define a relatively high (e.g., ≥60) color rendering index (CRI).

According to a second step 1002 the desired melanopic content is chosen. Why one may choose one melanopic content may depend, at least in part, on manufacturability. In the current state of the art white light is produced by combining several RGB-type LED chips (also referred to as semiconductors) under the same primary lens; alternatively, discrete single-chip RGB LEDs can be placed in close proximity and used with an appropriate optic to "mix" the light. Alternatively, an LED designer could select a phosphor material to coat the primary lens such that light emitted by the chip is only partially transmitted; some is absorbed by the phosphor and re-emitted. The classic example is a blue LED with a yellow phosphor which emits a "white" color light, albeit one deficient in red. In both these approaches in the art LED designers continue to overlook a key portion of the spectrum (around 480 nm)—a portion once widely thought to be a waste of efforts (because of no known benefit to acuity, color rendering, etc.), but now understood to be critical to activating the melanopsin receptor; see e.g. FIG. 8D.

It is believed that the exemplary metamers reported on in the last two rows of Table 1 can be produced using state-of-the-art practices relating to phosphoring.

Following step 1002, step 1003 comprises verifying CCT and color rendering of the high melanopic content LED. FIGS. 3E-3CC show views from a calculation tool which could be used in step 1003.

A fourth step 1004 comprises establishing an equivalent perceived brightness between the high melanopic content LED and corresponding low melanopic content LEDs. As previously discussed, the recently discovered melanopsin receptor—more specifically, the melanopsin intrinsically photosensitive retinal ganglion cells (ipRGCs)—has been observed to impact perceived brightness. Perceived brightness, as previously stated, is not the same as luminance or illuminance (despite confusing language in some industry sources). Perceived brightness is understood in accordance with IES #1 and #2 and calculated for the high and low melanopic content LEDs according to Equation 1.

$$LUX_{LED1}/LUX_{LED2} = [M/P_{LED2}/M/P_{LED1}]^{0.32} \quad \text{Equation 1}$$

where: Lux is measured photopic luminance

So taking two values within a CCT (here, 9.0 and 9.5) and knowing at least one photopic illuminance (e.g., as may be measured using commercially available light meters—here, 100 lux), one can calculate the equivalent brightness in the other source according to Equation 1. This can be verified with the aforementioned true brightness meter.

Example Calculation Using Equation 1

$M/P_{LED1} = 9.0$ $M/P_{LED2} = 9.5$ $LUX_{LED1} = 100$ lux $100 \text{ lux}/LUX_{LED2} = [9.5/9.0]^{0.32}$ $LUX_{LED2} \approx 98.28$ lux Knowing the photopic illuminance of both the high and low melanopic content LEDs to keep a constant perceived brightness, one may determine an appropriate power input to achieve said illuminance (i.e., the current needed to power the LED at the appropriate light level). As is well known in the art, the number of LEDs and their wiring configuration (e.g., series versus parallel) could impact the current supplied to each LED and, therefore, impact the light output. LED manufacturers publish a variety of test data and information on their products which makes the determination of a power input to get a photometric output a relatively straightforward calculation; though, of course, a light meter could be used to verify the LEDs are operating at the desired photopic illuminance for the task/environment.

So it can be seen that method 1000 sets forth a more comprehensive way of designing high melanopic lighting systems as compared to state-of-the-art practices insomuch that not only is color considered (i.e., the cone response), and not only is brightness considered (i.e., the rod response), and not only is the non-visual response considered (i.e., the melanopsin response), but all three are taken into account—and in a manner that maintains a perceivably constant color and brightness. Method 1000 may be embodied in a variety of apparatuses so to produce a high melanopic content LED lighting system (i.e., providing both general purpose lighting and circadian lighting); one such apparatus is illustrated in FIGS. 9C and D.

Figure 9C:
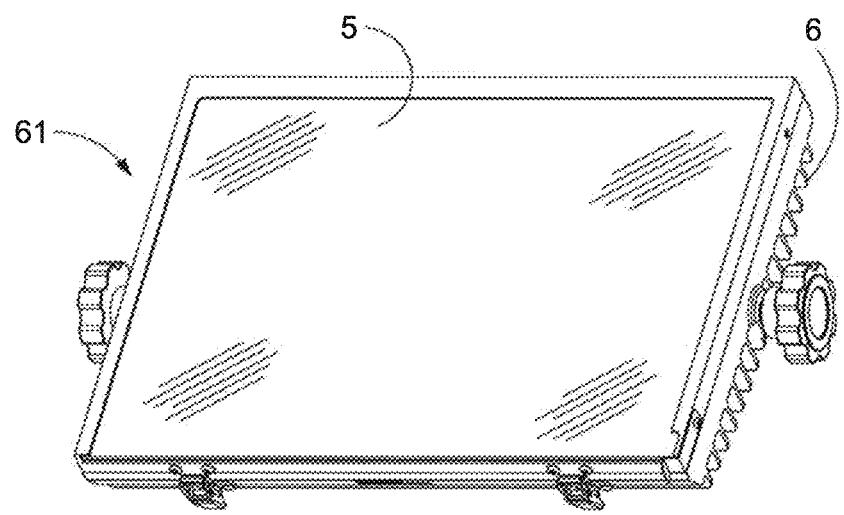
Figure 9D:
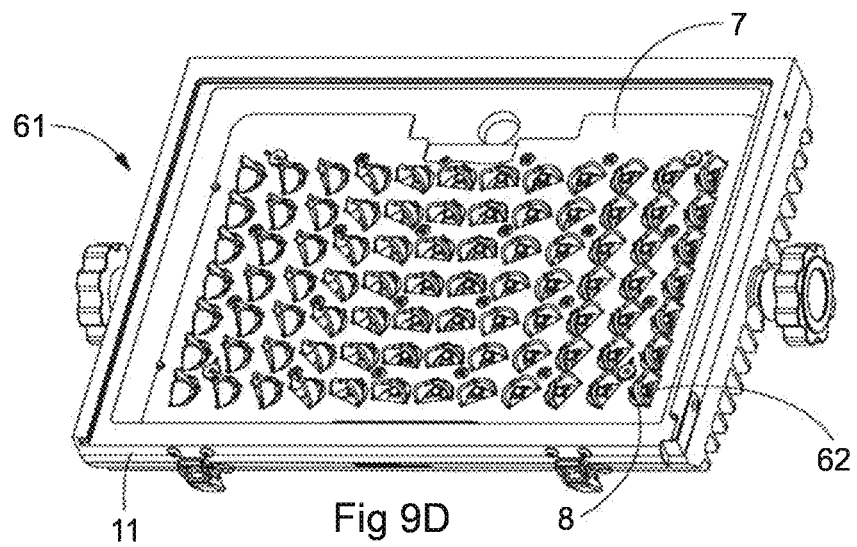

As can be seen from FIGS. 9C and D LED fixtures 61 generally comprise an array of LEDs; here 84 having high melanopic content.

LED fixture 61 further comprises a fixture housing constructed of aluminum (or other thermally conductive alloy) with integral finned heat sink 6, which together with a hinged lid 11 with transparent lens 5 encloses the LED light sources and optics panel 7 with interchangeable optics 8. LED fixture 61 could be used with a variety of support structures so to enable operation in a variety of environments or for a variety of tasks.

If desired for any reason such as for circadian lighting systems, given a luminaire with two sets of LEDs having different CCTs, and knowing the photopic illuminance of both the high and low melanopic content LEDs to keep a constant perceived brightness, one may determine an appropriate power input to achieve said illuminance (i.e., the current needed to power the LED at the appropriate light level). As is well known in the art, the number of LEDs and their wiring configuration (e.g., series versus parallel) could impact the current supplied to each LED and, therefore, impact the light output. LED manufacturers publish a variety of test data and information on their products which makes the determination of a power input to get a photometric output a relatively straightforward calculation; though, of course, a light meter could be used to verify both the high and low melanopic content LEDs are operating at the desired photopic illuminance for the task/environment. Once the light output for both sources is known, and once the power input to achieve said light output is known, one may establish a power profile according to step 1005 of method 1000, FIG. 10. Said power profile could be readily implemented via software or communicated from an offsite position to a controller board for an associated subset of LEDs. Said power profile could transition from the high melanopic content LEDs to the low melanopic content LEDs according to some regular period (e.g., a 1% power input change resulting in some fractional luminous output change every several minutes), on demand (e.g., via manual power adjustment member such as a rheostat), or otherwise. One possible operational profile from transitioning from the high melanopic content LEDs to the low melanopic content LEDs is set forth in Equation 2.

$$(F_{LED1}+F_{LED2})*[(F_{LED1}+cF_{LED2})/(F_{LED1}+F_{LED2})]^{0.32}=1 \quad \text{Equation 2}$$

where:
$F_{LED1}$=fractional photopic illuminance of the high melanopic content source calculated in Equation 1, and $0<F_{LED1}<1$
$F_{LED2}$=fractional photopic illuminance of the low melanopic content source calculated in Equation 1, and $0<F_{LED2}<c^{-0.32}$
$c=[M/P_{LED2}/M/P_{LED1}]$, and $\frac{1}{4}<c<4$ If desired, Equation 2 could be a timed function—namely, that power adjustments are made every few minutes during a time period defined by a user, in accordance with an existing building management system, or in accordance with local sunrise/sunset times, as a few non-limiting examples.

So it can be seen that method 1000 could be used to set forth a more comprehensive way of designing circadian lighting systems as compared to state-of-the-art practices insomuch that not only is color considered (i.e., the cone response), and not only are circadian rhythms considered (i.e., the biological/physiological response), and not only is brightness considered (i.e., the rod response), and not only is the non-visual response considered (i.e., the melanopsin response), but all four are taken into account—and in a manner that maintains a perceivably constant color and brightness. Method 1000 may be embodied in a variety of apparatuses so to produce a dual purpose LED lighting system (i.e., providing both general purpose lighting and circadian lighting); one such apparatus is illustrated in FIGS. 9A and B.

As can be seen from FIGS. 9A and B LED fixtures 61 generally comprises an array of LEDs; here 84 LEDs 62 wired in two parallel strings (with 42 LEDs each wired in series) but physically spaced within the fixture such that the LEDs alternate from high melanopic content to low melanopic content. So looking at FIG. 9B, the first LED in the upper left corner may be a high melanopic content LED, the next to it may be a low melanopic content LED, the next a high melanopic content LED, and so on. Alternating physical placement of the two subset of LEDs in this manner ensures the beam pattern and light uniformity (which is critical for general purpose and tasks performed thereunder) is maintained as the high melanopic content LEDs which are at full output in the morning are transitioned to low or no output in the evening (and vice versa for the low melanopic content LEDs). This sort of physical spacing does present some challenges in producing the LED board—namely, the positioning of the traces—but this could be overcome via use of jumpers. Also, control of two separate strings would require either two drivers or a single driver with two outputs, but these are readily commercially available and in many cases are still a lower cost option to a user than having to purchase a general purpose lighting system and a circadian lighting system.

LED fixture 61 further comprises a fixture housing constructed of aluminum (or other thermally conductive alloy) with integral finned heat sink 6, which together with a hinged lid 11 with transparent lens 5 encloses the LED light sources and optics panel 7 with interchangeable optics 8. LED fixture 61 could be used with a variety of support structures so to enable operation in a variety of environments or for a variety of tasks.

The invention may take many forms and embodiments. The aforementioned examples are but a few of those. To give some sense of some options and alternatives, a few examples are given below.

J. Options and Alternatives

The present invention sets forth method, apparatus, and systems for providing high melanopic content lighting.

With regards to the various formulas set forth, it should be noted that these could differ and not depart from at least some aspects according to the present invention. For example, since melanopsin/melanopic content is a relatively new concept in the field of vision science, it may be preferable to use a different ratio to represent the non-visual response to perceived brightness (even if not a perfect substitution under all testing conditions). As previously discussed, it has been found that representing melanopic content as S/P rather than M/P—where S represents the scotopic luminous efficiency function ($V'(\lambda)$) for a given light source having an SPD and is sourced from the Commission internationale de reclairage (CIE) assuming a standard observer angle of 2°—is acceptable in most scenarios with modification to the equations set forth above. In such an instance, Equation 1 would be modified to become Equation 3 and Equation 2 would be modified to become Equation 4.

$$LUX_{LED1}/LUX_{LED2}=[S/P_{LED2}/S/P_{LED1}]^{0.436} \quad \text{Equation 3}$$

where: Lux is measured photopic luminance $$(F_{LED1}+F_{LED2})*[(F_{LED1}+cF_{LED2})/(F_{LED1}+F_{LED2})]^{0.436}=1 \quad \text{Equation 4}$$

where:
$F_{LED1}$=fractional photopic illuminance of the high melanopic content source calculated in Equation 1, and $0<F_{LED1}<1$
$F_{LED2}$=fractional photopic illuminance of the low melanopic content source calculated in Equation 1, and $0<F_{LED2}<c^{-0.436}$
$c=[S/P_{LED2}/S/P_{LED1}]$, and $\frac{1}{4}<c<4$

K. IES #1

Brightness Judgments in a Simulated Sports Field Correlate with the S/P Value of Light Sources Bradley Schlesselman, Myron Gordin, Larry Boxier[1], Jason Schutz, Sam Berman[2], Brian Liebel[2] and Robert Clear[2]

Musco Sports Lighting, LLC, 100 1st Avenue West, Oskaloosa, Iowa 52577 1. Former employee, 2. Consultants Abstract:

Brightness perception in a simulated sports field was evaluated for photopically equal and constant color lighting but of different spectral content (metamers). A simulated sports field of dimensions 20×30 feet was constructed in an enclosed space and lit to the distribution of photometric conditions (both light and dark) approximating those measured at night in an operating full size illuminated sports field. Fifty-seven subjects comprising 3 age groups (18-30 years, 31-50 yrs and >50 years) were selected and sat in a chair positioned at an edge and midpoint of the simulated field, providing a binocular and unobstructed view of both the lit "field" and dark surround. The illuminance levels were 60, 150, and 400 vertical lux at eye level in the direction of gaze, corresponding to those measured for spectators and performers in an operating field. Subjects were Musco employees or their family that had no special knowledge in lighting and were unaware of the study purpose. The study utilized theatrical luminaires with multiple and different colored LED sources which could be combined to form four pairs of whitish metamers, each pair consisting of one metamer having a relatively higher S/P ratio compared to the other. Two pairs had relatively higher nominal CCT values than the other two pairs, and within each CCT set of metamers, one pair had a wide spread between the high and low S/P ratio metamer, while the other pair had a relatively smaller difference between the S/P ratios. The S/P values ranged approximately from 1.2 to 4 and the difference between the S/P values for a compared pair varied between 0.72 and 1.86. The conventional CCT values ranged from nominal 2700K to 6700K.

Subjects compared the perceived brightness of the illuminated field under each metameric pair where the illuminance measured at the eye was equal for each of the two sources within the compared pair. The comparison was judged while subjects viewed repeated switching between the paired lightings. Subjects were asked to focus on an iPad mini with a video image of a lava lamp placed in the middle of the simulated field, and judge which of the 2 lighting conditions appeared brighter. 47 Subjects completed this test that included all four metameric pairs at both 60 and 150 lux, and one pair at 400 lux, for a total of 423 total spectral comparisons. The result obtained was that 375 out of those 423 comparisons had the higher S/P value light sources chosen as the lighting that gave the illuminated field a brighter appearance. This result yields an unbiased estimate of 88.5%±1.6% in favor of the higher S/P as perceived brighter with a miniscule p-value or probability of chance occurrence of approximately $10^{-134}$. The results were highly significant for all age groups.

To establish a possible objective correlate associated with the brightness perceptions, pupil size was measured employing infrared pupilometry for two of the metameric pairs at the 150 vertical Lux light level for 40 subjects. Results showed that on average pupil sizes were significantly smaller for the higher S/P spectra under otherwise identical lighting conditions, and were also in quantitative agreement with past observations although not necessarily the causal factor in brightness perception.

Background:

Previous studies Berman et al (1990), Brown et al (2012), Royer & Houser (2012) have shown that in conditions of full field of view lightings of the same color but of different spectral content and also with equal photopic luminance (metamers) are not perceived as equally bright. Current understanding of these observations [Brown et al (2012), Ecker et al, (2010)] is that they are likely a result of the responses of the non-image forming melanopsin photoreceptor widely distributed in the retina of the eye and whose spectral responses are not included in the determination of photopic luminance. Earlier work by Berman et al (1990) and prior to the discovery of the melanopsin receptor correlated full field brightness perception with the spectral content of metamers by employing an empirically determined correlation based on the S/P value of the metamer spectral content. Later calculations showed that for polychromatic light sources typical of lighting practice that there was a very high correlation (over 99%) between the S/P values and the melanopic content of these sources [Berman (2008), Berman & Clear (2008,2014)]. Although recent research [Royer & Houser (2012)] determined that photopic luminance did not predict equal brightness perception for their metamers, it was also concluded that the use of S/P failed as the spectral factor for correlating their results leaving uncertainty as to both the mechanisms behind the brightness perceptions and a practical guidance for lighting practice.

Study Objectives:

Over the past several years Musco engineers noticed that their brightness perceptions of lit athletic fields appeared to depend on the spectral content of the lighting. Such perceptions could possibly be due to vision related color effects resulting from differences in source colors (Harrington 1954), or effects of differences in source melanopic content (Bailes 2010) or perhaps a concurrence of both effects. In view of the past research efforts described above it was the intent of Musco to conduct a study where the 2 visual percepts were separated and to first examine the non-color effects. Thus the objectives of this investigation were to provide a more rational explanation of the field observations in terms of the most current lighting and vision science.

Methods:

Description of Test Room:

In order to accomplish these objectives a test room was designed to provide a reasonable simulation of an existing athletic field. A recreational soccer field of dimensions 240 feet by 150 feet lit to conventional light levels was chosen as a typical real field from which to design the simulation. Measurements of vertical illuminance at the eye were taken at this representative field from the perspective of a player in the field and a spectator on the side, yielding nominal values of about 150 and 60 vertical Lux respectively corresponding to a range of 250 to 300 Lux of horizontal illuminance. The visual lighting perspective gained by a person standing on one side of the field and at the midpoint would provide a view with approximately ¾ of the total visual solid angle as essentially dark and the remaining lit by the field luminaires.

Figure 13A:
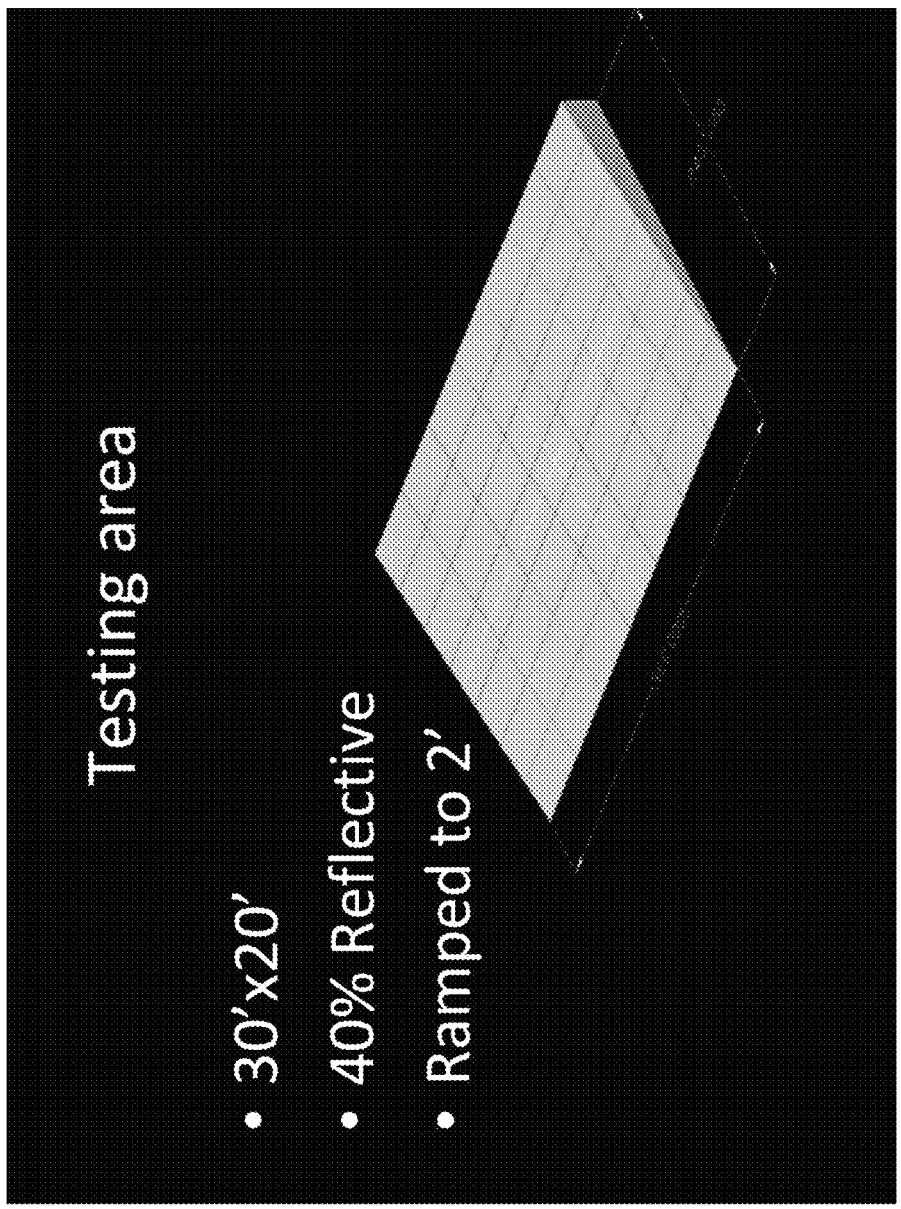
Figure 13B:
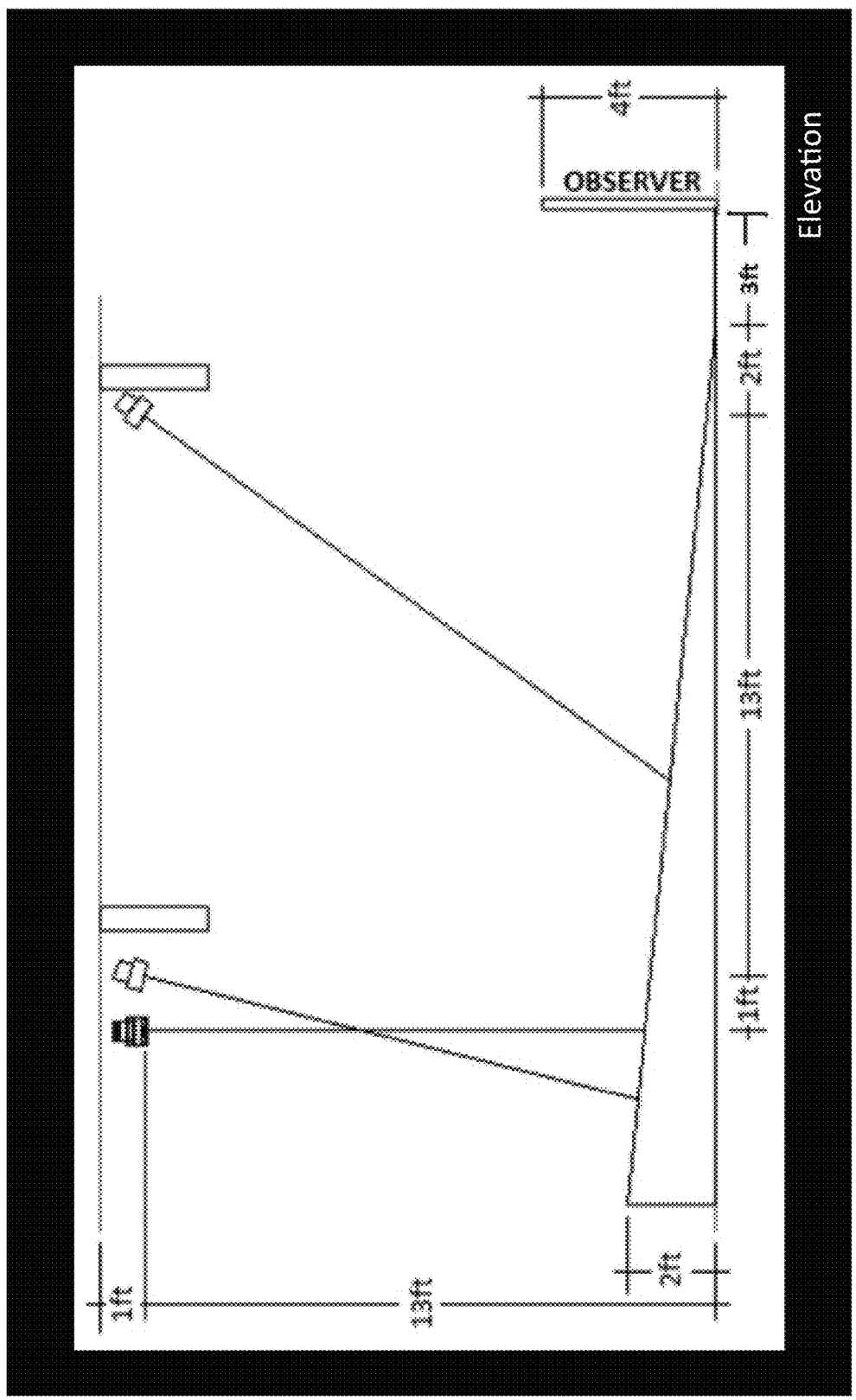

A 30' wide by 20' deep simulated test field was constructed inside a large hall, lit so that about ¾ of the visual solid angle was in the dark from the perspective of the subject situated at the midpoint of the longer dimension and at the front end of the shorter dimension. The design of the simulated field was based on actual field condition sight lines. FIGS. 13A, 13B and 13C show a perspective view of the simulated field construction, a cross-sectional drawing, and a photograph, respectively, of the test environment. The simulation of the field was accomplished by lighting only the lit portion of the test floor, which was painted a spectrally neutral, matte gray color and had an incline of 7.5 degrees to establish concordance in the end point viewing angle of the subject as would occur on the real field. The dark portion was obtained by using matt black fabric that was placed to surround the lit portion of the test space.

Achieving the necessary illuminance to simulate the field conditions required both direct lighting on the test field floor plane to yield a field luminance distribution approximating that of the real sports field, along with the addition of several overhead fixtures that provided the majority of vertical illuminance at the observer eye that would come from typical high mast sports lighting luminaires in real conditions. Attention was paid to assure that these overhead fixtures were not directly visible by the subject as well as to minimizing possible direct glare due to the proximity of these overhead fixtures in relation to the subject position (see FIGS. 13A-E).

Figure 13D:
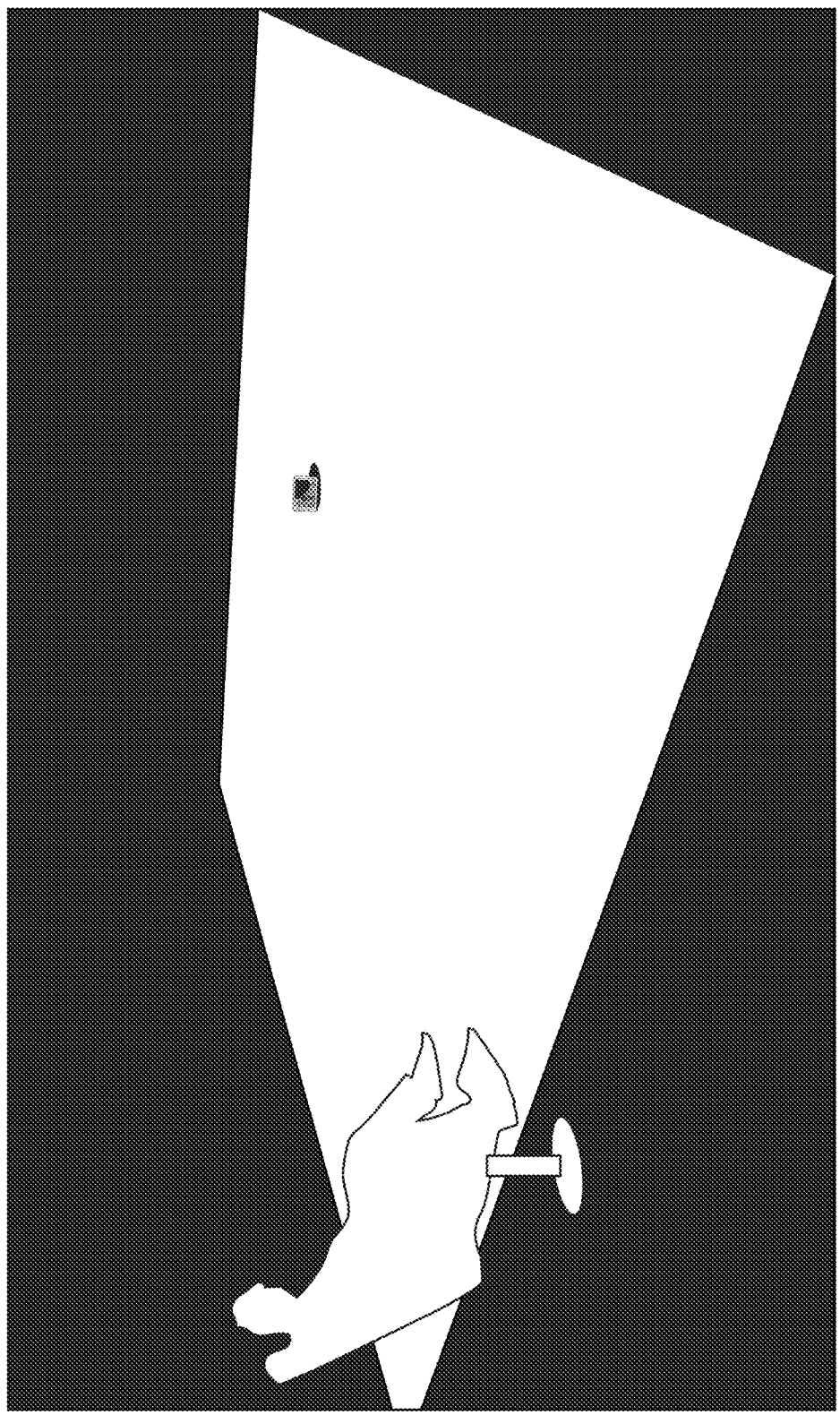

For the study, subjects sat in a chair at the midpoint of the long dimension at the edge of the lit floor as seen in FIG. 13C and viewed an iPad Mini tablet placed in line with center of the long dimension and at the middle of the lit floor. The iPad screen subtended essentially a foveal visual angle of about 3 degrees from the subject position and provided a fixation point. The iPad was set to display slow temporal screen variations by showing a simulated lava lamp scene of fixed color thereby helping to reduce boredom and to assure that the direction of gaze would be similar for all subjects. The iPad was placed in the center of a 12 inch diameter black circle (FIGS. 13C and 13D) and together these essentially foveal objects help to minimize the transient 'Maxwell Spots' that can be sensed in the central visual field when switching between test metamers and when the lit field of view extends much beyond the fovea. The person in FIG. 13D is outside the illuminated white area and, would be dark, but is shown in outline for clarity.

Lighting System:

The lighting for the test facility was provided by theatrical fixtures suitably placed so that the lighting distribution on the floor was uniform (10 fixtures), with an additional 5 fixtures adjusted to achieve the illuminance at the eye in the direction of gaze (DOG illuminance), namely the test values of 60 and 150 Lux. At maximum output it was also possible to achieve a higher value of approximately 400 DOG Lux and some testing was undertaken at that higher level.

Figure 13E:
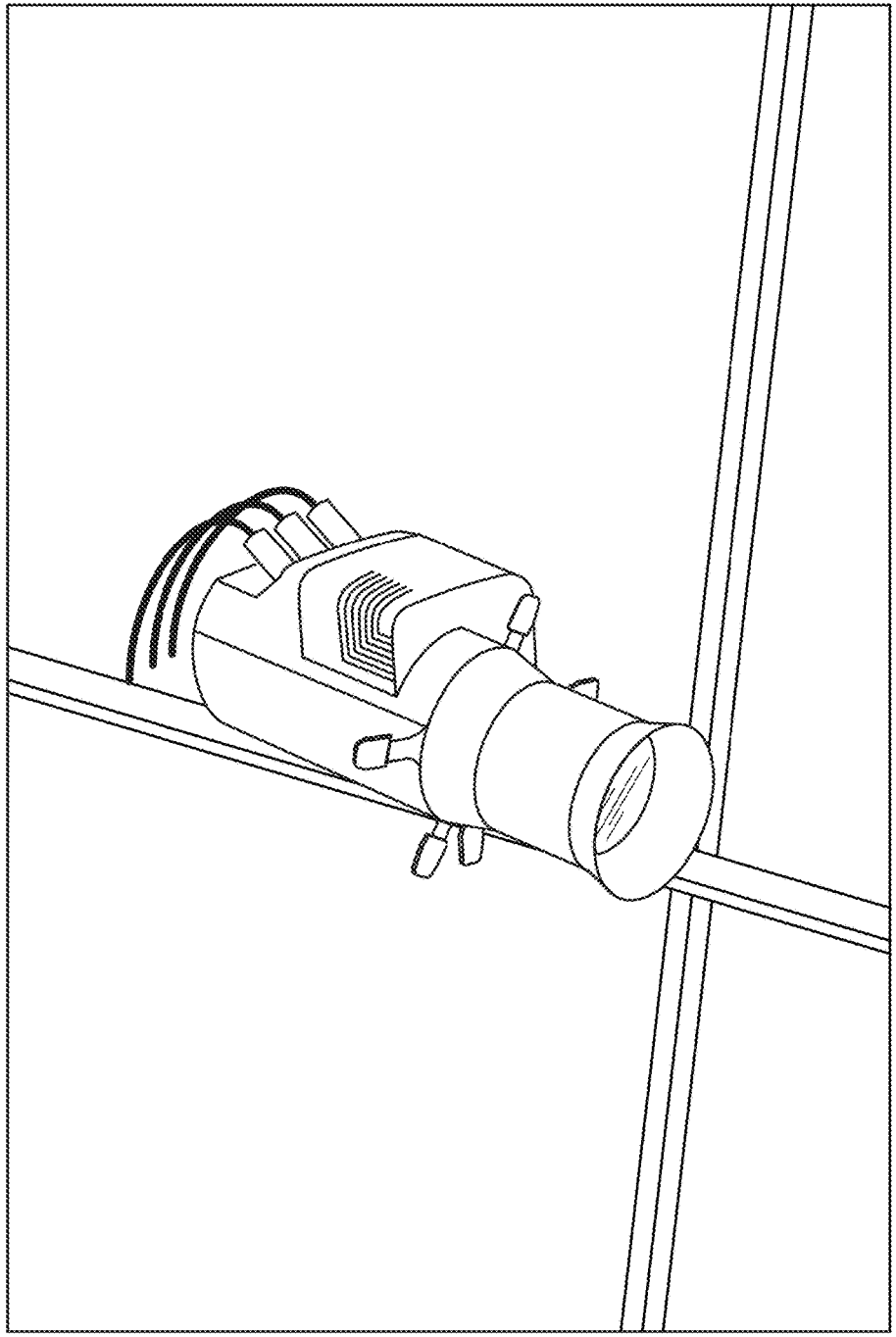

The fixtures were ETC Source Four LED theatrical luminaires with an array of 60 Luxeon Rebel emitters that consisted of 7 spectrally different colored LEDs (See FIG. 13E for a photo). The specific spectral power distributions (SPDs) were chosen so that several overall whitish metamers could be obtained but with different S/P content and CCT values (see section below on metamer design). A programmable DMX controller was used to yield the particular light levels and metamer combinations, where the LED light level output had a linear relationship with DMX value. The DMX controller allowed for rapid switching between metamers that would eventually be compared for brightness perception with a total transition time interval of 1 second. In addition the controller allowed metamerism to be maintained during the switching with a gradual shift in S/P values to its end point value by transitioning over 5 intermediate metameric stages each of 200-millisecond interval thereby minimizing transient perceptual effects.

Metamer Design:

The goal was to create whitish metamers of different melanopic spectral content or analogously different S/P spectral content as employed in the earlier studies by Berman et al (1990) and Brown et al (2012). Since color differences will contribute to brightness perception even at equal photopic luminance, the revealing of possible non-cone mechanisms requires that the viewed scenes of different spectral content have identical cone stimulation and therefore perceived color but have different melanopic or equivalently S/P content.

Typically source metamerism is determined by employing the conventional CIE color space such as the CIE 1931 2° or CIE 1964 10° observer color space and this was indicated as the procedure used by Royer & Houser (2012). There are however, deficiencies in the conventional CIE color matching functions when applied to forming perceived metamers that have been previously noted in the literature (Boynton 1996, Shaw 1999). In particular, Stockman & Sharpe (1996, 1999,2000) have presented an alternative color space that addresses those deficiencies. The cone fundamentals of the alternative color space are detailed in CIE (2006) "Fundamental chromaticity diagram with physiological axes—Part 1 Technical Report 170-1". For the purposes of this study metamerism is obtained by equal stimulation of those cone functions for the metamers and was determined for the 7 LED sources by employing the methodology described by Vienot et al (2012) as based on Cohen & Kappauf (1982, 1985). These constructions provide much superior perceived metamers when compared to constructions based on the CIE protocol of equal chromaticities.

Figure 13F:
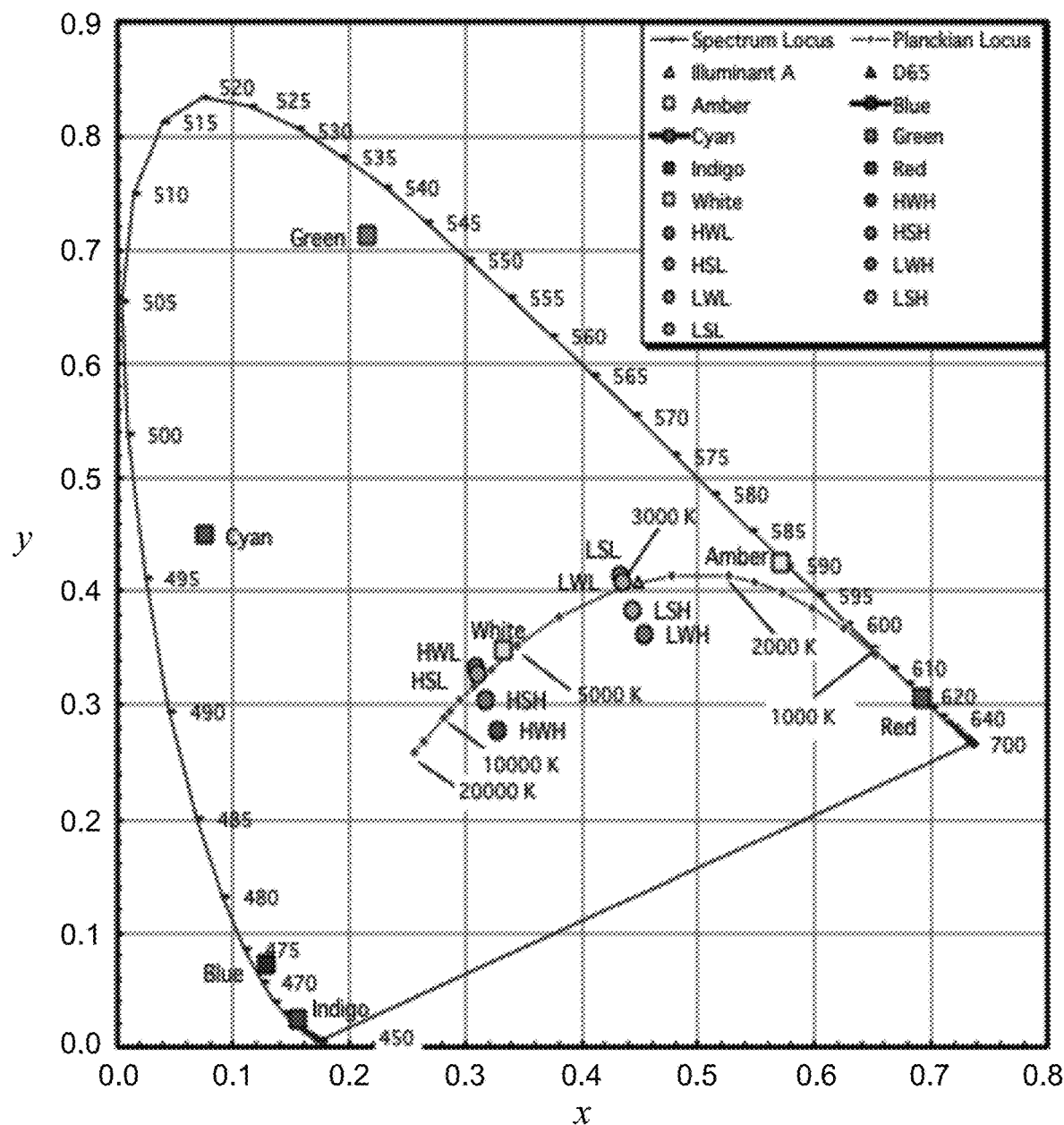

Note that the CCT values associated with the metamers and indicated in this study are calculated by employing the conventional CIE chromaticity system as applied to the SPD's of the test metamers and are referred to here as conventional or traditional CCT values. Since these test metamers do not have precisely equal CIE chromaticity values our calculated CIE CCT's will also be different for a compared metamer, but even so observers do not perceive color differences as metamers based on the Stockman/Sharpe functions are perceived as more identical. On the other hand, should alternate CCT values based on a color space employing the Stockman/Sharpe cone fundamentals be evaluated then those alternate CCT values would be identical for metamers constructed from those fundamentals. FIG. 13F shows the location of our metamers on a conventional chromaticity diagram where the slight shifts from chromaticity equality are indicated.

Figure 13G:
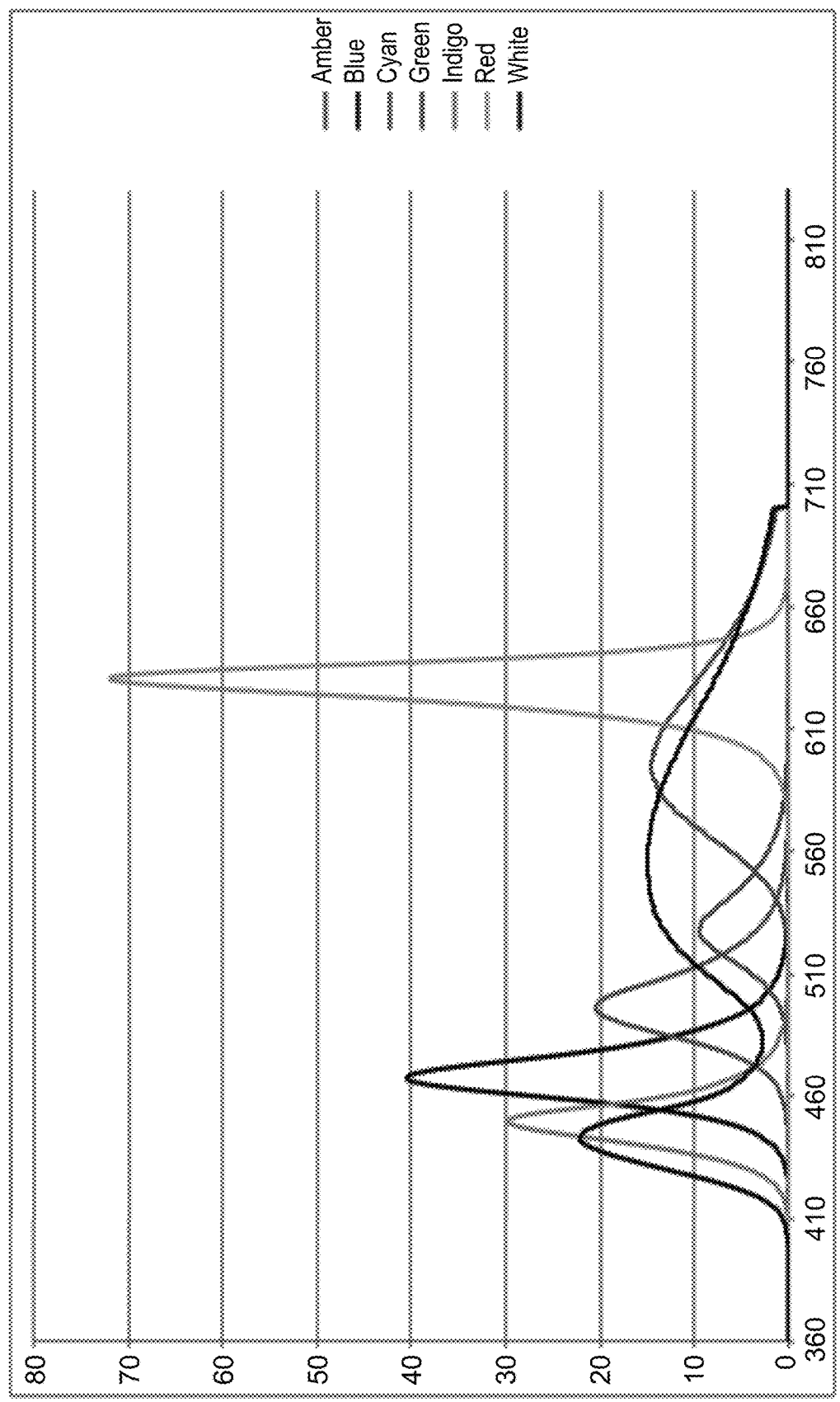

Four metameric pairs were constructed using the combination of LEDs within the ETC fixtures. The pairs were designed such that two pairs had a relatively higher conventional CCT than the other two pairs, and within each of the two pairs with differing conventional CCTs there was one pair with a wide spread between S/P values and one pair with a smaller spread between S/P values. The resulting metamers are described below in the following tables and figures:

Table 1 indicates the CIE x,y chromaticity coordinates of the (7) LED's and the resultant (8) metamers FIG. 13F shows the locations of Table 1 values on a conventional CIE chromaticity diagram FIG. 13G shows a graph of the SPD's of the (7) LEDs that compose the metamers and listed in Table 1

Figure 13H:
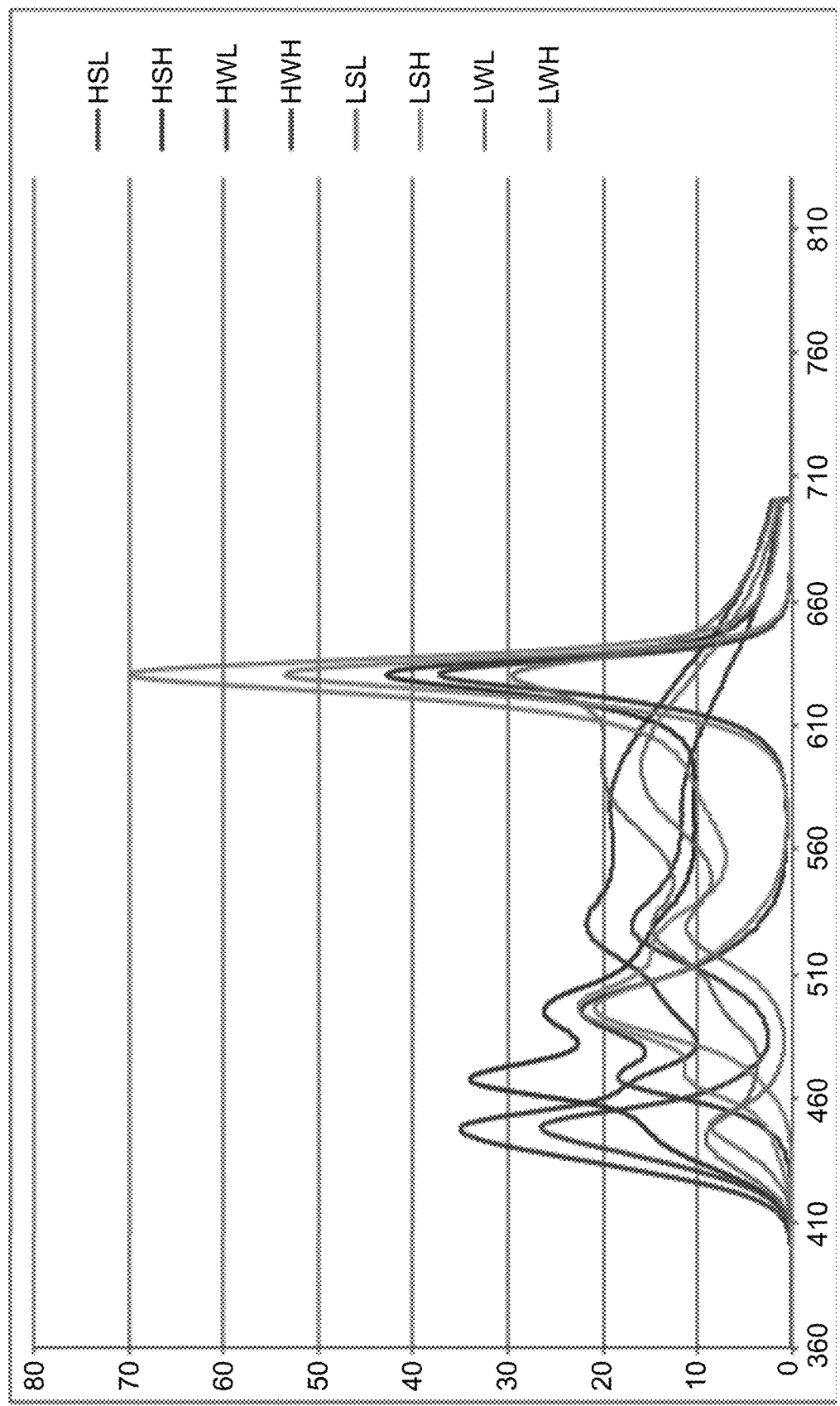

FIG. 13H shows a spectral graph of the (8) metamers listed in Table 1

TABLE 1

CIE x, y Coordinates of the seven LED sources and the resultant metamers.
CLE CHROMATICITY COORDINATES

| ETC LED Sources | | | x | y |
| --- | --- | --- | --- | --- |
| Amber | | | 0.5700883 | 0.4254393 |
| Blue | | | 0.1283426 | 0.0719665 |
| Cyan | | | 0.0747183 | 0.4494363 |
| Green | | | 0.2152694 | 0.7123734 |
| Indigo | | | 0.1549665 | 0.0244588 |
| Red | | | 0.6914472 | 0.3060068 |
| White | | | 0.3321667 | 0.3485219 |

| Metamer Pairs | S/P | Code | x | y |
| --- | --- | --- | --- | --- |
| Pair 1: High CCT | Hi | HWH | 0.3277019 | 0.25778902 |
| Wide S/P Spread | Lo | HWL | 0.3086062 | 0.3341716 |
| Pair 2: High CCT | Hi | HSH | 0.3167614 | 0.3053155 |
| Small S/P Spread | Lo | HSL | 0.3097961 | 0.3278254 |
| Pair 3: Low CCT | Hi | LWH | 0.4534897 | 0.3622677 |
| Wide S/P Spread | Lo | LWL | 0.4322281 | 0.4145167 |
| Pair 4: Low CCT | Hi | LSH | 0.4430859 | 0.3839001 |
| Small S/P Spread | Lo | LSL | 0.4348558 | 0.4085055 |

Lighting Conditions:

Each metameric pair was established, including the incremental steps, using the method described above. Once the fixtures were put in place to achieve the uniformity and Direction of Gaze (DOG) illuminance targets to simulate the sports field conditions, light measurements were taken to record the SPD and resultant S/P ratio and CCT of each metamer. Table 2 summarizes the measured values of the metamers:

TABLE 2

Lighting Conditions: Vertical DOG Illuminance, S/P values and CCT values

| Pair | Description | Code | Illuminance Levels 60 S/P | Illuminance Levels 150 S/P | Illuminance Levels 400 S/P | Illuminance Levels 60 CCT | Illuminance Levels 150 CCT | Illuminance Levels 400 CCT |
|---|---|---|---|---|---|---|---|---|
| 1 | High CCT Wide S/P Spread | HWH | 3.952 | 3.898 | | 5653 | 5475 | |
| | | HWL | 2.088 | 2.064 | | 6580 | 6380 | |
| | Delta | | 1.864 | 1.834 | | −927 | −905 | |
| 2 | High CCT Small S/P Spread | HSH | 3.087 | 3.009 | 2.937 | 6444 | 6224 | 5992 |
| | | HSL | 2.145 | 2.128 | 2.117 | 6706 | 6588 | 6434 |
| | Delta | | 0.942 | 0.881 | 0.820 | −262 | −364 | −442 |
| 3 | Low CCT Wide S/P Spread | LWH | 2.610 | 2.599 | | 2389 | 2373 | |
| | | LWL | 1.222 | 1.239 | | 3103 | 3149 | |
| | Delta | | 1.388 | 1.360 | | −714 | −776 | |
| 4 | Low CCT Small S/P Spread | LSH | 2.098 | 2.073 | | 2713 | 2688 | |
| | | LSL | 1.352 | 1.356 | | 3040 | 3054 | |
| | Delta | | 0.746 | 0.717 | | −327 | −366 | |

Lighting Measurements:

Throughout the testing procedure, lighting measurements were taken to ensure that light level and color consistency was maintained for each testing condition using a Gigahertz Model #BTS256-E BiTec Sensor Luxmeter. The meter was positioned to measure the vertical illumination at the eye in the Direction of Gaze (DOG illuminance), as well as the Spectral Power Distributions received at the eye. The S/P value was calculated from the measured SPD for each lighting measurement taken. The meter provided output data into a computer file that recorded the measurements for all tests, and these measurements were reviewed for each subject and for each test.

In some cases, the results of the light measurements showed departures from the constant value desired, including some cases where the recorded value was zero. During the data analysis, some subjects data did not meet the consistency required (constant DOG illuminance or S/P values, for instance), and those subjects were consequently excluded from the analysis. The consistency for constant illuminance and S/P values for the experiments was reviewed for both within and between subject analyses. The design of the test with regard to the lighting measurements was considered critical to ensure that the subjective judgments reported by the subjects was in fact based on the lighting values that were programmed into the lighting control system.

Subject Selection:

Subjects were volunteer Musco employees or their family members who satisfied general and normal visual behaviors but were rejected if such conditions as ocular disease, color blindness, or tinted contact lenses were present. In addition qualified subjects were not medicated regularly with pain reducers, especially opiates, and were over the age of 18 years. They were also briefly tested with an infrared pupilometer for a normal pupil response to changes in light level and were rejected if that was not the case. Those chosen were essentially naïve with no special knowledge of lighting and were unaware of the study purpose. A total of 57 subjects were tested. The distribution of these subjects is divided between three age groups as follows:

Age 18-30: 19 subjects
Age 31-50: 21 subjects
Age 51 & over: 17 subjects

The analysis of these subjects required that they completed testing for all conditions for each of the tests, 1) Brightness Comparison (BC); 2) Pupil Size (PS); and 3) Brightness Matching (BM), the latter being a separate study described in a separate paper. Due to some equipment errors in reading lighting measurements and/or obtaining pupil size data, the total number of subjects analyzed for each test varies. The total number of subjects analyzed for each test, by age group, and based on having complete data is as follows in

TABLE 3

Summary of Subjects in final analysis, by age group
TEST 1: Brightness Comparison (BC) Study:

| Subject Age Group | BC Test | PS Test | BM Test |
|---|---|---|---|
| Age 18-30 | 17 | 14 | 16 |
| Age 31-50 | 16 | 13 | 12 |
| Age 51 & over | 14 | 13 | 12 |
| TOTAL No. of | 47 | 40 | 40 |

General:

For this study all nine conditions shown in Table 2 were tested. All four metameric pairs were tested at 60 and 150 DOG lux, and one metameric pair (Pair 2) was examined at a much higher level of 400 Lax. The purpose of this latter test was to examine comparisons at a sufficiently high illuminance level where similarity of results would reasonably assure the absence of possible rod receptor effects. The comparisons were portioned by light level into these three illuminance categories. The 4 metamer comparisons in the 60 and 150 Lux conditions were presented in randomized order between subjects in each illuminance category. Subjects were informed that the lighting would be switched back and forth between 2 scenes and they would be asked to indicate which of the 2 scenes appeared brighter.

Protocol:

Each subject was adapted to the first condition in each of the categories for a period of 2 minutes focusing on the iPad mini. Subsequently the two viewed scenes are alternated with the viewing time for each scene totaling the sum of the Transition Interval of 1 second and an Observation/Decision Interval of 5 seconds for a total time of 6 seconds. Each time the scene was presented, the experimenter called out the scene as "A" or "B", and after 3 repetitions of each pair, the experimenter asked the subject to report which one is brighter recording the subject's decision in the computer. Subjects were not allowed the choice of "No Difference". This resulted in an approximate total time for a given subject for each pair as 6 seconds×6 presentations)+a few seconds decision time totaling about 1 minute.

Light measurements for each subject were made during the initial 2-minute adaptation period (condition A), and then once again during the $3^{rd}$ presentation of condition B, just before the subject made their final decision. The decision was recorded as 'A' or 'B'. The experimenter was not informed of which metamer was being presented during any of the tests other than the names 'A' or 'B'.

Test 3: Pupil Size Determinations:

General:

Since it had already been established that melanopsin stimulation is a significant factor in controlling pupil size [McDougal & Gamlin (2010), Vienot (2010), Tsujimura (2010)] it was reasonable to expect that there could be pupil size differences associated with the different metamers. The earlier studies on brightness perception mentioned above did not measure pupil size as a companion to the brightness perceptions but did show that lighting spectra with higher S/P (or melanopsin content) were perceived as brighter. By present understanding these brightness perceptions would be associated with smaller pupils and therefore less retinal illuminance, but nevertheless perceived as brighter. Thus, in order to fulfill the original study objectives, potential pupil size differences were examined. This was accomplished by employing an ISCAN infrared pupilometer.

Protocol:

In order to shorten the subject time and to answer the question of associated pupil size differences it was deemed sufficient to examine pupil responses at the 150 Lux condition with the following 4 comparisons.

Pair 2, Low S/P, 150 Lux
Pair 2, High S/P, 150 Lux
Pair 1, Low S/P, 150 Lux
Pair 1, High S/P, 150 Lux The following protocol was followed for each of the lighting conditions tested:

A 3-minute adaptation time was provided for each metamer prior to recording pupil diameter data. The subject was then instructed to maintain his/her gaze at the iPad. The experimenter also recorded the light measurements from the Gigahertz light meter during this adaptation time. After adaptation time was completed, pupil diameter data was recorded for 30 seconds. The experimenter then switched the lighting to the next lighting condition and repeated the process.

When these 4 tests were completed the experimenter closed the session. The data collected for later analysis of pupil size behavior consisted of a continuous 10-second blink free sample from each 30-second pupilometer readings.

Results:

Data Output and Analysis:

Two computer data files were produced for each subject, one which was custom-programmed software that captured the data from the Gigahertz light meter for all steps of the testing, and the other that captured the pupilometry data from the ISCAN pupilometer. Both files for each subject provided output in a standard format such that a third independently written Subject File program for data collation was developed, which imported each of these two files and provided a summary of the data in a more usable format.

The data for each subject was scrutinized to determine if any of the recorded light levels or S/P values were out-of-bounds relative to the constant values in Table 2 for the BC and also for the follow-on BM tests. The Subject File also automatically determined if there was a valid 10-second section of pupilometry for each subject. This data inspection provided the necessary step to determine what, if any, data could not be used on account of unanticipated lighting changes that occurred during the test. Furthermore, if the recorded light measurements were some value that was not consistent with the test parameters, those results could not be attributed to the test conditions and thus that data was considered unreliable and not usable.

The results of the data analysis concluded that occasionally there were some failures of equipment or a light level was not recorded resulting in incomplete or not verifiable data. The following criteria were adopted as a pre-condition for excluding that data.

Exclusions for the BC test:
Either preset A or B inadvertently records a zero illuminance value
Preset A or B was significantly different than the reference light level (60, 150 or 400 lux)
Any measured S/P value differed from the programmed value by 0.05 or greater.

Exclusions for Pupilometry:
Pupilometry data is excluded for those cases where BC and BM data is excluded.
The measured light level and/or S/P value was significantly different than the correlating measured light levels employed for the follow-on BM measured values.
A continuous 10 second blink free period of pupilometer data could not be found.

The result of applying these exclusions provided valid data for 47 subjects for the BC tests and 40 subjects for the pupilometry measurements.

Brightness Comparison Summary: The dependent variable in the brightness comparison study is the frequency with which the higher SIP source was chosen as brighter in comparison with the lower S/P source. There were a total of 423 runs, spread over the 9 conditions shown in table 2, and over 3 age groups: 18-30, 31-50 and 51 and older. The number of subjects in each age group was 17, 16 and 14 respectively. The results can be analyzed in terms of the entire population, and as a function of the ratio of the S/P ratios, the illuminance at the eye, and the age of the subjects.

The test over all conditions confirmed that there is an effect of the S/P ratio difference. The higher S/P source was perceived as the brighter source in 375 of the 423 runs. The unbiased estimate of the probability is 88.5%±1.5% (n=#brighter, N=total # of runs, mean=(n+1)/(N+2), SE=√[n+1)(N+1−n)/(N+2)(N+3)^2]). The probability that the true mean is 50% is on the order of $10^{-135}$, so the main hypothesis that the S/P ratio affects brightness is confirmed in this study.

The results were highly significant for all age groups and somewhat unexpectedly the oldest group had a somewhat higher percentage in favor of the higher S/P spectrum. As mentioned, testing was also performed at a high value of 400 vertical Lux where similar results were obtained lending assurance to the conclusion that the measured effects were unlikely due to possible rod receptor transients. The summary of results is listed in Table 4 at FIG. 14.

The variability of both S/P and illuminance over the various subject runs was very low. The maximum variation in S/P within a run was 5%, and the standard deviation of the S/P values for the runs averaged 1%. These variations are small relative to the differences in S/P between sources.

The maximum variation of the illuminances was under 4%. The average DOG illuminance for the low S/P source in each run was 0.3% higher than that of the higher S/P source. The higher S/P source had a higher photopic illuminance in only 21% of the runs, and the worst-case excess was only 1.9% (1.1 lux at 59 lux). These results are in the opposite direction of the hypothesis, and therefore do not represent the presence of a confounding condition.

Because of the methodology used to construct the metamers for the low and high CCT values it was not possible to perform unbiased estimation of the effect of CCT in the brightness comparisons.

Pupil Size Results Summary:

Pupil sizes were successfully measured for 40 of the 47 subjects that completed the BC tests for the 4 conditions at 150 Lux. For the wide spread in S/P values (ratio H/L=1.91) 37 of the 40 subjects showed smaller pupils for the higher S/P value and for the small spread (S/P=1.44) 32 subjects showed smaller pupils for the higher S/P value. On average these results confirm those of other pupil size measurements Berman et al (1992), MacDougal & Gamlin (2010), Tsujimura et al (2010), Vienot (2010) and further demonstrate that pupil size is affected by the S/P or melanopic content of the viewed spectrum. These results also show that even thought the photopic retinal illuminance is lower for the higher S/P spectrum (because of the smaller pupil size) the higher S/P spectrum is perceived as brighter.

Discussion:

For the conditions of the simulated athletic field with approximately ¼ of the complete visual field lit, reliable data from 47 subjects of ages ranging from 18 years to 60 years clearly showed a very significant and unequivocal effect on perceived brightness. They had a total of 423 opportunities to compare whitish metameric lightings of different spectral content and chose the spectra of higher S/P (or higher melanopic) content to be perceived as brighter 88% of the time even thought the photopic illuminance at the eye was unchanged. The metamerism provided by the use of the Stockman-Sharpe cone spectral sensitivities along with the application of the Cohen & Kappauf methodology allowed for the construction of many whitish metamers with nearly undetectable color differences by most subjects. In this manner the possibility of color confounds in the comparisons that might have occurred in other studies such as Royer & Houser (2012), especially when the difference in S/P values is small, have been greatly reduced.

Our results clearly demonstrate that for whitish lighting and when the lit field of view is extra-foveal, photopic illuminance is not the unique predictor of perceived brightness and that spectral content as described by the S/P value is also a necessary descriptor. Furthermore these results obtained under the modified conditions here, both compliment and extend the earlier results of Berman et al (1990) and Brown et al (2012). To the extent that the metamerism employed here is accurate, the comparisons evaluated are based on identical cone stimulation and thus the judgment differences cannot be associated with the predominance of any single cone receptor response such as an S-cone effect.

Figure 13I:
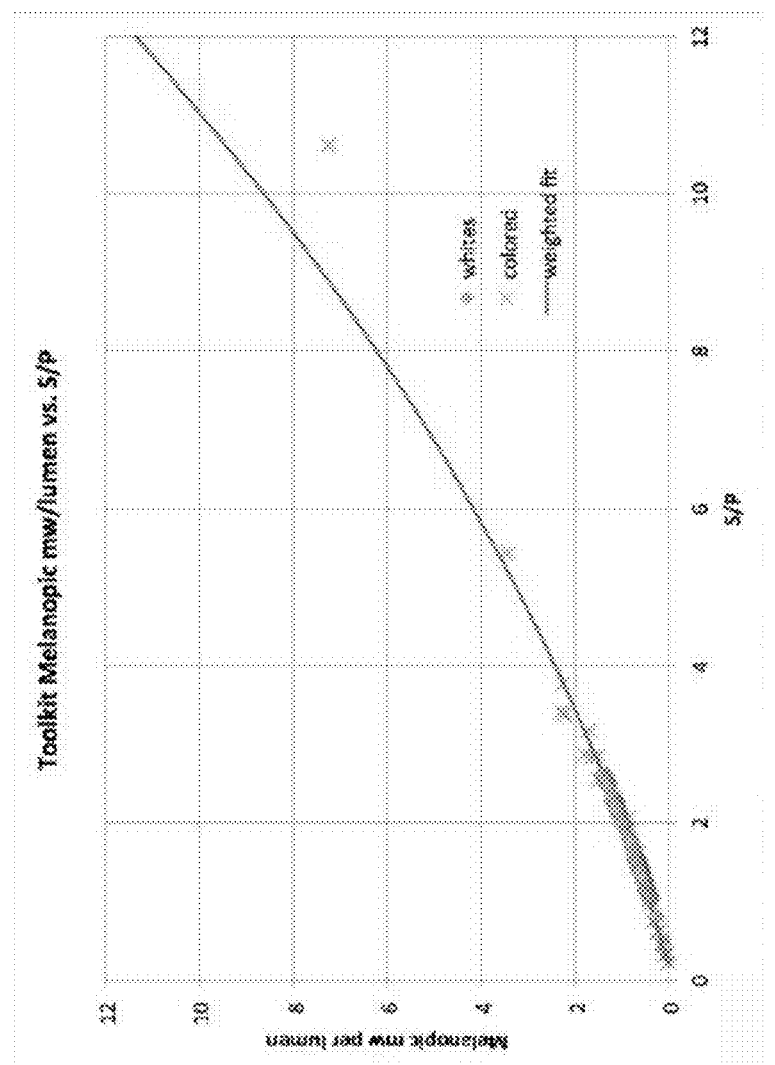

Presumably the underlying mechanism for the brightness perceptions is the result of the action of the retinal melanopsin receptors (Hattar et al 2002) whose spectral behavior when stimulated by polychromatic light sources is highly correlated with the ratio of scotopic to photopic S/P content of those sources [Berman (2008), Berman & Clear (2008, 2014)] thus allowing the S/P value as a marker of melanopic content. This high degree of correlation is shown in FIG. 13I (further described below) taken from Berman & Clear (2014).

Melanopic/lumen vs S/P Correlation: This graph shows the correlation between melanopic sensitivity and S/P value based on the spectral power distributions of a sample of 60 "white" light sources, and 28 color sources such as monitor colors. The S/P ratios of the whites ranged from 0.81 (a low color temperature high pressure mercury) to 2.62 (7500° K fluorescent lamp), while the S/P ratios for colors ranged from 0.23 (low pressure sodium) to 10.6 (LED monitor color blue). The fitted equation with a 99.4% correlation is given by Melanopic mw/photopic lumen (Mmw/P}=(0.041212*S/P+0.45827)*S/P−0.07428.

Range: 10.7>S/P>0.22.

Melanopic content is based on the melanopic sensitivity function. Lucas et al (2014), and given in the Tool Kit website.

The perceived brightness differences of this study are observed in a very short exposure time of a few seconds thereby reducing the dependence on memory load. Because of the switching protocol employed and the vagaries of memory, any accurate estimation of the long time stability of these brightness perceptions is essentially precluded. If melanopsin receptors are the underlying mechanism Do et al (2010) then the action time of the stimulating retinal pathways would be much shorter than the time course associated with the post illumination pupil response (PIPR) claimed as elucidating the typical response time for melanopsin receptors (McDougal & Gamlin, 2010). To the extent that our metamers are veridical and that rod receptors are not the underlying mechanism, our results indicate the likelihood of a rapid melanopic related response Peirson et al (2009).

The potential practical and economic consequences for lighting engineering that relate to the magnitude of this brightness effect are evaluated in the follow-on study of brightness matching.

References:

Bailes H J, Lucas R J. (2010). Melanopsin and inner retinal photoreception. *Cellular and Molecular Life Sciences,* 67(1), 99-111.

Berman S M, Jewett D L, Fein G, Saika G, Ashford F. (1990), Photopic luminance does not always predict perceived room brightness. Lighting Research and Technology 1990; 22: 37-41.

Berman, S. M., G. Fein, D. L. Jewett, G. Saika, and F. Ashford (1992). Spectral Determinants of Steady-State Pupil Size with Full Field of View. *Journal of the Illuminating Engineering Society,* 21(2) 3-13.

Berman, S M & Clear, R D; 2008; Past vision studies can support a novel human photoreceptor Light & Engineering Vol. 16, No. 2, pp. 88-94.

Berman, S. M; 2008, A new retinal photoreceptor should affect lighting practice Lighting Research and Technology; 40; 373.

Berman, S M & Clear, R D (2014) Implications of the Relationship between S/P and Melanopic Efficiency: Ilium Eng. Soc Conference report November, 2014

Boynton R M. (1996) *J Opt Soc Am A Opt Image Sci Vis.* August; 13(8):1609-21. Frederic Ives Medal paper. History and current status of a physiologically based system of photometry and colorimetry.

Brown T M, et al. (2012) Melanopsin-based brightness discrimination in mice and humans. CurrBiol 22(12):1134-1141.

CIE (2006) Fundamental chromaticity diagram with physiological axes—Part 1 Technical Report 170-1.

Cohen, J B and Kappauf, W E, (1982) Metameric color stimuli, fundamental metamers, and Wyszecki's metameric blacks. *The American Journal of Psychology* 95(4):537-64.

Cohen, J B and Kappauf, W E (1985), "Color mixture and fundamental metamers: Theory, algebra, geometry, application", American Journal of Psychology. 1985 Vol. 98, No 2, pp. 171-259.

Do M T, Yau K W (2010) Intrinsically photosensitive retinal ganglion cells. Physiol Rev 90(4):1547-1581.

Ecker J L, et al. (2010) Melanopsin-expressing retinal ganglion-cell photoreceptors: Cellular diversity and role in pattern vision. Neuron 67(1):49-60.

Harrington, R. E. (1954). Effect of color temperature on apparent brightness. J. Opt. Soc Hattar S, et al (2002) Melanopsin-containing retinal ganglion cells: Architecture, projections, and intrinsic photosensitivity. Science 295(5557):1065-1070.

Lucas, R., Lall, G., Allen, A. & Brown, T (2012). How rod, cone, and melanopsin photoreceptors come together to enlighten the mammalian circadian clock. *Prog Brain Res*, 199, 1-18.

Lucas R J, Peirson S N, Berson D M, Brown T M, Cooper H M, Czeisler C A, Figueiro M G, Gamlin P D, Lockley S W, O'Hagan J B, Price L L A, Provencio I, Skene D J, Brainard G C (2014) Measuring and using light in the melanopsin age. *Trends in Neurosciences* 37:1-9.

McDougal, D. H. & Gamlin, P. D. 2010 The influence of intrinsically-photosensitive retinal ganglion cells on the spectral sensitivity and response dynamics of the human pupillary light reflex. Vision Res. 50, 72-87.

Peirson S N, Halford S, Foster R G (2009) The evolution of irradiance detection: Melanopsin and the non-visual opsins. Philos Trans R Soc Lond B BiolSci 364(1531): 2849-2865.

Royer M P & Houser K W, (2012) Spatial Brightness Perception of Trichromatic Stimuli: Leukos Vol 9, No 2, (October) pp. 89-108

Shaw, Mark Q, (1999), Evaluating the 1931 CIE Color Matching Functions: A thesis submitted in partial fulfillment of the requirements for the degree of Master of Science in Color Science in the Center of Imaging Science, Rochester Institute of Technology June 1999

Stockman, A., & Sharpe, L. T. (1999). *Cone spectral sensitivities and color matching*. In K. Gegenfurtner & L. T. Sharpe (Eds.), *Color vision: From Genes to Perception* (pp. 53-87) Cambridge: Cambridge University Press.

Stockman, A. and Sharpe, L. T. (2000) *Spectral sensitivities of the middle- and long-wavelength sensitive cones derived from measurements in observers of known genotype. Vision Research*, 40, 1711-1737.

Stockman, A., & Sharpe, L. T. (2006). *Physiologically-based colour matching functions*. In *Proceedings of the ISCC/CIE Expert Symposium '06: 75 Years of the CIE Standard Colorimetric Observer* (pp. 13-20). Vienna: CIE Central Bureau.

Tool Kit:
http://lucasgroup.lab.ls.manchesterac.uk/research/measuringmelanopicilluminance/Tsujimura S, et al (2010) Contribution of human melanopsin retinal ganglion cells to steady-state pupil responses. Proc Biol Sci 277 (1693):2485-2492.

Vienot, F. (2010) The effect of controlled photopigment excitations on pupil aperture. Ophthal. Physiol. Opt 30: 484-491.

Vienot, F et al., (2012) "Domain of metamers exciting intrinsically photosensitive retinal ganglion cells (ipRGCs) and rods", Journal of Optical Society of America A, February 2012, Vol 29, No 2, pp. A366-A376.

L. IES #2

Brightness Matching Determines the Trade-Off Between S/P Values and Illuminance Level Bradley Schlesselman, Myron Gordin, Larry Boxier[1], Jason Schutz, Sam Berman[2], Brian Liebel[2], Robert Clear[2] Musco Sports Lighting, LLC, 100 1st Avenue West, Oskaloosa, Iowa 52577 1. Former employee, 2. Consultants Abstract:

In a previous Brightness Comparison study (BC Study, Schlesselman et al 2015), brightness perception comparisons in a simulated sports field were evaluated for photopically equal and constant color lighting (metamers) but of different melanopic content, as measured by the S/P ratio. In that study, subjects overwhelmingly judged the lighting with the higher S/P value as appearing brighter. In this companion study, 40 subjects who completed the previous study comprising the 3 age groups (18-30 years, 31-50 yrs and >50 years) sat in a chair positioned at an edge and midpoint of the simulated field, providing a binocular and unobstructed view of both the lit "field" and dark surround that simulates a real sports field. The subjects were provided with a means to adjust light levels to achieve an equality of perceived brightness. The illuminance levels were 60 and 150 vertical lux at eye level in the direction of gaze, corresponding to those measured for spectators and performers in an operating field. Subjects were Musco employees or their family that had no special knowledge in lighting and were unaware of the study purpose. The lighting utilized theatrical luminaires with multiple and different colored LED sources combined to form four pairs of metamers, each pair consisting of one metamer having a relatively higher S/P ratio compared to the other. Two pairs had relatively higher nominal CCT values than the other two pairs, and within each CCT set of metamers, one pair had a wide spread between the high and low S/P ratio metamer, while the other pair had a relatively smaller difference between the S/P ratios. The S/P values ranged approximately from 1.2 to 4 and the difference between the S/P values for a compared pair varied between 0.72 and 1.86.

The conventional CCT values ranged from nominal 2700K to 6700K. In order to achieve a condition of equal brightness perception, subjects were given repeated opportunities to adjust the level of one of the lighting conditions within a given metameric pair (randomly selected as the high S/P or low S/P source) by raising or lowering the light level with a manual dimming control slider to select a level where the 2 lightings appeared equally bright. This test was performed at two light levels (60 & 150 Lux) for each of the four metameric pairs. In this test, 92% of the 40 subjects chose to lower the photopic level of the higher S/P lighting to obtain an equality of brightness perception. Overall, the high S/P source was set to a lower light level than the low S/P source 293 times out of 320 runs, which has a probability of $10^{-151}$ of occurring by chance.

The amount of light level reduction was determined leading to an augmentation of the dependence of brightness perception on photopic illuminance P by the factor $P(S/P)^n$ The exponent n was empirically determined from the data as $n=0.436\pm0.017$.

The role of conventional CCT within each metameric pair was also examined and it was shown that there was no statistically significant effect.

In terms of practical applications for lighting engineering, these results show that substantial energy savings can be achieved by replacing sources with relatively low S/P values with e.g. LED sources capable of higher S/P values while maintaining the same brightness perception even in a night-time environment where only a fraction of the visual field is lighted. For example replacement in a lighted athletic field employing a typical MH source of S/P=1.4 by a LED source of S/P=2.4 would lead to the possibility of a 25% light level reduction based on the principle of equal perceived brightness. This feature is of sufficient magnitude that it should be a design consideration for sports lighting applications.

Background:

Previous studies Berman et al (1990), Brown et al (2012), Royer & Houser (2012) have shown that in conditions of full field of view lightings of the same color but of different spectral content and also with equal photopic luminance (metamers) are not perceived as equally bright. Current understanding of these observations [Brown et al (2012), Ecker et al, (2010), Lucas et al 2014] is that they are likely a result of the responses of non-image forming melanopsin photoreceptor widely distributed in the retina of the eye and whose spectral responses are not included in the determination of photopic luminance. Thus it is reasonable to expect that there could be a trade-off between melanopic content and photopic light level to achieve a given level of brightness perception. The quantitative aspect of this trade-off was not examined in the previous studies and as such is the primary objective of the present study.

Methods:

The testing took place in the same room as the BC study of brightness comparisons (Schlesselman et al 2015). The simulated sports field was constructed inside a large hall and had the dimensions of 30 by 20 feet (width and length). To simulate a realistic sports lighting situation, it was lit so that about ¾ of the visual solid angle was in the dark from the perspective of the subject situated at the midpoint of the longer dimension and at the front end of the shorter dimension. FIGS. 13A, 13B and 13C show a perspective view of the simulated field construction, a cross-sectional drawing, and a photograph, respectively, of the test environment. The simulation of the field was accomplished by lighting only the lit portion of the test floor, which was painted a spectrally neutral matte gray color and had an incline of 7.5 degrees to establish concordance in the end point viewing angle of the subject as would occur on the real field. The dark portion was obtained by using matt black fabric that was placed to surround the lit portion of the test space.

Achieving the necessary illuminance at the subject's eye required both direct lighting on the test field floor plane to yield a field luminance distribution approximating that of the real sports field, along with the addition of several overhead fixtures that provided the majority of vertical illuminance at the observer eye that would come from typical high mast sports lighting luminaires in real conditions. Attention was paid to assure that these overhead fixtures were not directly visible by the subject as well as to minimizing possible direct glare due to the proximity of these overhead fixtures in relation to the subject position (see FIG. 13D).

For the study, subjects sat in a chair at the midpoint of the long dimension at the edge of the lit floor as seen in FIG. 13C and viewed an iPad Mini tablet placed in line with center of the long dimension and at the middle of the lit floor. The iPad screen subtended essentially a foveal visual angle of about 3 degrees from the subject position and provided a fixation point. The iPad was set to display slow temporal screen variations by showing a simulated lava lamp scene of fixed color thereby helping to reduce boredom and to assure that the direction of gaze would be similar for all subjects. The iPad was placed in the center of a 12 inch diameter black circle (FIGS. 13C and 13D) and together these essentially foveal objects help to minimize the transient 'Maxwell Spots' that can be sensed in the central visual field when switching between test metamers and when the lit field of view extends much beyond the fovea.

The lighting system and the construction of the metamers are the same as in our previous study (Schlesselman et al 2015) and are described in detail there. As in our previous study achieving equal color of the compared lightings is obtained by assuring equal excitation of the 3 retinal cones accomplished through employing the Stockman cone fundamentals (Stockman et al 1999, 2000, 2006, CIE 2006) and not by equality of the CIE tristimulus values. Metamers are constructed using the methods described by Cohen & Kappauf (1982,1985) and Vienot et al (2012)

The same 7 LED sources and 4 metameric pairs as employed in the previous study are also used for this study. The CIE chromaticity values of these metamers are shown graphically in FIG. 13F below along with their spectral power distributions in FIG. 13H.

Lighting Measurements:

Throughout the testing procedure, lighting measurements were taken to ensure that light level and color consistency was maintained for each test. The light meter (Gigahertz Model #BTS256-E BiTec Sensor Luxmeter) also recorded the final light level reading for the matched brightness condition and provided the necessary readings to ensure that color consistency was maintained while the light sources were being dimmed. The meter was a positioned to measure the vertical illumination at the eye in the Direction of Gaze (DOG illuminance), as well as the Spectral Power Distribution curves received at the eye. The S/P value was calculated from the measured SPD for each lighting measurement taken. The same meter provided output data into a computer file that recorded the measurements for all tests, and these measurements were reviewed for each subject and for each test.

Subjects:

The same subjects as those who participated in the previous Brightness Comparison study participated in the brightness matching.

A total of 40 subjects completed the brightness matching with 16 in the younger than 30 years, and 12 each in the other 2 age groups.

Brightness Matching Protocols:

General:

Employing the same set of lighting conditions as in the BC study, subjects were given a manual slider control whose purpose was to adjust the light level of the 'B' condition to match the fixed 'A' lighting condition of the BC testing. Subjects were instructed to adjust the slider so that the 2 scenes would appear equally bright.

Specific Protocol:

To implement the matching the experimenter instructed the subject to move the slider to adjust light intensity of Scene B to match the brightness of Scene A (fixed) until the subject judged the two scenes to be equal in brightness. The scene of fixed illuminance was randomly chosen as either the high or low S/P condition. The subject was allowed to ask the experimenter to switch back and forth between scenes in order that they can further adjust the light level as many times as they wanted. Subjects were told to try to judge equivalency in a short time period following switching (close to 1 second, no longer than 5 seconds). After achieving equivalent brightness, the experimenter presents each scene for 5 seconds to confirm the equal brightness setting with the subject. The subject was allowed final tweaking if they change their mind after viewing the conditions under a longer exposure. The experimenter recorded the resulting DOG illuminance equivalency level with appropriate button push.

This process was repeated for each of the seven remaining pairs, with a 30 second adaptation time between each new pair within the light level, a five minute break between the light level changes from 60 to 150 Lux (between test 4 and 5). The subject time to accomplish this was approximately 30 minutes at most. Light measurements were recorded for each subject and for each condition.

Brightness Matching (BM) Results:

This test employed the same set of conditions as for the BC testing except the 400 Lux condition was not used due to the limitations of the light sources. Thus there were 8 different conditions (4 at 60 Lux and 4 at 150 Lux) as shown in Table 1 at FIG. 15. Thirty-nine of the 40 subjects were the same as those that participated in the BC study and the one additional subject was an excluded subject in the BC testing because of a failure to record the light levels.

Not all subjects chose a lower illuminance for the higher S/P source, and this reversal was more pronounced when the difference in S/P ratios between the two metamers were close. However, even in the worst cases (HS-60 and HS-150), 33 out 40 subjects used a lower illuminance for the high S/P source. The probability of this occurring by chance is 0.002%. For the wide spread in S/P values the worst case was 37 out of 40 and the best case was 40 out of 40. Thus there was a clear indication that the higher S/P sources required less illuminance to achieve the perceived brightness of the lower S/P sources. The summary of results is given in Table 2 at FIG. 16.

Statistical Analysis of Brightness Matching Study:

Forty subjects adjusted the brightness of a test light to match the brightness of a reference light. The lights were metameric in color, but differed in their S/P ratios. Each subject did 8 matches covering 2 reference illuminance levels at the eye; 60 and 150 lux, and 4 different sets of S/P ratios. An attempt was made to extend the illuminance range to 400 lux, but the apparatus did not have a sufficient illuminance range to allow brightness matches for all subjects, so this attempt was aborted, and the 400 lux data was dropped from further analysis. The subjects were grouped into age groups as in the study of brightness comparison, with the number in the age groups being 16, 12, and 12, respectively.

The average ratio of S/P values over the two sources for the eight runs ranged from 1.44 to 2.13. The maximum deviation from the average ratio within a run was two percent. The dependent variable in the brightness matching experiment i.e. the ratio of photopic illuminances for equal brightness perception, is a continuous variable, and is amenable to least squares fitting. We found that the fit to S/P ratios explains more of the variance than a fit to CCT (as computed in the standard XYZ space), and is therefore the preferred explanation for the results. We lastly show that there appears to be no interaction between S/P and CCT in these metameric matches.

The BC Study (Schlesselman, 2015) showed that subjects chose the high S/P source as being brighter than the low S/P of the same illuminance at the eye at a statistically significant level. In this Brightness Matching (BM) test this should translate into subjects choosing a lower illuminance at the eye for the high S/P source than for the low S/P source. With 8 runs for each subject, 32 of the 40 subjects chose a lower illuminance for the high S/P source than the low S/P source at a statistically significant level (7 out of 8 runs). Only one subject showed no preference (4/8). When averaged over subjects, the worst cases were for the two runs where the S/P ratio for the high to low S/P source was 1.44. Even for these two runs, 33 out of 40 subjects had a positive result (P=0.002%). Overall, the high S/P source was set to a lower light level than the low S/P source 293 times out of 320 runs, which has a probability of $10^{-151}$ of happening if the true probability was 50%.

Thirty-nine of the 40 subjects in the brightness matching study also had complete data for the BC study with the same sets of reference conditions. A comparison of the two studies highlights the variability of the results in the BC study. Of the 312 matching runs in the BC study, 26 of them had a negative result in that the low S/P source was judged brighter than the high S/P source. In the equivalent brightness matching experiment, only 9 of these conditions resulted in a negative result brightness match requiring a higher lux level with the high S/P source. The BC results did predict a difference in the average brightness matching illuminances. The 26 conditions with a negative brightness comparison had an average illuminance ratio of the low S/P source to the high S/P source of 1.036 (which is a slightly positive result). The 286 runs with a positive brightness comparison had an illuminance ratio of 1.29 on the brightness match, which is a strongly positive result.

A Model for Brightness Perception:

The main point of the BM study, other than demonstrating that there was an effect, was to identify the S/P exponent in the simple model of brightness dependence, i.e., $$\log B = \text{const} \times \log [P(S/P)^n] = \text{const} \times \log B_{br}.$$

where the "brightness lumen", $B_{br}$, has the simple form: $B_{br} = P \times (S/P)^n$.

In the BM study, the brightness of the reference source, $B_1$, is adjusted to achieve equal brightness of the test source, $B_2$. If we let r=S/P, then the log of the ratio of the illuminances is equal to a constant, n, times the log of the ratio of the S/P ratios: $\log(P_1/P_2) = n \log(r_1/r_2)$. A least-squares fit for n gives the value n=0.436±0.017.

This result is the principal quantitative determination for the BM testing.

The exponent is slightly smaller but reasonably close to that determined in the earlier study of Berman et al (1990) carried out in conditions where the full field of view was illuminated and where the exponent was determined there roughly as 0.5.

The age of the subject was close to significant in the BC study. We tested for an interaction of age and brightness exponent. Although the trend of the younger subjects appearing to have a lower exponent, the result was not statistically significant at the P=30% level. However, a similar test for the interaction of subject and exponent was significant at the P<0.01% level. Adding a subject interaction term increases the amount of variance explained by the fit from 17% to 47%, and slightly reduces the standard error of the exponent to 0.015. Subject exponents ranged from 0.061 to 0.0.922, and had a standard deviation about the mean of 0.185. Note the standard deviation appears to reflect a real variation in sensitivity to the S/P ratio among subjects.

The S/P value was also statistically significant in the BC study, but much of this effect should be caught in the analysis of the data in terms of the S/P exponent. The illuminance level was not a statistically significant effect in the brightness comparison study. Both factors are rejected in the analysis of exponent for the BM study.

Is there an Effect of CCT?

We examined the possibility of there being an interaction between S/P and color temperature by looking for a difference in the calculated S/P exponent in the high CCT versus the low CCT tests. A within subject comparison matching the illuminances, and the rough S/P ratios gave 160 differences between the high and low CCT runs. The difference of high-low CCT was 0.013±0.034, which is not statistically significant. We therefore rejected the hypothesis that there was an interaction between CCT and S/P in the perception of brightness in these metameric matches and conclude that there was no significant effect of CCT in the brightness matching study.

Limen Test: (Testing Subject Discerning Ability to Match Brightness)

Description:

The purpose of the limen test was 2-fold; the first is as a check that the equipment is functioning properly and second to evaluate the discerning ability level of the group of 40 subjects that successfully completed the BM test. That is, how good they are at being able to state that one condition can be adjusted to appear as having an equal brightness. To assess this ability to match alternating scenes for equality in brightness perception the limen test was performed. In this case the lighting for the 2 alternating scenes had equal spectral content with a nominal S/P value of 2.12 but where a test lighting of different DOG illuminance was to be adjusted by the subject with the slider so as to appear equally bright when compared with a standard scene of fixed illuminance. For the initial condition the test lighting was either 20% higher or 20% lower than the standard scene and alternated between successive subjects. Subjects then adjusted the test illuminance level with the slider until there was a match in brightness perception. The testing was done at the 2 standard levels of 60 and 150 Lux.

The detailed protocol was essentially the same as in the BM testing and is as follows. The subject was instructed to focus on the iPad Mini and allowed adaptation to the light condition scene A, which was the baseline illuminance, for 2 minutes for each of the 2 standard levels. After this period was complete, the experimenter alternated between scenes A and B, with the subject using the slider dimmer to adjust scene B to the level they felt was equal to scene A. Scene B light level was set at an increase or decrease of 20% and with the increased or decreased value alternating with each successive subject.

The subject could ask the experimenter to switch back and forth between scene A (fixed light level) and scene B (adjustable light level), with the reminder that the subject should try to judge equivalency in a short time period following switching (close to 1 second, no longer than 5 seconds).

After achieving equal brightness perception the experimenter presented each scene for 5 seconds and confirmed the equal brightness setting with the subject. The subject was allowed final tweaking if a final change was desired after viewing the conditions under the longer exposure. The experimenter then recorded the resulting equivalency light level with an appropriate button push.

Limen Test Results:

The mean difference in S/P of the test lighting from the reference lighting was 0.14%±0.13% for the 60 lux source, and 0.06%±0.08% for the 150 lux source. The maximum difference was 0.5% and 0.6% respectively.

One subject was unable to make a match within 70%, and was further unable to complete all of the brightness matching tests. This subject was not included in the analysis. Among the remaining subjects the maximum limen was 20%, while the overall subject mean limen was 0.7%±1.2% s.e. of the test illuminance. Thus the BM study results where the selected reductions amounted to around 20% can be considered as reliable and not arbitrary resulting from testing conditions being beyond their discerning capability and we can be reasonably confident that those differences obtained in the BM testing are well within the subjects' capabilities.

Discussion:

The purpose of the brightness matching was to determine the adjusted levels of photopic illuminance that would produce perceptual equality when the S/P values were different. The data showed that for the 40 subjects with 8 different lighting conditions, they chose on average to lower the light level of the higher S/P spectrum for 92% of the trials and depending on the condition this ranged from 83% to 99%. Thus we conclude that there is a trade-off between illuminance and S/P value, i.e. since a spectrum with a higher S/P value was perceived as brighter in the comparison study, its photopic illuminance can be lowered by an amount empirically determined that provides perceptual equality.

This result implies that there should be a quantitative relationship between a given amount of photopic illuminance difference and an associated difference in S/P value. To evaluate such a relationship the simple model introduced by Berman et al (1990) that followed on the classical luminance dependence of brightness perception was employed. In that model, brightness perception (B) would depend on luminance (P) as modified by the multiplicative factor $(S/P)^n$ where the exponent n is to be empirically determined. Since the classical luminance dependence of brightness perception is provided by a power law the inclusion of the S/P dependence is assumed to be extended by the equation $$\text{Log } B = \text{constant} \times [\text{Log } P(S/P)^n].$$

Thus if 2 spectra of different S/P values are perceived as equally bright at 2 different values of S/P then the above equation applied at equal values of B can be solved to determine a value for the exponent n.

With 8 lighting conditions and 40 subjects there were 320 opportunities to evaluate the exponent n. The analysis led to an overall exponent value of n=0.436±0.021 for the entire subject group covering all 3 age categories. There was no significant effect of age.

Correlated Color Temperature (CCT) Variations:

Prior studies evaluating brightness perception found that traditionally determined higher color temperature lighting was perceived as brighter Harrington (1954). But without control of S/P those comparatively higher CCT spectra associated with polychromatic light sources will generally have comparatively higher S/P values. Our premise is that these different brightness perceptions are a result of different S/P values serving as the spectral proxy for melanopic content (Berman 2008, Berman & Clear 2014, Brown 2012) and are not due, per se, to a pure CCT effect. In the studies performed here we attempted to examine whether there was a pure traditional (based on CIE chromaticity) CCT effect on brightness perception and in the selection of conditions traditional CCT was varied between nominal high around 6500K to low around 2700K. However, for the formation of the various metamers, we were not able to find a calculational procedure that allowed constant S/P value but different traditional CCT values as modifying CCT was always accompanied by a change in S/P under the constraint of our metamerism. This occurs because metamers constructed by employing the standard CIE procedure of equal chromaticity will have the same traditional CCT values as such metamers also have the same vector distance to the black body locus. However, as described above, the psychophysically improved metamers employed here do not have equal CIE chromaticities (see FIG. 13F) but alternatively they would have equal equivalent chromaticities in a color space based on the Stockman/Sharpe cone sensitivities. Nevertheless in the brightness matching study where the explicit dependence of brightness perception on S/P via its exponent could be determined, it was possible to test whether the exponent had different values depending on the condition of high or low traditional CCT. This evaluation yielded a difference in the exponent of 0.013±0.034, which is indistinguishable from zero and therefore we conclude that there is an absence of any significant traditional CCT effect on brightness perception.

Is the Protocol of Rapid Alternation Between Metamers Accounting for the Full Effect of Melanopsin Activation?

The results determined here are consistent with present understanding of melanopsin response from the point of view of an operative additional spectral sensitivity with a peak response in the bluish spectral region. The similarity of the results at three eye illuminances namely 60,150 and 400 Lux in the BC study lend support that the underlying mechanism is unlikely to be a direct response of rod receptors. On the other hand from the psychophysical approach employed here it is not possible to conclude whether the spectral effects are a result of a subset of rapid response melanopsin cells that are directly involved in this rapidly evaluated brightness perception. Since present understanding of melanopsin temporal behavior implies a slow response (McDougal & Gamlin (2010), Bailes & Lucas (2010), Do & Yau (2010), Ecker (2010) with time periods much longer than the few seconds employed in the switching protocol it is also possible that the full tonic response to brightness perception is not fully established here. Further studies would be useful to fully elucidate this concern. Perhaps a study performed in a steady state mode utilizing dichoptic viewing with visual field spectral optics adjusted to stimulate and allow comparison of non-overlapping cortical regions associated with each eye might provide further insight.

Implications for Lighting Practice:

In terms of practical applications for lighting engineering, the results of the BM study show that substantial energy savings can be achieved by replacing typical HID sources with their relatively low S/P values with e.g. LED sources capable of much higher S/P values while maintaining the same brightness perception even in a nighttime environment where only a fraction of the visual field is lighted. For example replacement in a lighted athletic field employing a typical MH source of S/P=1.4 by a LED source of S/P=2.4 would lead to the possibility of a 25% light level reduction (as measured with a standard light meter) based on the principle of equal perceived brightness and the exponent value of 0.436. This feature is of sufficient magnitude that it should be a design consideration for sports lighting applications.

REFERENCES

Bailes H J, Lucas R J. (2010). Melanopsin and inner retinal photoreception. *Cellular and Molecular Life Sciences*, 67(1), 99-111.

Berman S M, Jewett D L, Fein G, SaikaG, Ashford F. (1990), Photopic luminance does not always predict perceived room brightness. Lighting Research and Technology 1990; 22: 37-41.

Berman, S. M; 2008, A new retinal photoreceptor should affect lighting practice Lighting Research and Technology; 40; 373.

Berman, S M & Clear, R D (2014) Implications of the Relationship between S/P and Melanopic Efficiency: Ilium Eng. Soc Conference report November, 2014.

Brown T M, et al. (2012) Melanopsin-based brightness discrimination in mice and humans. Curr Biol 22(12):1134-1141.

CIE (2006) Fundamental chromaticity diagram with physiological axes—Part 1 Technical Report 170-1.

Cohen, J B and Kappauf, W E, (1982) Metameric color stimuli, fundamental metamers, and Wyszecki's metameric blacks. *The American Journal of Psychology* 95(4):537-64.

Cohen, J B and Kappauf, W E (1985), "Color mixture and fundamental metamers: Theory, algebra, geometry, application", American Journal of Psychology. 1985 Vol. 98, No 2, pp. 171-259.

Do M T, Yau K W (2010) Intrinsically photosensitive retinal ganglion cells. Physiol Rev 90(4):1547-1581.

Ecker J L, et al. (2010) Melanopsin-expressing retinal ganglion-cell photoreceptors: Cellular diversity and role in pattern vision. Neuron 67(1):49-60.

Harrington, R. E. (1954). Effect of color temperature on apparent brightness. J. Opt. Soc Lucas R J, Peirson S N, Berson D M, Brown T M, Cooper H M, Czeisler C A, Figueiro M G, Gamlin P D, Lockley S W, O'Hagan J B, Price L L A, Provencio I, Skene D J, Brainard G C (2014) Measuring and using light in the melanopsin age. *Trends in Neurosciences* 37:1-9.

McDougal, D. H. & Gamlin, P. D. 2010 The influence of intrinsically-photosensitive retinal ganglion cells on the spectral sensitivity and response dynamics of the human pupillary light reflex. Vision Res. 50, 72-87.

Royer M P & Houser K W, (2012) Spatial Brightness Perception of Trichromatic Stimuli: Leukos Vol 9, No 2, (October) pp. 89-108

Schlesselman et al (2015), Brightness judgments in a simulated sports field correlate with the S/P value of light sources. Submitted for presentation IES Conference Indianapolis, Ind.

Stockman, A., & Sharpe, L. T. (1999). *Cone spectral sensitivities and color matching*. In K. Gegenfurtner & L. T. Sharpe (Eds.), *Color vision: From Genes to Perception* (pp. 53-87) Cambridge: Cambridge University Press Stockman, A. and Sharpe, L. T. (2000) *Spectral sensitivities of the middle- and long-wavelength sensitive cones derived from measurements in observers of known genotype. Vision Research*, 40, 1711-1737.

Stockman, A., & Sharpe, L. T. (2006). *Physiologically-based colour matching functions*. In *Proceedings of the ISCC/CIE Expert Symposium '06: 75 Years of the CIE Standard Colorimetric Observer* (pp. 13-20). Vienna: CIE Central Bureau.

Vienot, F et al., (2012) "Domain of metamers exciting intrinsically photosensitive retinal ganglion cells (ipRGCs) and rods", Journal of Optical Society of America A, February 2012, Vol 29, No 2, pp. A366-A376.

What is claimed is:

1. A method of illumination comprising:
   a. designing a first and second light source wherein:
      i. the first and second light source are metamers at a defined correlated color temperature (CCT);
      ii. the spectral power distribution (SPD) of the first light source has a higher melanopic/photopic (M/P) or scotopic/photopic (S/P) ratio than the second light source;
      iii. the first and second light sources collectively produce a light output having a defined color rendering index (CRI) above 70;

iv. the first and second light sources collectively produce a light output having a defined R9 value above 8; and
v. the first and second light sources collectively produce a light output having a television lighting consistency index (TLCI) of 40;
b. installing the first and second light sources in a lighting apparatus which emits said collectively produced light output when powered; and
c. operating the lighting apparatus at a power level which produces an increased perceived brightness as compared to one or more extant metameric variations of the first and second light sources at the same CCT.

2. The method of claim 1 wherein the collectively produced light output comprises:
  a. a relative value according to the SPD above approximately 50% at 490 nm;
  b. a relative value according to the SPD above approximately 25% within 10 nm below and 15 nm above 490 nm;
  c. an M/P ratio on the order of 0.75; and
  d. wherein the CCT is defined as on the order of 3,000K.

3. The method of claim 1 wherein the collectively produced light output comprises:
  a. a relative value according to the SPD above approximately 50% at 490 nm;
  b. a relative value according to the SPD above approximately 25% within 10 nm below and 15 nm above 490 nm; and
  c. an M/P ratio on the order of 1.2 or higher.

4. The method of claim 1 wherein the CCT is defined as on the order of up to 10,000K.

5. The method of claim 1 wherein the CCT is defined as on the order of 5,700K.

6. The method of claim 1 wherein the S/P ratio is 3.57 or higher and the M/P ratio is 1.77 or higher and the CCT is defined as on the order of up to 17,000K.

7. A method of improved perceived brightness or visual acuity for observers of a scene illuminated with a plurality of light sources comprising:
  a. providing a target area to illuminate;
  b. designing illumination for the target area with light of at least relatively high melanopic content, wherein:
    i. the light of relatively high melanopic content is determined by quantifying a scotopic/photopic ratio (S/P) or melanopic/photopic ratio (M/P) of the plurality of light sources; and
    ii. selecting a quantified S/P or M/P which:
      1. uses a high color temperature to increase the S/P or M/P ratio; while
      2. maintaining a predetermined acceptable color temperature; and
  c. implementing the designed illumination at the scene with a lighting system comprising the plurality of light sources operated collectively according to the designed illumination.

8. The method of claim 7 wherein the illumination meets a given lighting standard relative to an intensity or uniformity and the lighting system is implemented at:
  a. lower energy usage; or
  b. fewer light sources;
than illumination meeting the lighting standard but of lower melanopic content because of higher perceived brightness or visual acuity of the designed illumination.

9. A method of illumination by operating an LED lighting system capable of high melanopic content lighting comprising:
  a. selecting desired color properties of the LED lighting system based, at least in part, on the general purpose of the lighting or a task to be performed thereunder;
  b. selecting a high melanopic content LED at a specified correlated color temperature wherein:
    i. the specified correlated color temperature is based, at least in part, on the task or general purpose;
  c. calculating equal perceived brightness of the high melanopic content LED;
  d. selecting a low melanopic content LED at the specified correlated color temperature; and
  e. varying an operating conditions of the high melanopic content LED and the low melanopic content LED at a constant perceived brightness in accordance with an operating profile.

* * * * *